US006872742B2

(12) United States Patent
Natchus et al.

(10) Patent No.: US 6,872,742 B2
(45) Date of Patent: Mar. 29, 2005

(54) SUBSTITUTED CYCLIC AMINE METALLOPROTEASE INHIBITORS

(75) Inventors: Michael George Natchus, Glendale, OH (US); Biswanath De, Cincinnati, OH (US); Stanislaw Pikul, Mason, OH (US); Neil Gregory Almstead, Loveland, OH (US); Roger Gunnard Bookland, Cincinnati, OH (US); Yetunde Olabisi Taiwo, West Chester, OH (US); Menyan Cheng, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 196 days.

(21) Appl. No.: 10/186,531

(22) Filed: Jul. 1, 2002

(65) Prior Publication Data

US 2003/0105153 A1 Jun. 5, 2003

Related U.S. Application Data

(63) Continuation-in-part of application No. 09/888,675, filed on Jun. 25, 2001, now Pat. No. 6,569,855, and a continuation-in-part of application No. 09/888,759, filed on Jun. 25, 2001, now abandoned, and a continuation-in-part of application No. 08/918,317, filed on Aug. 26, 1997, now Pat. No. 6,417,219.
(60) Provisional application No. 60/024,842, filed on Aug. 28, 1996.

(51) Int. Cl.$^7$ .............................................. A61K 31/40
(52) U.S. Cl. ...................................... 514/408; 514/424
(58) Field of Search .................................. 514/408, 424

(56) References Cited

U.S. PATENT DOCUMENTS

| 4,954,158 A | 9/1990 | Stammer |
| 5,455,258 A | 10/1995 | MacPherson et al. |
| 6,569,855 B2 * | 5/2003 | Natchus et al. .......... 514/235.5 |

FOREIGN PATENT DOCUMENTS

| EP | 769498 A1 | 4/1997 |
| WO | WO 88-02627 A1 | 4/1988 |
| WO | WO 96/33172 A1 | 10/1996 |
| WO | WO 97/20824 A1 | 6/1997 |
| WO | WO 97/24349 A1 | 7/1997 |
| WO | WO 97/25316 A1 | 7/1997 |

OTHER PUBLICATIONS

The Merck Manual, 15$^{th}$ eddition, 1987, pp. 415–429.*
Bonnet et al., CA 63:11477b, 1965.
Shiba et al., CA 61:16145a, 1964.
Isenberg et al., CA 59:11932c, 1963.
Andreatta et al., CA 67:117254, 1967.
Lash et al., CA 116:41240, 1992.
Setoi et al., CA 111:133982, 1989.
Andreatta et al., CA 68:118364, 1968.
Philip et al., CA 87:102614, 1977.
Hudson et al., CA 68:87526, 1968.
Weber et al., CA 110:57646, 1989.
Kaspersen et al., CA 83:193215, 1975.
Krapcho et al., CA 96:181622, 1982.
Hudson et al., CA 84:59972, 1976.
Yevich et al., CA:114:247309, 1991.
Goli et al., CA 122:133587. 1995.
Braish et al., CA 114:247308, 1991.
Jordis et al., CA 114:143341, 1991.
Remuzon et al., CA 120:164628, 1994.
Roemmele et al., CA 110:173729, 1989.
Kahl et al., CA 95:204385, 1981.
Wakamiya et al., CA 95:43606, 1981.
Shono et al., CA 101;151196, 1984.
Tronchet et al., CA 98:16975, 1983.
Koksharova et al., CA 97:16747, 1982.
Artico et al., CA 122:314404, Mar. 1995.
Matsubara et al., CA 121:275875, 1994.
Morimoto et al., CA 121:157461, 1994.
Hassan et al., CA 118:213398, 1993.
Di Cesare et al., CA 117:233883, 1992.
Wolski et al., CA 109:121786, 1988.
Belatter et al., CA 106:219573, 1987.K.
Shomo et al., CA 99:87977, 1983.
Ondetti et al., CA 94:175557, 1981.
Henry et al., CA 84:31126, 1976.
Kahl, J.U. et al., Synthesis of Two Naturally Occurring Diastereomatic Dihydroxyprolines: 2,3–trans–3,4–tras–3, 4–dihydroxy–L–prolin and 2,3–cis–3,4–tras–3,4–dihydorxy–L–proline:, *Liebigs An. Chem.*, 1981, pp. 1445–1450.
Hudson, C.B. et al., "Synthesis of 3,4–dihydroxyprolines. I. Cisglycolation of 3,4–dehydroproline Derivatives", *Aust. J. Chem.*, 1966, vol. 21, pp. 769–782.

(List continued on next page.)

*Primary Examiner*—Shengjun Wang
(74) *Attorney, Agent, or Firm*—David V. Upite; Andrew A. Paul

(57) ABSTRACT

The invention provides compounds which are useful as inhibitors of metalloproteases, and which are effective in treating conditions characterized by excess activity of these enzymes. In particular, the present invention relates to a compound having a structure according to Formula (I).

Also disclosed are compounds, pharmaceutical compositions and methods of treating diseases characterized by metalloprotease activity using these compounds or the pharmaceutical compositions containing them.

8 Claims, No Drawings

OTHER PUBLICATIONS

Andreatta, R.H. et al., "Synthesis of cis and trans isomers of 4-chloro-L-proline, 4-bromo-L-proline, and 4-amino-L-Proline", *Aust. J. Chem.*, 1967, vol. 20, pp. 1493–1509.

Heintzelman, G.R. et al., "Imino Diels–Alder–Based Construction of a Piperidine A–Ring Unit for Total Synthesis of the Marine Hepatotoxin Cylindrospermopsin", *Chemical Abstracts*, Jul. 29, 1986, vol. 125. No. 5, Abstract No. 058826.

Herdeis, C. et al., "Amino acids. XII. (.+–.)–Pipecolic acid derivatives. Part 2, An expedient synthetic entry to substituted pipcolic acids", *Chemical Abstracts*, Oct. 26, 1992, vol. 117, No. 17. Abstract No. 171989.

Edwards, M.L. et al., "Synthesis and enzymic resolution of a carbocyclic analog of ribofuranosylamine", *Chemical Abstracts*, Jul. 1, 1996, vol. 125, No. 1, Abstract No. 011281.

* cited by examiner

SUBSTITUTED CYCLIC AMINE METALLOPROTEASE INHIBITORS

CROSS REFERENCE

This is a Continuation-in-Part of U.S. application Ser. No. 09/888,675, now U.S. Pat. No. 6,569,855, Ser. No. 09/888,759, now abandoned, filed concurrently on Jun. 25, 2001, Ser. No. 08/918,317, filed Aug. 26, 1997, now U.S. Pat. No. 6,419,219 which claims priority under Title 35, United States Code 119(e) from Provisional Application Ser. No. 60/024,842, filed Aug. 28, 1996.

TECHNICAL FIELD

This invention is directed to compounds which are useful in treating diseases associated with metalloprotease activity, particularly zinc metalloprotease activity.

BACKGROUND

Background

A number of structurally related metalloproteases [MPs] effect the breakdown of structural proteins. These metalloproteases often act on the intercellular matrix, and thus are involved in tissue breakdown and remodeling. Such proteins are referred to as metalloproteases or MPs. There are several different families of MPs, classified by sequence homology. Several families of known MPs, as well as examples thereof, are disclosed in the art.

These MPs include Matrix-Metallo Proteases [MMPs], zinc metalloproteases, many of the membrane bound metalloproteases, TNF converting enzymes, angiotensin-converting enzymes (ACEs), disintegrins, including ADAMs (See Wolfsberg et al, 131 *J. Cell Bio.* 275–78 October, 1995), and the enkephalinases. Examples of MPs include human skin fibroblast collagenase, human skin fibroblast gelatinase, human sputum collagenase, aggrecanse and gelatinase, and human stromelysin. Collagenase, stromelysin, aggrecanase and related enzymes are thought to be important in mediating the symptomatology of a number of diseases.

Potential therapeutic indications of MP inhibitors have been discussed in the literature. See for example, U.S. Pat. No. 5,506,242 (Ciba Geigy Corp.); U.S. Pat. No. 5,403,952 (Merck & Co.); PCT published application WO 96/06074 (British Bio Tech Ltd); PCT Publication WO 96/00214 (Ciba Geigy); WO 95/35275 (British Bio Tech Ltd); WO 95/35276 (British Bio Tech Ltd); WO 95/33731 (Hoffman-LaRoche); WO 95/33709 (Hoffman-LaRoche); WO 95/32944 (British Bio Tech Ltd); WO 95/26989 (Merck); WO 9529892 (DuPont Merck); WO 95/24921 (Inst. Opthamology); WO 95/23790 (SmithKline Beecham); WO 95/22966 (Sanofi Winthrop); WO 95/19965 (Glycomed); WO 95 19956 (British Bio Tech Ltd); WO 95/19957 (British Bio Tech Ltd); WO 95/19961 (British Bio Tech Ltd) WO 95/13289 (Chiroscience Ltd.); WO 95/12603 (Syntex); WO 95/09633 (Florida State Univ); WO 95/09620 (Florida State Univ.); WO 95/04033 (Celltech); WO 94/25434 (Celltech); WO 94/25435 (Celltech); WO 93/14112 (Merck); WO 94/0019 (Glaxo); WO 93/21942 (British Bio Tech Ltd); WO 92/22523 (Res. Corp. Tech. Inc.); WO 94/10990 (British Bio Tech Ltd); WO 93/09090 (Yamanouchi); and British patents GB 2282598 (Merck) and GB 2268934 (British Bio Tech Ltd); Published European Patent Applications EP 95/684240 (Hoffman LaRoche); EP 574758 (Hoffman LaRoche); EP 575844 (Hoffman LaRoche); Published Japanese applications; JP 08053403 (Fujusowa Pharm. Co. Ltd.); JP 7304770 (Kanebo Ltd.); and Bird et al *J. Med Chem* vol. 37, pp. 158–69 (1994). Examples of potential therapeutic uses of MP inhibitors include rheumatoid arthritis (Mullins, D. E., et at., *Biochim. Biophys. Acta.* (1983) 695:117–214); osteoarthritis (Henderson, B., et al., *Drugs of the Future* (1990) 15:495–508); the metastasis of tumor cells (ibid, Broadhurst, M. J., et al., European Patent Application 276,436 (published 1987), Reich, R., et al., 48 *Cancer Res.* 3307–3312 (1988); and various ulcerations or ulcerative conditions of tissue. For example, ulcerative conditions can result in the cornea as the result of alkali burns or as a result of infection by *Pseudomonas aeruginosa*, Acanthamoeba, Herpes simplex and vaccinia viruses.

Other examples of conditions characterized by undesired metalloprotease activity include periodontal disease, epidermolysis bullosa, fever, inflammation and scleritis (Cf. DeCicco et al, WO 95 29892 published Nov. 9, 1995).

In view of the involvement of such metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa, et al.; U.S. Pat. No. 4,771,038, issued Sep. 13, 1988 to Wolanin, et al.; U.S. Pat. No. 4,743,587, issued May 10, 1988 to Dickens, et al., European Patent Publication Number 575,844, published Dec. 29, 1993 by Broadhurst, et al.; International Patent Publication No. WO 93/09090, published May 13, 1993 by Isomura, et al.; World Patent Publication 92/17460, published Oct. 15, 1992 by Markwell et al.; and European Patent Publication Number 498,665, published Aug. 12, 1992 by Beckett, et al.

Though a variety of inhibitors have been prepared, there is a continuing need for potent matrix metalloprotease inhibitors useful in treating such diseases. It would be advantageous to inhibit these metalloproteases as a method of treating diseases related to unwanted metalloprotease activity. Though a variety of inhibitors have been prepared, there is a continuing need for potent metalloprotease inhibitors useful in treating such diseases.

OBJECTS OF THE INVENTION

It is an object of the invention to provide potent inhibitors of metalloproteases.

It is a further object of the invention to provide pharmaceutical compositions comprising such inhibitors.

It is also an object of the invention to provide a method of treatment for metalloprotease related maladies.

SUMMARY OF THE INVENTION

The invention provides compounds which are useful as inhibitors of metalloproteases, and which are effective in treating conditions characterized by excess activity of these enzymes. In particular, the present invention relates to a compound having a structure according to Formula (I)

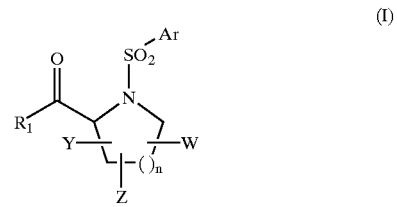

wherein

Ar is alkyl, heteroalkyl, aryl or heteroaryl, substituted or unsubstituted;

$R_1$ is OH, alkoxy, $NHOR_2$, where $R_2$ is hydrogen or alkyl;

W is one or more of hydrogen, lower alkyl or an alkylene bridge;

Y is independently one or more of hydroxy, $SR_3$, $SOR_4$, $SO_2R_5$, alkoxy, amino, wherein amino is of formula $NR_6,R_7$, wherein $R_6$ and $R_7$ are independently chosen from hydrogen, alkyl, heteroalkyl, heteroaryl, aryl, $OR_3$, $SO_2R_8$, $COR_9$, $CSR_{10}$, $PO(R_{11})_2$; and $R_3$ is hydrogen, alkyl, aryl, heteroaryl;

$R_4$ is alkyl, aryl, heteroaryl;

$R_8$ is alkyl, aryl, heteroaryl, heteroalkyl, amino, alkylamino, dialkylamino, arylamino, diarylamino and alkylarylamino;

$R_9$ is hydrogen, alkoxy, aryloxy, heteroaryloxy, alkyl, aryl, heteroaryl, heteroalkyl, amino, alkylamino, dialkylamino, arylamino and alkylarylamino;

$R_{10}$ is alkyl, aryl, heteroaryl, heteroalkyl, amino, alkylamino, dialkylamino, arylamino, diarylamino and alkylarylamino;

$R_{11}$ is alkyl, aryl, heteroaryl, heteroalkyl;

Z is hydrogen, hydroxy, alkyl, alkylene or heteroalkylene;

n is 1–3.

This structure also includes an optical isomer, diastereomer or enantiomer for Formula (I), or a pharmaceutically-acceptable salt, or biohydrolyzable amide, ester, or imide thereof.

These compounds have the ability to inhibit at least one mammalian matrix metalloprotease. Accordingly, in other aspects, the invention is directed to pharmaceutical compositions containing the compounds of Formula (I), and to methods of treating diseases characterized by metalloprotease activity using these compounds or the pharmaceutical compositions containing them.

Applicants have found that compounds of Formula (I) are potent inhibitors of metalloproteases. The compounds of the present invention therefore are useful for the treatment of conditions and diseases which are characterized by unwanted activity by the class of proteins which destroy structural proteins.

Metalloproteases active at a particularly undesired location (e.g., an organ or certain types of cells) can be targeted by conjugating the compounds of the invention to a targeting ligand specific for a marker at that location such as an antibody or fragment thereof or a receptor ligand. Conjugation methods are known in the art.

The invention is also directed to various other processes which take advantage of the unique properties of these compounds. Thus, in another aspect, the invention is directed to the compounds of Formula (I) conjugated to solid supports. These conjugates can be used as affinity reagents for the purification of a desired metalloprotease.

In another aspect, the invention is directed to the compounds of Formula (I) conjugated to label. As the compounds of the invention bind to at least one metalloprotease, the label can be used to detect the presence of relatively high levels of metalloprotease in vivo or in vitro cell culture.

In addition, the compounds of Formula (I) can be conjugated to carriers which permit the use of these compounds in immunization protocols to prepare antibodies specifically immunoreactive with the compounds of the invention. Typical conjugation methods are known in the art. These antibodies are then useful both in therapy and in monitoring the dosage of the inhibitors.

DETAILED DESCRIPTION

The compounds of the present invention are inhibitors of mammalian metalloproteases. Preferably, the compounds are those of Formula (I) or a pharmaceutically-acceptable salt, or biohydrolyzable amide, ester, or imide thereof.

Definitions and Usage of Terms

The following is a list of definitions for terms used herein:

"Acyl" or "carbonyl" is described as a radical which could be formed by removal of the hydroxy from a carboxylic acid (i.e., R—C(═O)—). Preferred acyl groups include (for example) acetyl, formyl, and propionyl.

"Acyloxy" is an oxy radical having an acyl substituent (i.e., —O-acyl); for example,—O—C(═O)-alkyl.

"Alkoxyacyl" is an acyl radical (—C(═O)—) having an alkoxy subtituent (i.e., —O—R), for example, —C(═O)—O-alkyl. This radical can be referred to as an ester.

"Acylamino" is an amino radical having an acyl substituent (i.e., —N-acyl); for example, —NH—C(═O)-alkyl.

"Alkenyl" is an unsubstituted or substituted hydrocarbon chain radical having 2 to 15 carbon atoms; preferably from 2 to 10 carbon atoms; more preferably from 2 to 8; except where indicated. Alkenyl substituents have at least one olefinic double bond (including, for example, vinyl, allyl and butenyl).

"Alkynyl" is an unsubstituted or substituted hydrocarbon chain radical having 2 to 15 carbon atoms; preferably from 2 to 10 carbon atoms; more preferably from 2 to 8; except where indicated. The chain has at least one carbon-carbon triple bond.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Alkoxyalkyl" is an unsubstituted or substituted alkyl moiety substituted with an alkoxy moiety (i.e., -alkyl-O-alkyl). Preferred is where the alkyl has 1 to 6 carbon atoms (more preferably 1 to 3 carbon atoms), and the alkyoxy has 1 to 6 carbon atoms (more preferably 1 to 3 carbon atoms).

"Alkyl" is an unsubstituted or substituted saturated hydrocarbon chain radical having 1 to 15 carbon atoms; preferably from 1 to 10 carbon atoms; more preferably 1 to 4; except where indicated. Preferred alkyl groups include (for example) substituted or unsubstituted methyl, ethyl, propyl, isopropyl, and butyl.

Alkylene refers to an alkyl, alkenyl or alkynyl which is diradical, rather than a radical. "Hetero alkylene" is likewise defined as a (diradical) alkylene having a heteroatom in its chain, hence an "alkylene bridge" is a hydrocarbon diradical that attaches to two different carbons (hence making a bicyclic structure), preferred alkylene bridges include methylene, ethylene and propylene.

"Alkylamino" is an amino radical having one (secondary amine) or two (tertiary amine) alkyl substituents (i.e., —N-alkyl). For example, methylamino (—NHCH$_3$), dimethylamino (—N(CH$_3$)$_2$), methylethylamino (—N(CH$_3$)CH$_2$CH$_3$).

"Aminoacyl" is acyl radical having an amino substituent (i.e., —C(═O)—N); for example, —C(═O)—NH$_2$. The amino group of the aminoacyl moiety may be unsubstituted (i.e., primary amine) or may be substituted with one (secondary amine) or two (i.e., tertiary amine) alkyl groups.

"Aryl" is an aromatic carbocyclic ring radical. Preferred aryl groups include (for example) phenyl, tolyl, xylyl, cumenyl and naphthyl.

"Arylalkyl" is an alkyl radical substituted with an aryl group. Preferred arylalkyl groups include benzyl, phenylethyl, and phenylpropyl.

"Arylalkylamino" is an amine radical substituted with an arylalkyl group (e.g., —NH-benzyl).

"Arylamino" is an amine radical substituted with an aryl group (i.e., —NH-aryl).

"Aryloxy" is an oxygen radical having an aryl substituent (i.e., —O-aryl).

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic carbocyclic rings generally contain 4 to 9 atoms, preferably 4 to 7 atoms. Polycyclic carbocyclic rings contain 7 to 17 atoms, preferably from 7 to 12 atoms. Preferred polycyclic systems comprise 4-, 5-, 6- or 7-membered rings fused to 5-, 6-, or 7-membered rings.

"Carbocycle-alkyl" is an unsubstituted or substituted alkyl radical substituted with a carbocyclic ring. Unless otherwise specified, the carbocyclic ring is preferably an aryl or cycloalkyl; more preferably an aryl. Preferred carbocycle-alkyl groups include benzyl, phenylethyl and phenylpropyl.

"Carbocycle-heteroalkyl" is an unsubstituted or substituted heteroalkyl radical substituted with a carbocyclic ring. Unless otherwise specified, the carbocyclic ring is preferably an aryl or cycloalkyl; more preferably an aryl. The heteroalkyl is preferably 2-oxa-propyl, 2-oxa-ethyl, 2-thia-propyl, or 2-thia-ethyl.

"Carboxyalkyl" is an unsubstituted or substituted alkyl radical substituted with with a carboxy (—C(=O)OH) moiety. For example, —CH$_2$—C(=O)OH.

"Cycloalkyl" is a saturated carbocyclic ring radical. Preferred cycloalkyl groups include (for example) cyclopropyl, cyclobutyl and cyclohexyl.

"Cycloheteroalkyl" is a saturated heterocyclic ring. Preferred cycloheteroalkyl groups include (for example) morpholinyl, piperadinyl, and piperazinyl.

"Fused rings" are rings that are superimposed together such that they share two ring atoms. A given ring may be fused to more than one other ring. Fused rings are contemplated in heteroaryl, aryl and heterocycle radicals or the like.

"Heterocycle-alkyl" is an alkyl radical substituted with a heterocyclic ring. The heterocyclic ring is preferably an heteroaryl or cycloheteroalkyl; more preferably an heteroaryl. Preferred heterocycle alkyl include $C_1$–$C_4$ alkyl having preferred heteroaryl appended to them. More preferred is, for example, pyridyl alkyl, and the like.

"Heterocycle-heteroalkyl" is an unsubstituted or substituted heteroalkyl radical substituted with a heterocyclic ring. The heterocyclic ring is preferably an aryl or cycloheteroalkyl; more preferably an aryl.

"Heteroatom" is a nitrogen, sulfur or oxygen atom. Groups containing one or more heteroatoms may contain different heteroatoms.

"Heteroalkenyl" is an unsubstituted or substituted unsaturated chain radical having 3 to 8 members comprising carbon atoms and one or two heteroatoms. The chain has at least one carbon-carbon double bond.

"Heteroalkyl" is an unsubstituted or substituted saturated chain radical having 2 to 8 comprising carbon atoms and one or two heteroatoms.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic heterocyclic rings contain 3 to 9 atoms, preferably 4 to 7 atoms. Polycyclic rings contain 7 to 17 atoms, preferably from 7 to 13 atoms.

"Heteroaryl" is an aromatic heterocyclic ring, either monocyclic or bicyclic radical. Preferred heteroaryl groups include (for example) thienyl, furyl, pyrrolyl, pyridinyl, pyrazinyl, thiazolyl, pyrimidinyl, quinolinyl, and tetrazolyl, benzo thiazolyl, benzofuryl, indolyl and the like.

"Halo", "halogen", or "halide" includes chloro, bromo, fluoro or iodo, preferably chloro and fluoro.

Also, as referred to herein, a "lower" hydrocarbon moiety (e.g., "lower" alkyl) is a hydrocarbon chain comprised of 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium) and organic salts. Preferred anionic salts include the halides (such as chloride salts). Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of of such salts is within the purview of the skilled artisan's practice.

"Biohydrolyzable amides" are amides of a metalloprotease inhibitor that do not interfere with the inhibitory activity of the compound, or that are readily converted in vivo by an animal, preferably a mammal, more preferably a human subject to yield an active metalloprotease inhibitor.

A "biohydrolyzable hydroxy imide" is an imide of a Formula (I) compound that does not interfere with the metalloprotease inhibitory activity of these compounds, or that is readily converted in vivo by an animal, preferably a mammal, more preferably a human subject to yield an active Formula (I) compound.

A "biohydrolyzable ester" refers to an ester of a Formula (I) compound that does not interfere with the metalloprotease inhibitory activity of these compounds or that is readily converted by an animal to yield an active Formula (I) compound.

A "solvate" is a complex formed by the combination of a solute (e.g., a metalloprotease inhibitor) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

"Optical isomer", "stereoisomer", "diastereomer" as referred to herein have the standard art recognized meanings (Cf., *Hawley's Condensed Chemical Dictionary*, 11th Ed.).

The illustration of specific protected forms and other derivatives of the Formula (I) compounds is not intended to be limiting. The application of other useful protecting groups, salt forms, etc. is within the ability of the skilled artisan.

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

As used herein, "mammalian metalloprotease" refers to the proteases disclosed in the "Background" of this application. Preferred "mammalian metalloproteases" include any metal-containing (preferably zinc-containing) enzyme found in animal, preferably mammalian sources capable of catalyzing the breakdown of collagen, gelatin or proteoglycan under suitable assay conditions. Appropriate assay conditions can be found, for example, in U.S. Pat. No. 4,743,587, which references the procedure of Cawston, et al., *Anal. Biochem.* (1979) 99:340–345, use of a synthetic substrate is described by Weingarten, H., et al., *Biochem. Biophy. Res. Comm.* (1984) 139:1184–1187. Any standard method for analyzing the breakdown of these structural proteins can, of course, be used. More preferred metalloprotease enzymes are zinc-containing proteases which are similar in structure to, for example, human stromelysin or skin fibroblast collagenase. The ability of candidate compounds to inhibit metalloprotease activity can, of course, be tested in the assays described above. Isolated metalloprotease enzymes can be used to confirm the inhibiting activity of the invention compounds, or crude extracts which contain the range of enzymes capable of tissue breakdown can be used.

Compounds:

Compounds of the invention are described in the Summary of the Invention, more preferred compounds of Formula (I) include,

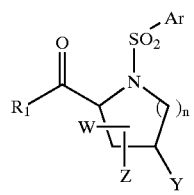

(I)

wherein

Ar is aryl or heteroaryl, substituted or unsubstituted;

$R_1$ is OH, alkoxy, $NHOR_2$, where $R_2$ is hydrogen or alkyl;

W is one or more of hydrogen, lower alkyl;

Y is independently one or more of hydroxy, $SR_3$, $SOR_4$, $SO_2R_5$, alkoxy, amino, wherein amino is of formula $NR_6R_7$, wherein $R_6$ and $R_7$ are independently chosen from hydrogen, alkyl, heteroalkyl, heteroaryl, aryl, $OR_3$, $SO_2R_8$, $COR_9$, $CSR_{10}$, $PO(R_{11})_2$; and $R_3$ is hydrogen, alkyl, aryl, heteroaryl;

$R_4$ is alkyl, aryl, heteroaryl;

$R_8$ is alkyl, aryl, heteroaryl, heteroalkyl, amino, alkylamino, dialkylamino, arylamino, diarylamino and alkylarylamino;

$R_9$ is hydrogen, alkoxy, aryloxy, heteroaryloxy, alkyl, aryl, heteroaryl, heteroalkyl, amino, alkylamino, dialkylamino, arylamino and alkylarylamino;

$R_{10}$ is alkyl, aryl, heteroaryl, heteroalkyl, amino, alkylamino, dialkylamino, arylamino, diarylamino and alkylarylamino;

$R_{11}$ is alkyl, aryl, heteroaryl, heteroalkyl;

Z is hydrogen;

n is 1–3.

There may be one or more W, Y and Z moieties on the molecule of the invention. Preferably there are five or less substituents chosen from W, Y and Z which are not hydrogen. Y and Z moieties may appear on the same carbon, i.e., geminal in relation to each other.

Where Z is heteroalkylene, it is preferred that heteroatoms adjacent to the parent ring structure, more preferably such heteroalkyls have 2 to 4 members. Preferred heteroatoms are divalent.

Preferred Ar include aryl and alkyl moieties. When Ar is aryl, it includes heterocyclic and carbocyclic aryl, either monocyclic or polycyclic, preferably monocyclic aryl, more preferably phenyl; When Ar is alkyl, it is preferably $C_1$ to $C_{18}$ alkyl, more preferably $C_2$ to $C_8$ alkyl or heteroalkyl. Ar can be substituted or unsubstituted.

W is preferably a $C_1$ to $C_4$ alkyl or $C_1$ to $C_4$ alkylene bridge. When W is an alkylene bridge, it is preferably methylene, ethylene or propylene, more preferably methylene. When W is alkyl it is preferably methyl or ethyl, more preferably methyl.

The variable "n" alters the size of the nitrogen containing ring, more preferred ring sizes are 5 and 6 membered rings.

Compound Preparation:

The hydroxamic compounds of Formula (I) can be prepared using a variety of procedures.

The starting materials used in preparing the compounds of the invention are known, made by known methods, or are commercially available as a starting material. General schemes and representative examples of the preparation of compounds of the invention follow.

In the following scheme W and Z are omitted for clarity. The skilled artisan will appreciate that Z may be added using similar methodologies or those known in the art. W may be added by art recognized methodologies as well. For compounds where Y is not adjacent to the ring nitrogen, a preferred method of making the compounds is;

SCHEME 1

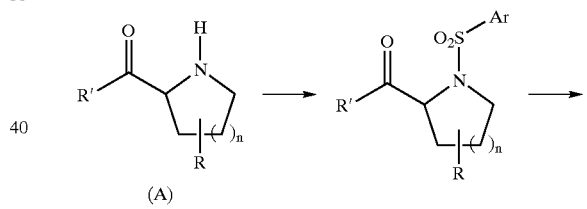

(A)

Where R is a derivatizable group or can be manipulated or substituted, such compounds are known or are prepared by known methods. For example, when R is OH, and n is 1, hydroxyproline (A) is converted to its analogous sultamester and the hydroxyl is then manipulated to give (B) during this or a subsequent step Y and Z can be added or altered, followed by treatment with hydroxyl amine under basic conditions to give (C).

R' may be a protecting group, a free acid or any moiety the skilled artisan prefers, provided that ultimately it provides the compounds of the invention.

A variety of compounds can be generated in a similar fashion, using the guidance of the scheme above.

It is recognized that it is preferable to use a protecting group for any reactive functionality such as a carboxyl, hydroxyl and the like, during the formation of the sultamester. This is standard practice, well within the normal practice of the skilled artisan.

In the above schemes, where R is alkoxy or alkylthio, the corresponding hydroxy or thiol compounds are derived from the final compounds by using a standard dealkylating procedure (Bhatt, et al., "Cleavage of Ethers", *Synthesis,* 1983, pp. 249–281).

These steps may be varied to increase yield of desired product. The skilled artisan will recognize the judicious choice of reactants, solvents, and temperatures is an important component in any successful synthesis. Determination of optimal conditions, etc. is routine. Thus the skilled artisan can make a variety of compounds using the guidance of the scheme above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and soponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will readily appreciate that certain reactions are best carried out when other potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

Methods of Use

Metalloproteases (MPs) found in the body operate, in part, by breaking down the extracellular matrix, which comprises extracellular proteins and glycoproteins. These proteins and glycoproteins play an important role in maintaining the size, shape, structure and stability of tissue in the body. Inhibitors of metalloproteases are useful in treating diseases caused, at least in part, by breakdown of such proteins. It is known that MPs are intimately involved in tissue remodeling. As a result of this activity they have been said to be active in many disorders involving either the:

breakdown of tissues; including degenerative diseases, such as arthritis, multiple sclerosis and the like; metastasis or mobility of tissues in the body:

the remodeling of tissues, including fibrotic disease, scarring, benign hyperplasia, and the like.

The compounds of the present invention treat disorders, diseases and/or unwanted conditions which are characterized by unwanted or elevated activity by that class of proteases. For example the compounds can be used to inhibit proteases which:

destroy structural proteins (i.e. the proteins that maintain tissue stability and structure);

interfere in inter/intracellular signaling, including those implicated in cytokine up-regulation, and/or cytokine processing and/or inflammation, tissue degradation and other maladies [Mohler K M, et al, Nature 370 (1994) 218–220, Gearing A J H, et al, Nature 370 (1994) 555–557 McGeehan G M, et al, Nature 370 (1994) 558–561], and/or facilitate processes which are undesired in the subject being treated, for example, the processes of sperm maturation, egg fertilization and the like.

The term "treatment" is used herein to mean that, at a minimum, administration of a compound of the present invention that mitigates a "MP related disorder or disease" in a mammalian subject, preferably in humans. Thus, the term "treatment" includes: preventing an MP related disorder from occurring in a mammal, particularly when the mammal is predisposed to acquiring the MP related disorder, but has not yet been diagnosed with the disease; inhibiting the MP related disorder; and/or alleviating or reversing the MP related disorder. Insofar as the methods of the present invention are directed to preventing an MP related disorder, it is understood that the term "prevent" does not require that the MP related disorder be completely thwarted. (See Webster's Ninth Collegiate Dictionary.) Rather, as used herein, the term "preventing" refers to the ability of the skilled artisan to identify a population that is susceptible to MP related disorder, such that administration of the compounds of the present invention may occur prior to the onset of the symptoms of the MP related disorder. The population that is at risk of a MP related disorder, for example as heart disease, are those who have a genetic predisposition to heart disease as indicated by family history of the disease. Other risk factors include obesity, stress, and/or a diet high in atherogenic lipids.

Thus, the patient population is identifiable and could receive the administration of a composition of the present invention before progression of the disease. Thus, progression of the MP related disorder in such individuals would be "prevented."

As used herein, a "MP related disorder" or "a MP related disease" is one that involves unwanted or elevated MP activity in the biological manifestation of the disease or disorder; in the biological cascade leading to the disorder; or as a symptom of the disorder. This "involvement" of the MP includes;

The unwanted or elevated MP activity as a "cause" of the disorder or biological manifestation, whether the activity was elevated genetically, by infection, by autoimmunity, trauma, biomechanical causes, lifestyle [e.g. obesity] or by some other cause;

The MP as part of the observable manifestation of the disease or disorder. That is, the disease or disorder is measurable in terms of the increased MP activity, or from a clinical standpoint, unwanted or elevated MP levels indicate the disease. MPs need not be the "hallmark" of the disease or disorder;

The unwanted or elevated MP activity is part of the biochemical or cellular cascade that results or relates to the disease or disorder. In this respect, inhibition of the MP activity interrupts the cascade, and thus controls the disease.

Advantageously, many MPs are not distributed evenly throughout the body. Thus the distribution of MPs expressed in various tissues are often specific to those tissues. For example, the distribution of metalloproteases implicated in the breakdown of tissues in the joints, is not the same as the distribution of metalloproteases found in other tissues. Thus, though not essential for activity or efficacy, certain disorders preferably are treated with compounds that act on specific MPs found in the affected tissues or regions of the body. For example, a compound which displays a higher degree of affinity and inhibition for a MP found in the joints (e.g. chondrocytes) would be preferred for treatment of disease found there than other compounds which are less specific.

In addition, certain inhibitors are more bioavialable to certain tissues than others, and this judicious choice of inhibitor, with the selectivity described above provides for specific treatment of the disorder, disease or unwanted condition. For example, compounds of this invention vary in their ability to penetrate into the central nervous system. Thus compounds may be selected to produce effects mediated through MPs found specifically outside the central nervous system.

Determination of the specificity of a MP inhibitor of a certain MP is within the skill of the artisan in that field. Appropriate assay conditions can be found in the literature. Specifically assays are known for stromelysin and collagenase. For example, U.S. Pat. No. 4,743,587 references the procedure of Cawston, et al., *Anal Biochem* (1979) 99:340–345. The use of a synthetic substrate in an assay is described by Weingarten, H., et al., *Biochem Biophy Res Comm* (1984) 139:1184–1187. Any standard method for analyzing the breakdown of structural proteins by MPs can, of course, be used. The ability of compounds of the invention to inhibit metalloprotease activity can, of course, be tested in the assays found in the literature, or variations thereof. Isolated metalloprotease enzymes can be used to confirm the inhibiting activity of the invention compounds, or crude extracts which contain the range of enzymes capable of tissue breakdown can be used.

As a result of the MP inhibitory effect of the compounds of the invention, the compounds of the invention are also useful in treating the following disorders by virtue of their metalloprotease activity.

The compounds of this invention are also useful for the prophylactic or acute treatment. They are administered in any way the skilled artisan in the fields of medicine or pharmacology would desire. It is immediately apparent to the skilled artisan that preferred routes of administration will depend upon the disease state being treated, and the dosage form chosen. Preferred routes for systemic administration include administration perorally or parenterally.

However, the skilled artisan will readily appreciate the advantage of administering the MP inhibitor directly to the affected area for many disorders. For example, it may be advantageous to administer MP inhibitors directly to the area of the disease or condition as in area affected by surgical trauma (e.g., angioplasty), area affected by scarring or burn (e.g., topical to the skin), Because the remodeling of bone involves MPs, the compounds of the invention are useful in preventing prosthesis loosening. It is known in the art that over time prostheses loosen, become painful, and may result in further bone injury, thus demanding replacement. The need for replacement of such prostheses includes those such as in, joint replacements (for example hip, knee and shoulder replacements), dental prosthesis, including dentures, bridges and prosthesis secured to the maxilla and/or mandible.

MPs are also active in remodeling of the cardiovascular system (for example, in congestive heart failure). It has been suggested that one of the reasons angioplasty has a higher than expected long term failure rate (reclosure over time) is that MP activity is not desired or is elevated in response to what may be recognized by the body as "injury" to the basement membrane of the vessel. Thus regulation of MP activity in indications such as dilated cardiomyopathy, congestive heart failure, atherosclerosis, plaque rupture, reperfusion injury, ischemia, chronic obstructive pulmonary disease, angioplasty restenosis and aortic aneurysm may increase long term success of any other treatment, or may be a treatment in itself.

In one aspect of the present invention, the compounds of Formula I of the present invention may be effective in preventing or treating myocardial infarction (hereinafter "MI"). MI, also known as a "heart attack" or "heart failure," is a condition caused by partial or complete occlusion of one or more of the coronary arteries, usually due to rupture of an atherosclerotic plaque. The occlusion of the coronary artery results in cardiac ischemia. MMPs are implicated in artherosclerotic plaque rupture. See e.g., Galis, Z. S., et al., J. Clin. Invest. 1994;94:2493–503; Lee, R. T., et al., Arterioscler. Thromb. Vasc. Biol. 1996; 16:1070–73; Schonbeck, U. et al., Circulation Research 1997; 81(3), 448–454. Libby, P. et al., Circ. 1995;91:2844–50.

In another aspect of the invention, the compounds of the present invention may be effective in preventing or treating progressive ventricular dilation after a MI, the major contributing factor to the development of post-MI chronic heart failure (hereinafter "CHF"). Thus, in yet still another aspect of the invention, the compounds of the present invention may be effective in preventing or treating the development of post-MI chronic heart failure.

It is widely recognized that important structural changes occur within the ventricular myocardium following MI that results in alterations in LV geometry and function. These structural alterations occur in the infarct itself, in the border zone of the MI, and in regions remote from the MI that collectively result in progressive ventricular dilation and pump dysfunction. The most notable feature of this remodeling process is the region of the original MI appears to enlarge with thinning of the ventricular myocardial wall. This type of remodeling following the initial injury and healing process from an MI has been termed "infarct expansion." A significant body of work suggests that treatment of acute myocardial infarction with an MMP inhibitor will limit the unfavorable dilation of the heart that occurs early after such an event and therefore improve outcomes by preventing long-term sequelae, such as the development of chronic heart failure. See, e.g., Spinale, F. G. et al., Circulation Research 82:482–495 (1998); McElmurray, J. H. I. et al., J. Pharmacol. Exp. Ther. 291:799–811 (1999); Thomas, C. V. et al., Circulation 97:1708–1715 (1998); Spinale, F. G. et al. Circ. 102:1944–49 (2000); Peterson, J. T. et al., Cardiovasc. Res., 46(2):307–15 (2000); Rohde, L. E. et al., Circ., 99:3063–70 (1999); Lindsey, M. L. et al., *Circ.* 105:753–58 (2002); Brinsa, T. A. et al., J. Cardiac Failure, 7 Suppl. 2:24 (2001); Mukherjee, R. et al., J. Cardiac Failure;7 Suppl 2:7 (2001).

A suitable MI cardiac pharmacological model is described in Mukherjee, R. et al., J. Cardiac Failure;7 Suppl 2:7 (2001). Briefly, pigs are prepared for the induction of myocardial infarction by implantation of an occlusion device on the circumflex coronary artery, and radiopaque markers are placed in the region destined to be infarcted to measure infarct expansion (see below). Measurements of left ventricular (hereinafter "LV") volumes and distances between marker beads are made prior to and at various times after the induction of MI induced by activating the occlusion device.

The effects of selective MMP inhibition may be studied in a pig model of MI induced by ligation of the circumflex coronary artery. Animals are assigned to one of the following treatment groups: (1) 1 or 10 mg/kg three times a day of a compound of Formula (I) by oral administration starting 3 days prior to myocardial infarction; (2) 10 mg/kg three times a day of said compound by oral administration starting 3 days after MI; (3) MI with no active treatment; or (4) no myocardial infarction or drug treatment. At 10 days post-MI, LV end-diastolic volume (hereinafter "LVEDV") is measured by ventriculography. LVEDV is increased in all MI groups. An attenuated increase in LVEDV by a compound of Formula (I) indicates that the compound may be effective in the prevention or treatment of progressive ventricular dilation, and thus the subsequent development of CHF.

In skin care, MPs are implicated in the remodeling or "turnover" of skin. As a result, the regulation of MPs improves treatment of skin conditions including but not limited to, wrinkle repair, regulation and prevention and repair of ultraviolet induced skin damage. Such a treatment includes prophylactic treatment or treatment before the physiological manifestations are obvious. For example, the MP may be applied as a pre-exposure treatment to prevent ultraviolet, damage and/or during or after exposure to prevent or minimize post-exposure damage. In addition, MPs are implicated in skin disorders and diseases related to abnormal tissues that result from abnormal turnover, which includes metalloprotease activity, such as epidermolysis bullosa, psoriasis, scleroderma and atopic dermatitis. The compounds of the invention are also useful for treating the consequences of "normal" injury to the skin including scarring or "contraction" of tissue, for example, following burns. MP inhibition is also useful in surgical procedures involving the skin for prevention of scarring, and promotion of normal tissue growth including in such applications as limb reattachment and refractory surgery (whether by laser or incision).

In addition, MPs are related to disorders involving irregular remodeling of other tissues, such as bone, for example, in otosclerosis and/or osteoporosis, or for specific organs, such as in liver cirrhosis and fibrotic lung disease. Similarly in diseases such as multiple sclerosis, MPs may be involved in the irregular modeling of blood brain barrier and/or myelin sheaths of nervous tissue. Thus regulating MP activity may be used as a strategy in treating, preventing, and controlling such diseases.

MPs are also thought to be involved in many infections, including cytomegalovirus; [CMV] retinitis; HIV, and the resulting syndrome, AIDS.

MPs may also be involved in extra vascularization where surrounding tissue needs to be broken down to allow new blood vessels such as in angiofibroma and hemangioma.

Since MPs break down the extracellular matrix, it is contemplated that inhibitors of these enzymes can be used as birth control agents, for example in preventing ovulation, in preventing penetration of the sperm into and through the extracellular milieu of the ovum, implantation of the fertilized ovum and in preventing sperm maturation.

In addition they are also contemplated to be useful in preventing or stopping premature labor and delivery.

Since MPs are implicated in the inflammatory response, and in the processing of cytokines the compounds are also useful as anti-inflammatories, for use in disease where inflammation is prevalent including, inflammatory bowel disease, Crohn's disease, ulcerative colitis, pancreatitis, diverticulitis, asthma or related lung disease, rheumatoid arthritis, gout and Reiter's Syndrome.

Where autoimmunity is the cause of the disorder, the immune response often triggers MP and cytokine activity. Regulation of MPs in treating such autoimmune disorders is a useful treatment strategy. Thus MP inhibitors can be used for treating disorders including, lupus erythmatosis, ankylosing spondylitis, and autoimmune keratitis. Sometimes the side effects of autoimmune therapy result in exacerbation of other conditions mediated by MPs, here MP inhibitor therapy is effective as well, for example, in autoimmune-therapy-induced fibrosis.

In addition, other fibrotic diseases lend themselves to this type of therapy, including pulmonary disease, bronchitis, emphysema, cystic fibrosis, acute respiratory distress syndrome (especially the acute phase response).

Where MPs are implicated in the undesired breakdown of tissue by exogenous agents, these can be treated with MP inhibitors. For example, they are effective as rattle snake bite antidote, as anti-vessicants, in treating allergic inflammation, septicemia and shock. In addition, they are useful as antiparasitics (e.g., in malaria) and antiinfectives. For example, they are thought to be useful in treating or preventing viral infection, including infection which would result in herpes, "cold" (e.g., rhinoviral infection), meningitis, hepatitis, HIV infection and AIDS.

MP inhibitors are also thought to be useful in treating Alzheimer's disease, amyotrophic lateral sclerosis (ALS), muscular dystrophy, complications resulting from or arising out of diabetes, especially those involving loss of tissue viability, coagulation, Graft vs. Host disease, leukemia, cachexia, anorexia, proteinuria, and perhaps regulation of hair growth.

For some diseases, conditions or disorders MP inhibition is contemplated to be a preferred method of treatment. Such diseases, conditions or disorders include, arthritis (including osteoarthritis and rheumitoid arthritis), cancer (especially the prevention or arrest of tumor growth and metastasis), ocular disorders (especially corneal ulceration, lack of corneal healing, macular degeneration, and pterygium), and gum disease (especially periodontal disease, and gingivitis)

Compounds preferred for, but not limited to, the treatment of arthritis (including osteoarthritis and rheumatoid arthritis) are those compounds that are selective for the matrix metalloproteases and the disintegrin metalloproteases.

Compounds preferred for, but not limited to, the treatment of cancer (especially the prevention or arrest of tumor growth and metastasis) are those compounds that preferentially inhibit gelatinases or type IV collagenases.

Compounds preferred for, but not limited to, the treatment of ocular disorders (especially corneal ulceration, lack of corneal healing, macular degeneration, and pterygium) are those compounds that broadly inhibit metalloproteases. Preferably these compounds are administered topically, more preferably as a drop or gel.

Compounds preferred for, but not limited to, the treatment of gum disease (especially periodontal disease, and gingivitis) are those compounds that preferentially inhibit collagenases.

Compositions:

The compositions of the invention comprise:
(a) a safe and effective amount of a compound of Formula (I); and
(b) a pharmaceutically-acceptable carrier.

As discussed above, numerous diseases are known to be mediated by excess or undesired metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences*, Mack Publishing Company, Easton, Pa., latest edition.

A "safe and effective amount" of a Formula (I) compound is an amount that is effective, to inhibit metalloproteases at the site(s) of activity, in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a human being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens"; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a human being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens"; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel" RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit" coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, is creams, solutions, gels and solids. These topical compositions preferably comprise a safe and effective amount, usually at least about 0.1% , and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emolients, emulsifiers, thickening agents, solvents and the like.

Methods of Administration:

This invention also provides methods of treating or preventing disorders associated with excess or undesired metalloprotease activity in a human or other animal subject, by administering a safe and effective amount of a Formula (I) compound to said subject. As used herein, a "disorder associated with excess or undesired metalloprotease activity" is any disorder characterized by degradation of matrix proteins. The methods of the invention are useful in treating disorders described above.

The Formula (I) compounds and compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The inhibitors of the invention can be targeted to specific locations where the metalloprotease is accumulated by using targeting ligands. For example, to focus the inhibitors to metalloprotease contained in a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases. Some bacterial metalloproteases may be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

Preparation and Use of Antibodies:

The invention compounds can also be utilized in immunization protocols to obtain antisera immunospecific for the invention compounds. As the invention compounds are relatively small, they are advantageously coupled to antigenically neutral carriers such as the conventionally used keyhole limpet hemocyanin (KLH) or serum albumin carriers. For those invention compounds having a carboxyl functionality, coupling to carrier can be done by methods generally known in the art. For example, the carboxyl residue can be reduced to an aldehyde and coupled to carrier through reaction with sidechain amino groups in protein-based carriers, optionally followed by reduction of imino linkage formed. The carboxyl residue can also be reacted with sidechain amino groups using condensing agents such as dicyclohexyl carbodiimide or other carbodiimide dehydrating agents.

Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures, now standard in the art, employing the invention compounds as antigens.

The antisera obtained can be used directly or monoclonal antibodies may be obtained by harvesting the peripheral blood lymphocytes or the spleen of the immunized animal and immortalizing the antibody-producing cells, followed by identifying the suitable antibody producers using standard immunoassay techniques.

The polyclonal or monoclonal preparations are then useful in monitoring therapy or prophylaxis regimens involving the compounds of the invention. Suitable samples such as those derived from blood, serum, urine, or saliva can be tested for the presence of the administered inhibitor at various times during the treatment protocol using standard immunoassay techniques which employ the antibody preparations of the invention.

The invention compounds can also be coupled to labels such as scintigraphic labels, e.g., technetium 99 or I-131, using standard coupling methods. The labeled compounds are administered to subjects to determine the locations of excess amounts of one or more metalloproteases in vivo. The ability of the inhibitors to selectively bind metalloprotease is thus taken advantage of to map the distribution of these enzymes in situ. The techniques can also be employed in histological procedures and the labeled invention compounds can be used in competitive immunoassays.

The following non-limiting examples illustrate the compounds, compositions, and uses invention.

EXAMPLES

Compounds are analyzed using $^1$H and $^{13}$C NMR, Elemental analysis, mass spectra and/or IR spectra, as appropriate.

Typically tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merk) as appropriate. Thin layer chromatography analysis (TLC) is performed on glass mounted silica gel plates (200–300 mesh; Baker) and visualized with UV or 5% phosphomolybdic acid in EtOH.

Examples 1–25

The following chart shows the structure of compounds made according to the description in Examples 1–19 described below:

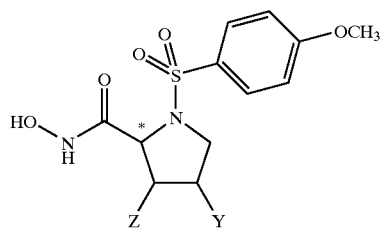

| Example | *(configuration) | Y | Z |
|---|---|---|---|
| 1 | d | a-OH | H |
| 2 | d | b-OH | H |
| 3 | l | a-OH | H |
| 4 | l | b-OH | H |
| 5 | d | b-OMe | H |
| 6 | d | b-(2-benzathiazole) | H |
| 7 | d | a-(2-benzathiazole) | H |
| 8 | d | b-2(3N-methyl-imidazole) | H |
| 9 | d | a-2(3N-methyl-imidazole) | H |
| 10 | d | b-OPh | H |
| 11 | d | b-O($C_6H_4$)$OCH_2$Ph | H |
| 12 | d | b-O(2-($C_6H_4$)NHPh) | H |
| 13 | d | b-O(3-Pyridyl) | H |
| 14 | d | b-SPh | H |
| 15 | d | b-S(4-$C_6H_4$OMe) | H |
| 16 | d | b-S(3-$C_6H_4$OMe) | H |
| 17 | d | a-$OCH_2OCH_2CH_3$ | H |
| 18 | d | a-$OCH_2OCH_2$Ph | H |
| 19 | d | a-$OCH_2OCH_2CH_3OCH_3$ | H |
| 20 | d | b-SH | H |
| 21 | racemic | H | phenyl |
| 22 | d | a-OH, b-Et | H |
| 23 | d | a-OH, b-Ph | H |
| 24 | d | b-O(4-$C_6H_4$-Octyl) | H |
| 25 | d | a-OH | gem-$(CH_3)_2$ |

Ph—phenyl
Me = methyl
$C_6H_4$—phenyl diradical

Example 1 a. (1N)-4-Methoxyphenylsulfonyl-(2R)-carbomethoxy-4R-hydroxy-pyrrolidine: cis-Hydroxy-D-proline (50 g, 0.38 mole) is dissolved in water:dioxane (1:1, 300 mL) with triethylamine (135 mL, 0.96 mole). 4-Methoxyphenylsulfonyl chloride (87 g, 0.42 mole) is added along with 2,6-dimethylaminopyridine (4.6 g, 0.038 mole) and the mixture is stirred 14 hr. at room temperature. The mixture is then concentrated and diluted with EtOAc. Layers are separated and the organic layer is washed 2× with 1N HCl, 1× with brine, dried over $MgSO_4$, filtered and evaporated to give 83 g of solid material which is dissolved in MeOH (500 mL). Thionyl chloride (50 mL) is added dropwise and the resulting mixture stirred for 14 hr. The mixture is then evaporated to dryness and triturated with $CHCl_3$ to give a white solid which is sufficiently pure to carry forward without purification. CI$^+$ MS: m/z (rel intensity) 316 (M$^+$+H, 100), 256 (30), 146 (45).

b. (1N)-4-Methoxyphenylsulfonyl-(2R)-N-hydroxycarboxamido-(4S)-hydroxypyrrolidine: The starting methylester 1a (361 mg, 1.15 mmole) is taken in 1 mL of methanol, treated with $NH_2OK$ (1.45 mL, 0.86 M in methanol, solution prepared as described in Fieser and Fieser, Vol 1, p 478) and stirred overnight. The following morning the material is concentrated and partitioned between EtOAc and 1N HCl. The organic layer is washed with brine, dried over $MgSO_4$, filtered and evaporated to give crude material which is recrystallized from hex:EtOAc at −4° C. to give the desired white solid and recovered oil. ESI MS: m/z (rel intensity) 317 (M+H$^+$, 100), 334 (M+NH$_4^+$, 20), 339 (M+Na$^+$, 35).

Example 2 a. (1N)-4-Methoxyphenylsulfonyl-(2R)-carbomethoxy-(4S)-benzoyloxypyrrolidine: The alcohol 1a (780 mg, 2.48 mmole) is dissolved in 5 mL of methylene chloride. Benzoic acid (604 mg, 4.95 mmole) and triphenyl phosphine (779 mg, 2.98 mmole) are then added, followed by diethyl azodicarboxylate (429 mL, 2.73 mmole). After 3 hrs, the reaction mixture is filtered and silica gel is added to the filtrate to adsorb the solutes and the mixture is concentrated to dryness. The resulting solid mixture is poured onto the top of a flash silica column which is eluted with hex:EtOAc (1:1 to 0:1) to give the desired product as a white solid. CI$^+$ MS: m/z (rel intensity) 420.0 (M$^+$+H, 100), 250.1 (95), 126.0 (45).

b. (1N)-4-Methoxyphenylsulfonyl-(2R)-N-hydroxycarboxamido-(4S)-hydroxypyrrolidine: The methyl-benzyl diester 2a (175 g, 0.418 mmole) is taken in 2.5 mL of methanol, treated with $NH_2OK$ (0.48 mL, 0.86 M in methanol, solution prepared as described in Fieser and Fieser, Vol 1, p 478) and stirred overnight. The following morning, dry silica (1 mL) is added to the mixture and the solvent removed under vacuum. The dry silica is poured on the top of a flash silica gel column which is subsequently eluted with EtOAc:MeOH:$HCO_2$H (90:9:1) to give a white solid which is then recrystallized from hexane:EtOAc (1:5) to give white crystals. ESI MS: m/z (rel intensity) 317.1 (M$^+$+H, 100), 339.1 (M$^+$+Na, 20).

Example 3 a. (1N)-4-Methoxyphenylsulfonyl-(2S)-carbomethoxy-(4R)-hydroxypyrrolidine: To a solution of trans-4-hydroxy-L-proline methyl ester (2.0 g, 11.0 mmol) in 10 mL DMF is added 2 mL N-methylmorpholine and 4-methoxybenzenesulfonyl chloride and is stirred for 1 hr. The solution is then partitioned between EtOAc and water, washed with 1 N HCl, $NaHCO_3$, NaCl, and dried over $MgSO_4$. The crude product is then chromatographed over silica with EtOAc to give the title compound. CI$^+$ MS: m/z (rel intensity) 316 (100, M$^+$+H).

b. (1N)-4-Methoxyphenylsulfonyl-(2S)-N-hydroxycarboxanido-(4R)-hydroxypyrrolidine: The starting ester 3a (500 mg, 1.6 mmol) is added to $NH_2OK$ (1.9 mL, 1 eq in MeOH, prepared according to Fieser and Fieser, Vol 1, p 478) and stirred for 15 hr. The solvent is evaporated and the residue is dissolved in 1N HCl and extracted with EtOAc. The organic layer is dried over $MgSO_4$, evaporated and the residue is recrystallized from EtOAc:Hexanes to give the title compound. ESI MS: m/z (rel intensity) 317 (100, M$^+$+H), 256 (70).

Example 4 a. (1N)-4-Methoxyphenylsulfonyl-(2S)-carbomethoxy-(4S)-hydroxy-pyrrolidine: To a solution of cis-4-hydroxy-L-proline methyl ester (2.0 g, 11.0 mmol) in 10 mL DMF is added 2 mL N-methylmorpholine and 4-methoxybenzenesulfonyl chloride and is stirred for 1 hr.

The solution is then partitioned between EtOAc and water, washed with 1 N HCl, NaHCO$_3$, NaCl, and dried over MgSO$_4$. The crude product is then chromatographed over silica with EtOAc to give the title compound. CI$^+$ MS: m/z (rel intensity) 316 (100, M$^+$+H).

b. (1N)-4-Methoxyphenylsulfonyl-(2S)-N-hydroxycarboxanido-(4S)-hydroxy-pyrrolidine: The starting ester 4a (500 mg, 1.6 mmol) is added to NH$_2$OK (1.9 mL, 1 eq in MeOH, prepared according to Fieser and Fieser, Vol 1, p 478) and stirred for 15 hr. The solvent is evaporated and the residue is dissolved in 1N HCl and extracted with EtOAc. The organic layer is dried over MgSO$_4$, evaporated and the residue is recrystallized from EtOAc:Hexanes to give the title compound. ESI MS: m/z (rel intensity) 317 (100, M$^+$+H), 256 (70).

Example 5 a. (1N)-4-Methoxyphenylsulfonyl-(2R)-carboxy-(4S)-hydroxy-pyrrolidine: The diester 2a (10 g, 24 mmole) is dissolved in water:dioxane (1:10, 50 mL) and stirred overnight in the presence of lithium hydroxide monohydrate (5 g, 120 mmole). The mixture is acidified with 1N HCl and extracted with EtOAc, washed with brine, dried over MgSO$_4$, filtered and evaporated to give solid material which is recrystallized from EtOAc:hexanes to give the title compound as a white solid. ESI MS: m/z (rel intensity) 302 (M$^+$+H, 100), 318 (M$^+$+NH$_3$, 30).

b. (1N)-4-Methoxyphenylsulfonyl-(2R)-carbomethoxy-(4S)-methoxy-pyrrolidine: The carboxylic acid 5a (4.0 g, 13.2 mmol) is stirred in THF at room temperature and then sodium hydride (1.58 g, 39.6 mmol, 3 equiv, 60% in oil) is slowly added. After hydrogen gas evolution had ceased, methyl iodide (5.52 g, 39.6 mmol, 3 equiv) is added to the reaction mixture. The resulting solution is stirred at room temperature for 1 hour. The reaction mixture is quenched by the addition of water and then extracted with EtOAc. The organic extracts are concentrated to an oil and then methanol and 3 drops of conc. HCl are added. The solution is then heated to reflux for 24 hours. The solvent is removed and the product is purified by silica gel chromatography (1/1 hexane/EtOAc followed by 100% EtOAc) to afford the desired methyl ester as a white crystalline solid. CI$^+$ MS: m/z (rel intensity) 330 (M$^+$, 100).

c. (1N)-4-Methoxyphenysulfonyl-(2R)-N-hydroxycarboxamido-(4S)-methoxypyrrolidine: The ester 5b (0.50 g, 1.52 mmol) is taken in 2 mL of methanol, treated with NH$_2$OK (2.5 mL, 0.86 M in methanol, solution prepared as described in Fieser and Fieser, Vol 1, p 478) and stirred overnight. The solution is poured into water and acidified to pH~2. The resulting solution is extracted with CH$_2$Cl$_2$, dried (Na$_2$SO$_4$) and concentrated to a white solid. Purification of the resulting solid is accomplished by recrystallization from EtOAc:hexane (3:1) to afford the desired product as a white crystalline solid. ESI MS: m/z (rel intensity) 331.0 (M+H$^+$, 100), 348.0 (M+NH$_4$$^+$, 85), 353.0 (M+Na$^+$, 45).

Example 6 a. (1N)-4-Methoxyphenylsulfonamido-(2R)-carbomethoxy-(4R)-trifluoromethanesulfonyl-pyrrolidine: The starting alcohol 1a (221 mg, 0.702 mmole) is taken in dry CH$_2$Cl$_2$ under argon and cooled to 0° C. 2,6-Lutidine (326 mL, 2.81 mmoles) is added via slow syringe followed by slow syringe addition of trifluoromethanesulfonyl anhydride (153 mL, 0.912 mmole) and the resulting yellow mixture is 1 hr at 0° C. and then partitioned between water and EtOAc. The organic layer is dried over MgSO$_4$, filtered and evaporated. The crude residue is chromatogaphed over flash silica with hexane:EtOAc (4:1 to 1:1) to give the desired off-white solid. CI$^+$ MS: m/z (rel intensity) 411 (M+NH$_4$$^+$, 25) 394 (M$^+$+H, 21), 224 (82), 155 (23), 128 (100).

b. (1N)-4-Methoxyphenylsulfonyl-(2R)-carbomethoxy-(4S)-(2-mercapto-benzothiazolyl)-pyrrolidine: The triflate 6a (145 mg, 0.353 mmole) is dissolved in methylene chloride (1 mL) under argon and 2,6-lutidine (61 mL, 0.529 mmole) is added via syringe followed by 2-mercapto-benzothiazole (65 mg, 0.388 mmole). After 1 hr., silica gel (1.5 mL) is added to the mixture which is then evaporated to dryness. The resulting solid mixture is then added to the top of a flash silica column which is then eluted with hexane:EtOAc (1:1 to 1:5) to give the pure title compound as a clear oil. CI$^+$ MS: m/z (rel intensity) 465 (M$^+$+H, 10), 300 (38), 240 (13), 168 (21), 150 (33), 136 (100).

c. (1N)-4-Methoxyphenylsulfonyl-(2R)-N-hydroxycarboxamido-(4S)-(2-mercapto-benzothiazolyl)-pyrrolidine: A 1.76M solution of potassium hydroxyl amine in methanol is prepared. The 1.76M solution (0.4 mL, 0.711 mmoles) is added directly to the methyl ester 6b (0.165 g, 0.356 mmoles) and the reaction mixture stirred overnight. The solution is acidified with 1N HCl, then extracted 3 times with ethyl acetate, dried with magnesium sulfate, filtered and evaporated. Chromatography is performed on silica gel using ethyl acetate:hexane:formic acid (1:1:0.1) to give the title compound. ESI MS: m/z (rel intensity) 466.0 (M$^+$+H, 100), 408.2 (M$^+$+Na, 20).

Example 7 a. (1N)-4-Methoxyphenylsulfonyl-(2R)-carbomethoxy-(4S)-hydroxy-pyrrolidine: The acid 5a (4 g, 9.55 mmole) is dissolved in methanol (50 mL), treated with thionyl chloride (3 mL) and stirred overnight. The mixture is then evaporated to dryness and recrystallized from EtOAc:hexanes to give the title compound as a white solid. CI$^+$ MS: m/z (rel intensity) 316 (M$^+$+H, 100), 256 (60), 158 (25), 146 (30).

b. (1N)-4-Methoxyphenylsulfonyl-(2R)-N-hydroxycarboxamido-(4R)-(2-mercapto-benzothiazolyl)-pyrrolidine: The starting alcohol 7a (323 mg, 1.03 mmole) is taken in 4 mL of CH$_2$Cl$_2$ and to this mixture is added triphenylphosphene (351 mg, 1.35 mmole), 2-mercaptobenzothiazole (189 mg, 1.13 mg), and diethyldiazadicarboxylate (195 mM, 1.24 mmole) and the mixture is stirred for 0.5 hr. at which time 5 mL of silica gel is added to the mixture which is then concentrated to dryness. The dry residue is poured onto the top of a flash silica column and eluted with hexane:EtOAc (4:1 to 1:4) to give a clear oil. CI$^+$ MS: m/z (rel intensity) 465 (M$^+$+H, 5), 300 (20), 150 (25), 136 (100), 128 (25).

c. (1N)-4-Methoxyphenylsulfonyl-(2R)-N-hydroxycarboxamido-(4R)-(2-mercaptobenzo-thiazolyl)-pyrrolidine: The methyl ester 7b (372 g, 0.802 mmole) is taken in 1.5 mL of methanol, treated with NH$_2$OK (1.4 mL, 0.86 M in methanol, solution prepared as described in Fieser and Fieser, Vol 1, p 478) and stirred overnight. The following morning, dry silica (1.5 mL) is added to the mixture and the solvent removed under vacuum. The dry silica is poured on the top of a flash silica gel column which is subsequently eluted with hexane:EtOAc (1:2) to remove impurities and then EtOAc:MeOH (9:1). The resulting product is recrystallized from chloroform to give white crystals. ESI MS: m/z (rel intensity) 466.1 (M$^+$+H, 100), 488.0 (M$^+$+Na, 12).

Example 8 a. (1N)-4-Methoxyphenylsulfonyl-(2R)-carbomethoxy-(4S)-[(1N)-methyl-2-mercapto-imidazyl]-pyrrolidine: The alcohol 1a (700 mg, 2.22 mmole) is dissolved in 12 mL of methylene chloride. 2-Mercapto-1-methylimidazole (304 mg, 2.66 mmole) and triphenyl phosphine (873 mg, 3.33 mmole) are then added, followed by diethyl azodicarboxylate (420 mL, 2.66 mmole). After 3 hrs, the reaction mixture is filtered and silica gel is added to the filtrate to adsorb the solutes and the mixture is concentrated to dryness. The resulting solid mixture is poured onto the top of a flash silica column which is eluted with hex:EtOAc (1:1 to 0:1) to give the desired product as a white solid. CI$^+$ MS: m/z (rel intensity) 412 (M$^+$+H, 100), 242 (5), 115 (28).

b. (1N)-4-Methoxyphenylsulfonyl-(2R)-N-hydroxycarboxamido-(4S)-[(1N)-methyl-2-mercaptoimidazyl]-pyrrolidine: The ester 8a (500 mg, 1.22 mmole) is taken in 1 mL of methanol, treated with NH$_2$OK (2.11 mL, 0.86 M in methanol, solution prepared as described in Fieser and Fieser, Vol 1, p 478) and stirred overnight. The following morning, dry silica (2 mL) is added to the mixture and the solvent removed under vacuum. The dry silica is poured on the top of a flash silica gel column which is subsequently eluted with hexane:EtOAc (1:1 to 0:1) followed by EtOAc:MeOH:NH$_4$OH (9:1:0.1) to give a white solid. ESI MS: m/z (rel intensity) 413 (M$^+$+H, 100), 435 (M$^+$+Na, 20).

Example 9 a. (1N)-4-Methoxyphenylsulfonyl-(2R)-carbomethoxy-(4R)-[(1N)-methyl-2-mercapto-imidazyl]-pyrrolidine: The alcohol 7a (700 mg, 2.22 mmole) is dissolved in 12 mL of methylene chloride. 2-Mercapto-1-methylimidazole (304 mg, 2.66 mmole) and triphenyl phosphine (873 mg, 3.33 mmole) are then added, followed by diethyl azodicarboxylate (420 mL, 2.66 mmole). After 3 hrs, the reaction mixture is filtered and silica gel is added to the filtrate to adsorb the solutes and the mixture is concentrated to dryness. The resulting solid mixture is poured onto the top of a flash silica column which is eluted with hex:EtOAc (1:1 to 0:1) to give the desired product as a white solid. CI$^+$ MS: m/z (rel intensity) 412 (M$^+$+H, 100), 242 (5), 115 (28).

b. (1N)-4-Methoxyphenylsulfonyl-(2R)-N-hydroxycarboxado-(4R)-[(1N)-methyl-2-mercaptoimidazyl]-pyrrolidine: The ester 9a (500 mg, 1.22 mmole) is taken in 5 mL of methanol, treated with NH$_2$OK (2.11 mL, 0.86 M in methanol, solution prepared as described in Fieser and Fieser, Vol 1, p 478) and stirred overnight. The following morning, dry silica (2 mL) is added to the mixture and the solvent removed under vacuum. The dry silica is poured on the top of a flash silica gel column which is subsequently eluted with hexane:EtOAc (1:1 to 0:1) to give a white solid. ESI MS: m/z (rel intensity) 413.0 (M$^+$+H, 100), 435.0 (M$^+$+Na, 20).

Example 10 a. (1N)-4-Methoxyphenylsulfonyl-(2R)-carbomethoxy-(4S)-phenoxy-pyrrolidine: The alcohol 1a (1.3 g, 4.12 mmole) is dissolved in 3 mL of methylene chloride. Phenol (0.8 g, 8.24 mmole) and triphenyl phosphine (2.16 g, 8.24 mmole) are then added, followed by diethyl azodicarboxylate (1.2 mL, 7.84 mmole). After 3 hrs, the reaction mixture is filtered and concentrated to an oil, which is purified on silica gel using ethyl acetate:hexane:methylene chloride (1:3:1) to give the desired product as an oil. CI$^+$ MS: m/z (rel intensity) 409 (100, M$^+$+NH$_3$), 392 (72, M$^+$+H).

b. (1N)-4-Methoxyphenylsulfonyl-(2R)-N-hydroxycarboxamido-(4S)-phenoxypyrrolidine: The methyl ester 10a (0.6 g, 1.53 mmole) is taken in 3 mL of methanol, treated with NH$_2$OK (5 mL, 1.7 M in methanol, solution prepared as described in Fieser and Fieser, Vol 1, p 478) and stirred overnight. The following morning, dry silica (1.5 mL) is added to the mixture and the solvent removed under vacuum. The dry silica is poured on the top of a flash silica gel column which is subsequently eluted with formic acid:EtOAc (0:1 to 3:97) to give 0.36 g of white foamy solid, which is recrystallized from hexane:EtOAc to give the desired product. ESI MS: m/z (rel intensity) 415 (38, M$^+$+Na), 410 (10, M$^+$+NH$_4$), 393 (100, M$^+$+H).

Example 11 a. (1N)-4-Methoxyphenylsulfonyl-(2R)-carbomethoxy-(4S)-[(4-benzyloxy)-phenoxy]-pyrrolidine: Triphenylphosphine (2.5 g, 9.51 mmole) is dissolved in 20 mL of THF. Diethyl azodicarboxylate (1.9 mL, 9.51 mmole) is added dropwise at 0° C. After 30 min with stirring, a solution of 4-(benzyloxy)phenol (2.38 g, 11.9 mmole) and the alcohol 1a (1.5 g, 4.76 mmole) in 15 mL of THF is added dropwise. The reaction is stirred at 0° C. for 30 min., room temperature overnight and concentrated to an oil. The crude product is purified by flash chromatography (hexane/EtOAc, 4:1 to 1:1) on silica gel to give the desired product. CI$^+$ MS: m/z (rel intensity) 498 (100, M$^+$+H), 328 (24).

b. (1N)-4-Methoxyphenylsulfonyl-(2R)-N-hydroxycarboxamido-(4S)-(4-benzyloxy)-phenoxypyrrolidine: The methyl ester 11a (0.7 g, 1.4 mmole) is taken in 1 mL of methanol, treated with NH$_2$OK (8 ml, 1.7 M in methanol, solution prepared as described in Fieser and Fieser, Vol 1, p 478) and stirred for 3 hr. Silica (1.5 mL) is added to the mixture and the solvent is removed under vacuum. The dry silica is poured on the top of a flash silica gel column which is subsequently eluted with hexane:EtOAc (1:1) to EtOAc:CH$_3$OH (1:0 to 1:1) to give the desired product as a white foamy solid. ESI MS: m/z (rel intensity) 521 (30, M$^+$+Na), 516 (14, M$^+$+NH$_4$), 499(100, M$^+$+H).

Example 12 a. (1N)-4-Methoxyphenylsulfonyl-(2R)-carbomethoxy-(4S)-(3-N-phenyl-amino)-phenoxylpyrrolidine: Triphenylphosphine (2.5 g, 9.52 mmole) is dissolved in 20 mL of THF. Diethyl azodicarboxylate (1.95 mL, 9.52 mmole) is added dropwise at 0° C. After 30 min with stirring, a solution of 3-hydroxydiphenylamine (2.2 g, 11.9 mmole) and the alcohol 1a (1.5 g, 4.76 mmole) in 15 mL of THF is added dropwise. The reaction is stirred at 0° C. for 30 min., room temperature for 2 hr and concentrated to an oil. The crude product is purified by flash chromatography (hexane/EtOAc, 7:3 to 1:1) on silica gel to give the desired product. ESI MS: m/z (rel intensity) 505 (8, M$^+$+Na), 483 (100, M$^+$+H).

b. (1N)-4-Methoxyphenylsulfonyl-(2R)-N-hydroxycarboxamido-(4S)-(3-N-phenylamino)- phenoxylpyrrolidine: The methyl ester 12a (0.68 g, 1.38 mmole) is taken in 2 mL of methanol, treated with NH$_2$OK (6 mL, 1.7 M in methanol, solution prepared as described in Fieser and Fieser, Vol 1, p 478) and stirred overnight. The following morning, dry silica (1.5 mL) is added to the mixture and the solvent is removed under vacuum. The dry silica is poured on the top of a flash silica gel column which is subsequently eluted with EtOAc:CH$_3$OH (1:0 to 9:1) to give the desired product as a white foamy solid. ESI MS: m/z (rel intensity) 506 (36, M$^+$+Na), 484 (100, M$^+$+H).

Example 13 a. (1N)-4-Methoxyphenylsulfonyl-(2R)-carbomethoxy-(4S)-(3-pyridinoxy)-pyrrolidine: Triphenylphosphine (2.42 g, 9.2 mmole) is dissolved in 20 mL of THF. Diethyl azodicarboxylate (1.81 mL, 9.2 mmole) is added dropwise at 0° C. After 30 min with stirring, a solution of 3-hydroxypyridine (1.32 g, 13.83 mmole) and the alcohol 1a (1.5 g, 4.61 mmole) in 15 mL of THF is added dropwise. The reaction is stirred at 0° C. for 30 min., room temperature for 2 hr and concentrated to an oil. The crude product is purified by flash chromatography (hexane/EtOAc: 1/1 to EtOAc) on silica gel to give the desired product. CI$^+$ MS: m/z (rel intensity) 393 (100, M$^+$+H), 279 (88), 223 (70).

b. (1N)-4-Methoxyphenylsulfonyl-(2R)-N-hydroxycarboxamido-(4S)-phenoxypyrrolidine: The methyl ester 13a (0.18 g, 0.46 mmole) is taken in 1 mL of methanol, treated with NH$_2$OK (0.5 ml, 1.7 M in methanol, solution prepared as described in Fieser and Fieser, Vol 1, p 478) and stirred overnight. The following morning, dry silica (1.5 mL) is added to the mixture and the solvent is removed under vacuum. The dry silica is poured on the top of a flash silica gel column which is subsequently eluted with EtOAc:CH$_3$OH (1:0 to 1:1) to give a white foamy solid which is crystallized from methylene chloride to give the desired product as a white solid. ESI MS: m/z (rel intensity) 432 (10, M$^+$+K), 416 (8, M$^+$+Na), 394 (100, M$^+$+H).

Example 14 a. (1N)-4-Methoxyphenylsulfonyl-(2R)-carbomethoxy-(4S)-mercaptophenylpyrrolidine: The alcohol 1a (200 mg, 0.634 mmole) is dissolved in 2 mL of methylene chloride. Thiophenol (78 mL, 0.671 mmole) and triphenyl phosphine (250 mg, 0.951 mmole) are then added, followed by diethyl azodicarboxylate (120 mL, 0.761 mmole). After 3 hrs, the reaction mixture is filtered and silica gel is added to the filtrate to adsorb the solutes and the mixture is concentrated to dryness. The resulting solid mixture is poured onto the top of a flash silica column which is eluted with hex:EtOAc (1:1 to 0:1) to give the desired white solid. CI$^+$ MS: m/z (rel intensity) 408 (M$^+$+H, 15), 238 (100), 128 (99), 109 (93).

b. (1N)-4-Methoxyphenylsulfonamido-(2R)-N-hydroxycarboxamido-(4S)-mercaptophenylpyrrolidine: The starting methylester 14a (169 mg, 0.415 mmole) is taken in 1 mL of methanol, treated with NH$_2$OK (0.725 mL, 0.86 M in methanol, solution prepared as described in Fieser and Fieser, Vol 1, p 478) and stirred overnight. The following morning, dry silica (1.5 mL) is added to the mixture and the solvent removed under vacuum. The dry silica is poured on the top of a flash silica gel column which is subsequently eluted with hexane:EtOAc (1:1 to 0:1) and then with EtOAc:MeOH:NH$_4$OH (9:1:0.1) to give a white solid. ESI MS: m/z (rel intensity) 409.2 (M$^+$+H, 100), 426.2 (M$^+$+NH$_4$, 12), 431.1 (M$^+$+Na, 25).

Example 15 a. (1N)-4-Methoxyphenylsulfonamido-(2R)-carbomethoxy-(4R)-methane-sulfonyl-pyrrolidine: The starting alcohol 1a (17.9 g, 57 mmole) is taken in dry CH$_2$Cl$_2$ (100 mL) in the presence of Et$_3$N (25 mL) at room temperature. Methanesulfonyl chloride (4.87 mL, 63 mmole) is added dropwise and the resulting mixture is stirred overnight and the following morning the mixture is partioned between water and EtOAc. The organic layer is washed with brine, dried over MgSO$_4$, filtered and evaporated. The resulting solid is recrystallized from EtOAc:hexanes to give the title compound as white prisms. CI$^+$ MS: m/z (rel intensity) 411 (M+NH$_4$$^+$, 25) 394 (M$^+$+H, 21), 224 (82), 155 (23), 128 (100).

b. (1N)-4-Methoxyphenylsulfonyl-(2R)-carbomethoxy-(4S)-(4-methoxy-mercaptophenyl)-pyrrolidine: The starting mesylate 15a (267 mg, 0.68 mmole) and 4-methoxythiophenol (88 mL, 0.713 mmole) are taken in THF (4 mL) at room temperature under argon and $^t$butoxide (78 mg, 0.713 mmole) is added. The mixture is stirred for 1 hr and then partitioned between EtOAc and 1N HCl. The organic layer is washed with brine, dried over MgSO$_4$, filtered and evaporated to give 354 mg of residue which is then chromatographed over flash silica with hexane:EtOAc (8:1 to 2:1) to give the title compound as a clear oil. CI$^+$ MS: m/z (rel intensity) 438 (M$^+$+H, 50), 268 (100), 208 (21), 155 (81), 128 (79), 109 (45).

c. (1N)-4-Methoxyphenylsulfonyl-(2R)-N-hydroxycarboxamido-(4S)-(4-methoxyphenyl-thioloxy)-pyrrolidine: The starting methylester 15b (129 mg, 0.295 mmole) is taken in 1 mL of methanol, treated with NH$_2$OK (0.85 mL, 0.86 M in methanol, solution prepared as described in Fieser and Fieser, Vol 1, p 478) and stirred overnight. The following morning, dry silica (1.5 mL) is added to the mixture and the solvent removed under vacuum. The dry silica is poured on the top of a flash silica gel column which is subsequently eluted with hexane:EtOAc (1:2 to 0:1) to give a clear glass which is puffed into a foamy solid by slight heating under vacuum. ESI MS: m/z (rel intensity) 439 (M$^+$+H, 100), 456 (M$^+$+NH$_3$, 30).

Example 16 a. (1N)-4-Methoxyphenylsulfonyl-(2R)-carbomethoxy-(4S)-(3-methoxy-mercaptophenyl)-pyrrolidine: The starting mesylate 15a (267 mg, 0.68 mmole) and 3-methoxythiophenol (88 mL, 0.713 mmole) are taken in THF (4 mL) at room temperature under argon and $^t$butoxide (78 mg, 0.713 mmole) is added. The mixture is stirred for 1 hr and then partitioned between EtOAc and 1N HCl. The organic layer is washed with brine, dried over MgSO$_4$, filtered and evaporated to give a residue which is then chromatographed over flash silica with hexane:EtOAc (8:1 to 2:1) to give the title compound as a clear oil. CI$^+$ MS: m/z (rel intensity) 438.0 (M+H$^+$, 17), 268.0 (100), 155 (65).

b. (1N)-4-Methoxyphenylsulfonyl-(2R)-N-hydroxycarboxamido-(4S)-(3-methoxy-mercaptophenyl)-pyrrolidine: The starting methylester 16a (1.58 mg, 0.361 mmole) is taken in 5 mL of methanol, treated with NH$_2$OK (0.624 mL, 0.86 M in methanol, solution prepared as described in Fieser and Fieser, Vol 1, p 478) and stirred overnight. The following morning, dry silica (2 mL) is added to the mixture and the solvent removed under vacuum. The dry silica is poured on the top of a flash silica gel column which is subsequently eluted with hexane:EtOAc (1:1 to 0:1) then with EtOAc:MeOH:NH$_4$OH (9:1:0.1) to give a white solid. ESI MS: m/z (rel intensity) 439 (M$^+$+H, 10), 456.0 (M$^+$+NH$_4^+$, 40), 461.0 (M$^+$+Na$^+$, 27).

Example 17 a. (1N)-4-Methoxyphenylsulfonyl-(2R)-carbomethoxy-(4R)-ethyloxymethoxy-pyrrolidine: Chloroethylmethylether (0.884 mL, 9.54 mmole) was added dropwise to a stirred solution of the methylester 1a (1.00 g, 3.18 mmole) in CH$_2$Cl$_2$ (12 mL) and DIPEA (0.830 mL) and stirred for 16 hrs. Additional CH$_2$Cl$_2$ was added and the mixture was washed with saturated NaHSO$_4$, dried over sodium sulfate and the solvent removed under vacuum. The dried material was purified over a silica column eluting first with hexane:EtOAc (8:2), followed with hexane:EtOAc (1:1) then with EtOAc to give a colorless oil. ESI MS: m/z (rel intensity) 374.02 (M$^+$+H, 100), 391.03 (M$^+$+NH$_3$, 70).

b. (1N)-4-Methoxyphenylsulfonyl-(2R)-carbomethoxy-(4R)-ethyloxymethoxy-pyrrolidine: The starting methyl ester 17a (1.13 g, 3.03 mmole) is taken in 4 mL of methanol tetrahydrofuran (1:1), and treated with NH$_2$OK (4 mL, 1.25M in methanol) and stirred overnight. The following morning, dry silica (2.5 mL) is added to the mixture and the solvent removed under vacuum. The dry silica is poured on top of a flash silica column which is subsequently eluted with ethyl acetate followed with ethyl acetate:methanol (8:2) to give a clear glass which is puffed to a foamy solid by slight heating under vacuum. The product was recrystallized from cold EtOAc:hexane to give white powder. ESI MS: m/z (rel intensity) 374.02 (M$^+$+H, 100), 391.03 (M$^+$+NH$_3$, 70).

Example 18 a. (1N)-4-Methoxyphenylsulfonyl-(2R)-carbomethoxy-(4R)-benxyloxy-methoxy-pyrrolidine: Benzylchloromethylether (2.25 g, 9.54 mmole) is added dropwise to a stirred solution of the methylester 1a (1.00 g, 3.18 mmole) in CH$_2$Cl$_2$ (12 mL) and DIPEA (0.830 mL, 4.77 mmole) and stirred for four days. Additional CH$_2$Cl$_2$ is added and the mixture washed with saturated NaH$_2$SO$_4$, dried over sodium sulfate and the solvent removed under vacuum. The dried material is purified over a silica column eluting first with hexane, then with hexane:EtOAc (7:3) to give a colorless oil.
ESI MS: m/z (rel intensity) 436.07 (M$^+$+H, 100), 453.09 (M$^+$+NH$_3$, 70).

b. (1N)-4-Methoxyphenylsulfonyl-(2R)-N-hydroxycarboxamido-(4R)-benxyl-oxymethoxy-pyrrolidine: The starting methyl ester 18a (1.00 g, 2.29 mmole) is taken in 2 mL of methanol/tetrahydrofuran (1:1), and treated with NH$_2$OK (2 ml, 1.25M in methanol) and stirred overnight. The following morning, dry silica (1.5 ml) is added to the mixture and the solvent removed under vacuum. The dry silica is poured on top of a flash silica column which is subsequently eluted with hexane:ethyl acetate (7:3) followed with ethyl acetate to give a clear glass which is dried to a foamy solid by slight heating under vacuum. The product was recrystallized from cold methanol to give white powder. ESI MS: m/z (rel intensity) 436.98 (M$^+$+H, 100), 453.97 (M$^+$+NH$_3$, 30).

Example 19 a. (1N)-4-Methoxyphenylsulfonyl-(2R)-carbomethoxy-(4R)-(2-methoxyethyl-oxy)-methoxypyrrolidine: MEM chloride (1.09 mL, 9.54 mmole) is added dropwise to a stirred solution of the alcohol 1a (1.00 g, 3.18 mmole) in CH$_2$Cl$_2$ (12 mL) and DIPEA (0.830 mL) and stirred for 16 hrs. Additional CH$_2$Cl$_2$ is added and the mixture is washed with saturated NaH$_2$SO$_4$, dried over sodium sulfate and the solvent removed under vacuum. The dried material was purified over a silica column eluting first with hexane:EtOAc (1:1) to give a colorless oil. ESI MS: m/z (rel intensity) 403.99 (M$^+$+H, 70), 421.01 (M$^+$+NH$_3$, 100).

b. (1N)-4-Methoxyphenylsulfonyl-(2R)-carbomethoxy-(4R)-(2-methoxyethyl-oxy)-methoxypyrrolidine: The starting methyl ester 19 (450 mg, 1.12 mmole) is taken in 2 mL of methanol:tetrahydrofuran (1:1), and treated with NH$_2$OK (2 mL, 1.25M in methanol) and stirred overnight. The following morning, dry silica (1.5 mL) is added to the mixture and the solvent removed under vacuum. The dry silica is poured on top of a flash silica column which is subsequently eluted with EtOAc followed with ethyl acetate:methanol (8:2) to give a clear glass which is puffed to a foamy solid by slight heating under vacuum. The product is was recrystallized from cold EtOAc:hexane to give white powder. ESI MS: m/z (rel intensity) 405.05 (M$^+$+H, 100), 422.01 (M$^+$+NH$_3$, 20).

Example 20 a. (1N)-4-Methoxyphenylsulfonyl-(2R)-carbomethoxy-(4S)-thioacetoxyl-pyrrolidine: Triphenylphosphine (0.9 g, 3.42 mmole) is dissolved in 12 mL of THF. Diethyl azodicarboxylate (0.54 mL, 3.42 mmole) is added dropwise at 0° C. After 30 min with stirring, a solution of thioacetic acid (0.4 mL, 5.13 mmole) and the alcohol 1a (0.54 g, 1.71 mmole) in 10 mL of THF is added dropwise. The reaction is stirred at 0° C. for 30 min., room temperature for 2 hr and concentrated to an oil. The crude material is purified by flash chromatography (CH$_2$Cl$_2$:hexane (1:1) to CH$_2$Cl$_2$:EtOAc; (50:1) to CH$_2$Cl$_2$:EtOAc; 25:1) on silica gel to give the desired product. ESI MS: m/z (rel intensity) 391 (100, M$^+$+NH$_3$), 374 (65, M$^+$+H).

b. (1N)-4-Methoxyphenylsulfonyl-(2R)-hydroxycarboxamido-(4S)-thio-pyrrolidine: The thioester 20a (0.4 g, 1.07 mmole) is dissolved in 2 mL of methanol and degassed by argon. A solution of NH$_2$OK (6.1 mL, 1.7 M in methanol, solution prepared as described in Fieser and Fieser, Vol 1, p 478) is also degassed and added to the thioester solution. After 2 hr with stirring, the reaction is acidified with 1N HCl, concentrated to remove solvent, then distributed between HCl and ethyl acetate. The ethyl acetate layer is washed with brine, dried over MgSO$_4$ and concentrated to an oil. The crude product is purified by flash chromatography (1% formic acid in EtOAc) on silica gel to give the desired product. ESI MS: m/z (rel intensity) 333 (90, M$^+$+H).

Example 21 a. (±)-(1N)-4-Methoxyphenysulfonyl-(2R)-carbomethoxy-(3S)-phenyl-pyrrolidine: (±)-trans-3-phenylproline (403 mg, 1.73 mmole, prepared as described in *J. Med. Chem.* 1994, 37, 4371.) is dissolved in water:dioxane (1:1, 5 mL) with triethylamine (0.6 mL, 4.33 mmole). 4-Methoxyphenylsulfonyl chloride (393 mg, 1.9 mmole) is added along with 2,6-dimethylaminopyridine (catalytic) and the mixture is stirred 14 hr. at room temperature. The mixture is then concentrated and diluted with EtOAc. Layers are separated and the organic layer is washed 2× with 1N HCl, 1× with brine, dried over MgSO$_4$, filtered and evaporated to give 623 mg of solid material which is dissolved in MeOH (15 mL). Thionyl chloride (1.5 mL) is added dropwise and the resulting mixture stirred for 14 hr. Silica gel (4 mL) is added and the mixture concentrated. The resulting powder is poured onto a flash silica column and eluted with hexane:EtOAc (1:1 to 0:1) to give the title compound. ESI MS: m/z (rel intensity) 376.1 ($M^++H$, 100), 316.1 (22).

b. (±)-(1N)-4-Methoxyphenylsulfonyl-(2R)-N-hydroxycarboxamido-(3S)-phenylpyrrolidine: The methylester 21a (0.262 g, 0.699 mmole) is taken in 1 mL of methanol, treated with $NH_2OK$ (1.2 mL, 0.86 M in methanol, solution prepared as described in Fieser and Fieser, Vol 1, p 478) and stirred overnight. The following morning, dry silica (2 mL) is added to the mixture and the solvent removed under vacuum. The dry silica is poured on the top of a flash silica gel column which is subsequently eluted with hexane:EtOAc:$HCO_2H$ (2:1 to 0:1) to give pure white solid which is recrystallized from $CHCl_3$:hexane (3:1) to give white crystals. ESI MS: m/z (rel intensity) 377.1 (M++H, 100), 394.1 ($M^++NH_3$, 22).

Example 22 a. (1N)-4-Methoxyphenylsulfonyl-(2R)-carboxy-(4R)-hydroxy-pyrrolidine: cis-Hydroxy-D-proline (10 g, 0.38 mole) is dissolved in water:dioxane (1:1, 60 mL) with triethylamine (25 mL). 4-Methoxyphenylsulfonyl chloride (17.4 g, 0.084 mole) is added along with 2,6-dimethylaminopyridine (0.92 g, 0.008 mole) and the mixture is stirred 14 hr. at room temperature. The mixture is then concentrated and diluted with EtOAc. Layers are separated and the organic layer is washed 2× with 1N HCl, 1× with brine, dried over $MgSO_4$, filtered and evaporated to give the title compound. ESI MS: 302.2 (M++H, 100), 319.3 ($M^++NH_4$, 85).

b. (1N)-4-Methoxyphenylsulfonyl-(2R)-carboxy-4-oxo-pyrrolidine: A 0.76 M batch of Jones' reagent is prepared. The carboxyalcohol 22a (10.0 g, 31.7 mmoles) is dissolved in 175 mL of acetone and cooled to 0° C. Jone's reagent is added (420 mL, 317 mmoles) and this is stirred at room temperature for 14 hr. The reaction mixture is diluted with water and extracted 3× with EtOAc. The organic layers are washed 3× with water and 1× with sodium chloride, dried over magnesium sulfate, and evaporated. the material is recrystallized from Hex:EtOAc to give the pure ketoacid. ESI MS: 300.3 (M++H, 93), 317.3 ($M^++NH_4$, 100).

c. (1N)-4-Methoxyphenylsulfonyl-(2R)-carbomethoxy-(4,4)-(R)-hydroxy-ethylpyrrolidine: The ketone 22b (0.500 g, 1.67 mmole) is taken in 10 mL of THF and cooled to −15° C. Ethylmagnesium bromide (3.67 mL, 1M in THF, 3.67 mmole) is added to this mixture. The mixture is stirred for 30 min at which time it is partitioned between 1N HCl and EtOAc. The organic layer is washed with brine, dried over magnesium sulfate, filtered and evaporated. The crude material is then stirred overnight in methanol with 0.5 mL of $SOCl_2$ and evaporated to dryness. The crude material is chromatographed over flash silica with hex:EtOAc (1:1) to give the pure title compound. ESI MS: 363.3 ($M^++NH_4$, 45), 346.3 ($M^++H$, 100).

d. (1N)-4-Methoxyphenylsulfonyl-(2R)-hydroxy-carboxamido-(4,4)-(R)-hydroxy-ethylpyrrolidine: The methylester 22c (431 mg, 1.26 mmole) is taken in 1 mL of methanol, treated with $NH_2OK$ (2 mL, 0.86 M in methanol, solution prepared as described in Fieser and Fieser, Vol 1, p 478) and stirred overnight. The following morning, dry silica (2 mL) is added to the mixture and the solvent removed under vacuum. The dry silica is poured on the top of a flash silica gel column which is subsequently eluted with hexane:EtOAc:$HCO_2H$ (2:1 to 0:1) to give pure white solid which is recrystallized from $CHCl_3$:hexane (3:1) to give white crystals. ESI MS: 362.2 ($M^++NH_3$, 60), 345.2 ($M^++H$, 100), 327.2 (15).

Example 23 a. (1N)-4Methoxyphenylsulfonyl-(2R)-carbomethoxy-(4,4)-(R)-gem-hydroxy-phenylpyrrolidine: The keto acid 22b (441 mg, 1.47 mmole) is treated with phenylmagnesium bromide (3.7 mL, 3.7 mmole) as described for 22c to give a black residue. This is then treated with $K_2CO_3$ (760 mg, 5.5 mmole) and MeI (0.343 mL, 5.5 mmole) in 10 mL of DMF for 45 min. This mixture is then partitioned between EtOAc and brine. The organic layer is then dried over $MgSO_4$, filtered and evaporated. The crude residue is then chromatographed over flash silica with hexane:EtOAc (9:1 to 7:3) to give the title compound as a brown oil. $CI^+$ MS: m/z (rel intensity) 409.4 ($M+NH_4^+$, 100), 392.4 ($M^++H$, 75), 374.4 (65), 204.2 (72).

b. (1N)-4-Methoxyphenylsulfonyl-(2R)-N-hydroxycarboxamido-(4,4)-(R)-gem-hydroxyphenylpyrrolidine: The ester 23a (174 mg, 0.445 mmole) is converted to the title hydroxamic acid as described for 22d. ESI MS: m/z (rel intensity) 410.6 ($M+NH_4^+$, 100), 393.4 ($M^++H$, 75), 375.5 (65).

Example 24 a. (1N)-4-Methoxyphenylsulfonyl-(2R)-carbomethoxy-(4S)-(4-octyl)phenoxy cyclobutylamine: Triphenylphosphine (2.5 g, 9.51 mmole) was dissolved in 20 mL of THF, diethyl azodicarboxylate (1.9 mL, 9.51 mmole) was added dropwise at 0° C. After 30 min with stirring., a solution of 4-octylphenol (2.46 g, 11.9 mmole) and the alcohol 1a (1.5 g, 4.76 mmole) in 20 mL of THF was added dropwise. The reaction was stirred at 0° C. for 30 min., room temperature overnight and concentrated to an oil. The crude product was purified by flash chromatography (hexane/EtOAc, 1:1) on silica gel to give the desired product. $CI^+$ MS: m/z (rel intensity) 504 (44, $M^++H$), 334 (100).

b. (1N)-4-Methoxyphenylsulfonamido-(2R)-hydroxycarboxamido-(4S)-(4-octyl)phenoxy-pyrrolidine: The methyl ester 24a (1.1 g, 2.1 mmole) was taken in 1 mL of methanol, treated with $NH_2OK$ (8 mL, 1.7 M in methanol, solution prepared as described in Fieser and Fieser, Vol 1, p 478) and stirred for 30 hr. Silica (1.5 mL) was added to the mixture and the solvent was removed under vacuum. The dry silica was poured on the top of a flash silica gel column which was subsequently eluted with EtOAc:$CH_3OH$ (95:5 to 90:10) to give 0.6 g (61% yield) of desired product as a white foamy solid. ESI MS: m/z (rel intensity) 527 (30, $M^++Na$), 522 (25, $M^++NH_4$), 505 (100, $M^++H$).

Example 25 a. (1N)-4-Methoxyphenylsulfonyl-(2R)-carbomethoxy-4-oxopyrrolidine: A 0.76 M batch of jone's reagent was prepared. The alcohol 1a (10.0 g, 31.7 mmoles) was dissolved in 175 mL of acetone and cooled to 0° C. Jone's reagent was added (420 mL, 317 mmoles) and this was stirred at room temperature for 4 hr. The reaction mixture was diluted with water and extracted 3× with EtOAc. The organic layers were washed 3× with water and 1× with sodium chloride, dried over magnesium sulfate, and evaporated. Chromotography was performed on silica gel using EtOAc:hexane (1:1) to give pure compound. Starting material was also recovered. CI⁺ MS: m/z (rel intensity) 314.0 (M⁺+H, 100).

b. (1N)-4-Methoxyphenylsulfonyl-(2R)-carbomethoxy-3,3-dimethyl-4-oxopyrrolidine: A solution of potassium bis(trimethylsilyl)amide (0.5 M, 10.2 mmole) in 20.5 mL of toluene is cooled to 0° C. under argon atmosphere and charged with 10 mL of 1,3-dimethyl-3,4,5,6-tetrahydro-2(1H)-pyrimidone. The mixture is cooled to −78° C. A solution of the substrate 25a (800 mg, 2.56 mmole) in 20 mL of THF is then added dropwise and the resulting mixture is stirred for 1 hr. Iodomethane (1.59 mL, 25.6 mmole) is then added and the reaction is stirred at −78° C. and then partitioned between EtOAc and dil. KHSO₄. The organic layer is then washed with brine, dried over MgSO₄, filtered and evaporated. The crude oil is then chromatographed over flash silica with hex:EtOAc (3:1 to 1:1) to give the title compound. CI⁺ MS: m/z (rel intensity) 359 (M+NH₄⁺, 17), 342 (M⁺+H, 20), 172 (100).

c. (1N)-4-Methoxyphenylsulfonyl-(2R)-carbomethoxy-3,3-dimethyl-(4R)-hydroxypyrrolidine: The starting ketone 25b (241 mg, 0.70 mmole) is taken in 5 mL of methanol and treated with NaBH₄ (42 mg, 1.05 mmole) at room temperature. The mixture is stirred at rt for 1 hr, quenced with 1N HCl, and partitioned between 1N HCl and EtOAc. The mixture is then partitioned between 1N HCl and EtOAc. The organic layer is washed with brine, dried over MgSO₄, filtered and concentrated. The crude oil is chromatographed over flash silica to give the title compound as a clear syrup. The 1H NMR indicates a (10:1) diastereomeric mixture. ESI MS: m/z (rel intensity): 346 (M⁺+H, 100), 363 (M⁺+NH₃)

d. (1N)-4-Methoxyphenylsulfonyl-(2R)-N-hydroxycarboxamido-3,3-dimethyl-(4R)-hydroxypyrrolidine: The starting ester 25c (90 mg, 0.26 mmole) is converted to the title compound as described for 22d. ESI MS: m/z (rel intensity): 345.2 (M⁺+H, 100), 362.2 (M⁺+NH₃, 65), 383.1 (M⁺+K, 55).

Examples 26–41

In the following examples W and Z are hydrogen, and Y is OH, n is 1, Ar is substituted or unsubstituted phenyl, and X and Q refer to substituents on the phenyl ring:

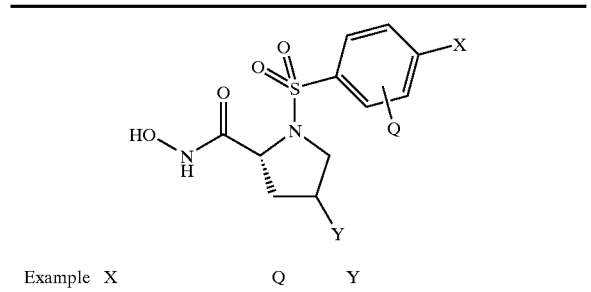

| Example | X | Q | Y |
|---|---|---|---|
| 26 | Me | H | a-OH |
| 27 | OMe | 3-OMe | a-OH |
| 28 | OMe | 2-NO₂ | a-OH |
| 29 | O(n-Bu) | H | a-OH |
| 30 | O(n-Bu) | H | b-OH |
| 31 | Br | H | a-OH |
| 32 | Br | 3-Me | a-OH |
| 33 | Cl | 2-Cl | a-OH |

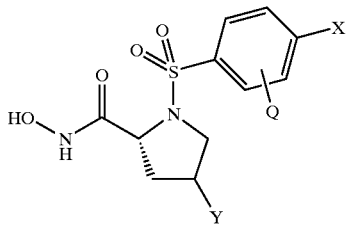

| Example | X | Q | Y |
|---|---|---|---|
| 34 | OCH₂CH₂OCH₃ | H | a-OH |
| 35 | OPh | H | a-OH |
| 36 | OCH(CH₃)₂ | H | a-OH |
| 37 | Br | 2-Me | b-S(3-C₆H₄OMe) |
| 38 | O(n-Bu) | H | b-2-mercaptobenzo-thiazole |
| 39 | OMe | 2-NO₂ | b-2-mercaptobenzo-thiazole |
| 40 | O(n-Bu) | H | b-S(4-C₆H₄OMe) |
| 41 | O(n-Bu) | H | O-(3-pyridyl) |

Me = methyl
Et = ethyl
Bu = butyl

Example 26 a. (1N)-4-Methylphenylsulfonyl-(2R)-carbomethoxy-(4R)-hydroxy-pyrrolidine: Cis-Hydroxy-D-proline methylester (303 mg, 2.09 mmole) is dissolved in DMF (3 mL) and N-methyl morpholine (1 mL) and stirred under air for 14 hr at room temperature in the presence of p-toluenesulfonyl chloride (418 g, 2.19 mmole). The mixture is then partitioned between EtOAc and 1N HCl. The layers are separated and the organic layer is washed 1× with 1N HCl, 1× with brine, dried over MgSO₄, filtered and condensed to give 341 mg of crude material which is chromatographed over flash silica with hexane:MeOH (19:1) to give the desired material as a white solid. CI⁺ MS: m/z (rel intensity) 300 (M⁺+H, 60), 240 (28), 146 (88), 126 (100).

b. (1N)-4-Methylphenylsulfonyl-(2R)-N-hydroxycarboxamido-(4S)-hydroxy-pyrrolidine: The methylester 26a (144 mg, 0.482 mmole) is taken in 1 mL of methanol, treated with NH₂OK (0.61 mL, 0.86 M in methanol, solution prepared as described in Fieser and Fieser, Vol 1, p 478) and stirred overnight. The following morning the material is concentrated and partitioned between EtOAc and 1N HCl. The organic layer is washed with brine, dried over MgSO₄, filtered and evaporated to give 134 mg of crude material which is chromatographed over flash silica with EtOAc:MeOH (10:1) to give desired product which is then recrystallized to give the desired white solid. ESI MS: m/z (rel intensity) 301.0 (M+H⁺, 100), 318.0 (M+NH₄⁺, 35), 322.8 (M+Na⁺, 70).

Example 27 a. (1N)-3,4-Dimethoxyphenylsulfonyl-(2R)-carbomethoxy-(4R)-hydroxy-pyrrolidine: Cis-Hydroxy-D-proline methyl ester (2.71 g, 18.7 mmole) is dissolved in DMF (10 mL) and N-methyl morpholine (5 mL) and stirred under air for 14 hr at room temperature in the presence of 3,4-dimethoxyphenyl-sulfonyl chloride (4.65 g, 19.6 mmole). The mixture is then partitioned between EtOAc and 1N HCl. The layers are separated and the organic layer is washed 1× with 1N HCl, 1× with brine, dried over MgSO₄, filtered and condensed to give 3.98 g of crude material which is chromatographed over flash silica with hexane:EtOAc (2:1 to 1:4) to give the desired material as a white solid. CI$^+$ MS: m/z (rel intensity) 346 (M$^+$+H, 100), 286 (20), 146 (15).

b. (1N)-3,4-Dimethoxyphenylsulfonyl-(2R)-N-hydroxycarboxamido-(4R)-hydroxypyrrolidine: The methylester 27a (250 mg, 0.724 mmole) is taken in 5 mL of methanol, treated with NH$_2$OK (1.25 mL, 0.86 M in methanol, solution prepared as described in Fieser and Fieser, Vol 1, p 478) and stirred overnight. The following morning, dry silica (1.5 mL) is added to the mixture and the solvent removed under vacuum. The dry silica is poured on the top of a flash silica gel column which is subsequently eluted with hexane:EtOAc (1:1 to 0:1) to give a white foamy solid. ESI MS: m/z (rel intensity) 347.0 (M$^+$+H, 100), 369.1 (M$^+$+Na, 45).

Example 28 a. (1N)-(2-Nitro-4-methoxyphenylsulfonyl)-(2R)-carbomethoxy-(4R)-hydroxy-pyrrolidine: cis-Hydroxy-D-proline (3.02 g, 23.1 mmole) is dissolved in water:dioxane (1:1, 300 mL) with triethylamine (7.9 mL, 57.5 mmole). 2-Nitro-4-methoxyphenylsulfonyl chloride (6.38 g, 25.4 mole) is added along with 2,6-dimethylaminopyridine (281 mg, 2.31 mmole) and the mixture is stirred 14 hr. at room temperature. The mixture is then concentrated and diluted with EtOAc. Layers are separated and the organic layer is washed 2× with 1N HCl, 1× with brine, dried over MgSO$_4$, filtered and evaporated to give 7.06 g of solid material which is dissolved in MeOH (100 mL). Thionyl chloride (10 mL) is added dropwise and the resulting mixture stirred for 14 hr. The mixture is then evaporated to dryness and triturated with CHCl$_3$ to give a brownish solid which is sufficiently pure to carry forward without purification. CI$^+$ MS: m/z (rel intensity) 378 (M+NH$_4$$^+$, 40), 361 (M$^+$+H, 100), 331 (12), 301 (43), 144 (95).

b. (1N)-(2-Nitro-4-methoxyphenylsulfonyl)-(2R)-N-hydroxy-carboxamido-(4R)-hydroxypyrrolidine: The methylester 28a (300 mg, 0.833 mmole) is taken in 4 mL of methanol, treated with NH$_2$OK (1.44 mL, 0.86 M in methanol, solution prepared as described in Fieser and Fieser, Vol 1, p 478) and stirred overnight. The following morning, dry silica (2 mL) is added to the mixture and the solvent removed under vacuum. The dry silica is poured on the top of a flash silica gel column which is subsequently eluted with hexane:EtOAc (4:1) then with EtOAc:MeOH:NH$_4$OH (8:2:0.1) to give a white solid. ESI MS: m/z (rel intensity) 362.0 (M$^+$+H, 100), 379.2 (M$^+$+NH$_4$$^+$, 7), 384.1 (M$^+$+Na$^+$, 55).

Example 29 a. (1N)-(4-$^n$Butoxyphenylsulfonyl)-(2R)-carbomethoxy-(4R)-hydroxy-pyrrolidine: Cis-D-Hydroxyproline methyl ester (583 mg, 4.02 mmole) is dissolved in DMF (7 mL) and N-methyl morpholine (3 mL) and stirred under air for 14 hr at room temperature in the presence of para-n-butoxyphenylsulfonyl chloride (1.00 g, 4.02 mmole). The mixture is then partitioned between EtOAc and 1N HCl. The layers are separated and the organic layer is washed 1× with 1N HCl, 1× with brine, dried over MgSO$_4$, filtered and condensed to give 1.2 g of crude material which is chromatographed over flash silica with hexane:EtOAc (4:1 to 1:3) to give the material as a white solid. CI$^+$ MS: m/z (rel intensity) 358 (M$^+$+H, 100), 298 (23), 146 (53), 114 (24).

b. (1N)-4-$^n$Butoxyphenylsulfonamido-(2R)-N-hydroxycarboxamido-(4R)-hydroxypyrrolidine: The methylester 29a (347 mg, 0.971 mmole) is taken in 2 mL of methanol, treated with NH$_2$OK (1.68 mL, 0.86 M in methanol, solution prepared as described in Fieser and Fieser, Vol 1, p 478) and stirred overnight. The following morning, dry silica (2 mL) is added to the mixture and the solvent removed under vacuum. The dry silica is poured on the top of a flash silica gel column which is subsequently eluted with hexane:EtOAc (4:1) then with EtOAc:MeOH:NH$_4$OH (4:1:0.1) to give a white solid. ESI MS: m/z (rel intensity) 359.1 (M$^+$+H, 100), 381.1 (M$^+$+Na, 45).

Example 30 a. (1N)-4-Methoxyphenylsulfonyl-(2R)-carbomethoxy-(4S)-benzoyl-pyrrolidine: The alcohol 29a (200 mg, 0.56 mmole) is dissolved in 1.5 mL of methylene chloride. Benzoic acid (82 mg, 0.672 mmole) and triphenyl phosphine (220 mg, 0.84 mmole) are then added, followed by diethyl azodicarboxylate (106 mL, 0.672 mmole). After 3 hrs, the reaction mixture is filtered and silica gel is added to the filtrate to adsorb the solutes and the mixture is concentrated to dryness. The resulting solid mixture is poured onto the top of a flash silica column which is eluted with hex:EtOAc (3:1 to 2:1) to give the desired product a white solid. CI$^+$ MS: m/z (rel intensity) 479.1 (M+NH$_4$$^+$, 55), 462.0 (M$^+$+H, 30), 250.0 (100), 126 (38).

b. (1N)-4-$^n$Butoxyphenylsulfonyl-(2R)-N-hydroxycarboxamido-(4S)-hydroxypyrrolidine: The methylester 30a (154 mg, 0.334 mmole) is taken in 2 mL of methanol, treated with NH$_2$OK (1.0 mL, 0.86 M in methanol, solution prepared as described in Fieser and Fieser, Vol 1, p 478) and stirred overnight. The following morning, dry silica (1.5 mL) is added to the mixture and the solvent removed under vacuum. The dry silica is poured on the top of a flash silica gel column which is subsequently eluted with hexane:EtOAc (1:1 to 0:1) and finally with EtOAc:MeOH:NH$_4$OH (9:1:0.1) to give a clear glassy solid. ESI MS: m/z (rel intensity) 359 (M$^+$+H, 40), 376 (M+NH$_4$$^+$, 30), 381 (M+Na$^+$, 20).

Example 31 a. (1N)-4-Bromobenzenesulfonyl-(2R)-carbomethoxy-(4R)-hydroxypyrrolidine: The title ester was prepared as described for compound 28a from cis-hydroxy-D-proline (4.43 g, 35.1 mmole) and 4-bromobenzenesulfonyl chloride. ESI MS: m/z (rel intensity) 364.0 (M$^+$+H, 95), 366.0 (M$^+$+H, 95), 381.0 (M$^+$+NH$_3$, 98), 383.0 (M$^+$+NH$_3$, 100).

b. (1N)-4-Bromobenzenesulfonyl-(2R)-N-hydroxycarboxamido-(4R)-hydroxy-pyrrolidine: The title hydroxamic acid was prepared from ester 31a (7.59 g, 20.9 mmole) as described for compound 25. The resulting material was recrystallized from EtOAc. ESI MS: m/z (rel intensity) 365.1 (M$^+$+H, 98), 367.1 (M$^+$+H, 100), 382.2 (M+NH$_4$$^+$, 45), 384.2 (M+NH$_4$$^+$, 45).

Example 32 a. (1N)-2-Methyl-4-bromobenzenesulfonyl-(2R)-carbomethoxy-(4R)-hydroxypyrrolidine: The title ester was prepared as described for compound 28a from cis-hydroxy-D-proline (361 mg, 2.76 mmole) and 2-methyl-4-bromobenzenesulfonyl chloride. CI$^+$ MS: m/z (rel intensity) 397 (M$^+$+NH$_3$, 100), 395 (M$^+$+NH$_3$, 95), 380 (M$^+$+H, 50), 378 (M$^+$+H, 45), 317 (35), 300 (20), 146 (40).

b. (1N)-2-Methyl-4-bromobenzenesulfonyl-(2R)-hydroxycarboxamido-(4R)-hydroxypyrrolidine: The title hydroxamic acid was prepared from ester 32a (271 mg, 0.72 mmole) as described for compound 28. The resulting material was recrystallized from water. ESI MS: m/z (rel intensity) 398 ($M^++NH_3$, 85), 396 ($M^++NH_3$, 80), 379 ($M^++H$, 90), 381 ($M^++H$, 100).

Example 33 a. (1N)-2,4-Dichloro-(2R)-carbomethoxy-(4R)-hydroxypyrrolidine: The title compound is prepared as described for compound 28a from cis-hydroxy-D-proline (500 mg, 3.8 mmole) and 2,4-dichlorobenzenesulfonyl chloride (1.03 g, 4.2 mmole). ESI MS: m/z (rel intensity) 354.0 (M++H, 100), 356.0 ($M^++H$, 73), 371.0 ($M^++NH_4$, 78), 373.0 ($M^++NH_4$, 54).

b. (1N)-2,4-Dichloro-(2R)-N-hydroxycarboxamido-(4R)-hydroxypyrrolidine: The title compound is prepared from ester 33a (550 mg, 1.55 mmole) as described for compound 28b. ESI MS: m/z (rel intensity) 355.1 ($M^++H$, 100), 372.2 ($M+NH_4^+$, 67).

Example 34 a. 4-(2-Methoxyethoxy)-phenylsulfonyl chloride: Methylsulfoxide (400 mL) is cooled with an ice/water bath with mechanical stirring and charged with potassium hydroxide pellets (118.2 g, 2.11 mole) followed by phenol (94.1 g, 0.70 mole) and then 2-bromoethylmethyl ether (86 mL, 0.9 mole) is added at a rapid dripping rate. The mixture is stirred for 15 min., warmed to room temperature and then stirred for 2 hrs. It is then diluted with 1 L of ice/water and extracted 2 times with $CH_2Cl_2$. The combined organic layers were then dried over $MgSO_4$, filtered and evaporated The yield s in excess of 100% so it is taken in $CHCl_3$ and washed 2 times with water and 1 time with brine. This organic layer was processed similarly and the concentrate was taken in 1.1 L of $CH_2Cl_2$ in a mechanically stirred flask 5 L flask. Chlorosulfonic acid (140 mL, 2.1 mole) is added dropwise causing slight warming A heavy precipitate is observed after addition of half of the reagent, so the mixture is diluted with 1.1 L of additional $CH_2Cl_2$. The resulting mixture is allowed to stir at rt for 16 hrs. It is then poured onto ~2 L of ice/water. The layers are separated and the aqueous layer is extracted two times with $CH_2Cl_2$. The combined organic layers are then combined, dried over MgSO4, filtered and evaporated to give the desired material which is sufficiently pure to carry forward without purification. ESI MS: m/z (rel intensity) 247.1 ($M^++H$, 35), 264.1 ($M^++NH_3$, 100), 269.0 ($M^++Na$, 45).

b. (1N)-4-(2-Methoxyethyl)phenylsulfonyl-(2R)-N-hydroxycarboxamido-(4R)-hydroxypyrrolidine: The title compound is prepared as described for compound 28a. ESI MS: m/z (rel intensity) 360.1 ($M^++H$, 85), 377.1 ($M^++NH_4$, 100).

c. (1N)-4-(2-Methoxyethyl)phenylsulfonyl-(2R)-N-hydroxycarboxamido-(4R)-hydroxypyrrolidine: The starting methylester 34b (347 mg, 0.971 mmole) is stirred overnight in 3 mL of methanol in the presence of $NH_2OK$ (3.6 mL, 1.25 M in methanol, solution prepared as described in Fieser and Fieser, Vol 1, p 478). The solution is then partitioned between 0.1 N HCl and EtOAc. The organic layer is dried over $MgSO_4$, filtered and evaporated to give 710 mg of a yellow solid which is chromatographed over flash silica with EtOAc:MeOH (1:0 to 5:1) to give the title compound which is puffed into a solid white foam under vacuum. ESI MS: m/z (rel intensity) 361.1 ($M^++H$, 100), 378.1 ($M^++NH_4$, 25).

Example 35 a. (1N)-4-Phenoxyphenylsulfonyl-(2R)-carbomethoxy-(4R)-hydroxypyrrolidine: The title compound is prepared from cis-D-hydroxyproline (5.00 g, 38.1 mmole) and phenoxyphenylsulfonyl chloride (11.2 g, 42 mmole, prepared as described by R. J. Cremlyn et al in *Aust. J. Chem.*, 1979, 32, 445.52) as described for compound 28a. The compound is purified over flash silica with EtOAc:hexane (1:1 to 1:0) to give the title compound as a clear gum. $CI^+$ MS: m/z (rel intensity) 378.11 ($M^++H$, 100), 395.11 ($M^++NH_3$, 40).

b. (1N)-4-Phenoxyphenylsulfonyl-(2R)-N-hydroxycarboxamido-(4R)-hydroxypyrrolidine: The starting methyl ester 35a (864 mg, 2.30 mmole) is taken in 6 mL of methanol:tetrahydrofuran (1:1), and treated with $NH_2OK$ (3 mL, 1.25M in methanol) and stirred overnight. The following morning, dry silica (1.5 mL) is added to the mixture and the solvent removed under vacuum. The dry silica is poured on top of a flash silica column which is subsequently eluted with ethyl acetate followed with ethyl acetate:methanol (8:2) to give a clear glass which is puffed to a foamy solid by slight heating under vacuum. The product was recrystallized from cold methanol to give the title compound as a white powder. ESI MS: m/z (rel intensity) 379.10 ($M^++H$, 100), 396.10 ($M^++NH_3$, 10).

Example 36 a. 4-(iso-butoxy)-phenylsulfonyl chloride: The title compound was prepared as described for example 34a. ESI MS: m/z (rel intensity) 245.1 ($M^++H$, 50), 262.1 ($M^++NH_3$, 100).

b. (1N)-4-iso-butyloxyphenylsulfonyl-(2R)-carbomethoxy-(4R)-hydroxypyrrolidine: The title ester was prepared from cis-hydroxy-D-proline (10.0 g, 76.3 mmole) and sulfonyl chloride 36a (19.0 g, 76.3 mmole) as described for compound 25a. ESI MS: m/z (rel intensity) 358.1 ($M^++H$, 100), 375.1 ($M^++Na$, 45).

c. (1N)-4-iso-butyloxyphenylsulfonyl-(2R)-N-hydroxycarboxamido-(4R)-hydroxy-pyrrolidine: The starting methyl ester 36b (1.5 g, 4.2 mmole) is taken in 7 mL of methanol, and treated with $NH_2OK$ (7 mL, 1.25M in methanol) and stirred overnight. A precipitate formed which is filtered and purified by partioning between water and EtOAc. The organic layer is concentrated in vacuo and recrystallized from hexane:EtOAc to give pure material. The original filtrate is dried and worked up like the filtrate and filtered through dry silica gel with EtOAc:MeOH (9:1) and the product was recrystallized from EtOAc:hexane to give additional product. ESI MS: m/z (rel intensity) 359.1 ($M^++H$, 100), 376.1 ($M^++NH_4$, 55), 381.1 ($M^++Na$, 15).

Example 37 a. 1N)-2-Methyl-4-bromophenylsulfonyl-(2R)-carbomethoxy-(4S)-(3-methoxymercapto-phenyl)-pyrrolidine: The starting alcohol 32a (310 mg, 0.82 mmole) is taken in 5 mL of $CH_2Cl_2$ and 1 mL of triethylamine and treated with methanesulfonyl chloride (76 μL, 0.984 mmole). The solution is stirred for 1 hr at rt and then partitioned between EtOAc and 1N HCl. The organic layer was dried over $MgSO_4$, filtered and evaporated. The crude residue was then taken in 2.5 mL of THF at rt under argon and treated first with ᵗbutoxide (50 mg, 0.45 mmole) and then 3-methoxythiophenol (110 μL, 0.90 mmole) The mixture is stirred for 16 hr and then partitioned between EtOAc and 1N HCl. The organic layer is washed with brine, dried over $Na_2SO_4$, filtered and evaporated to give a residue which is then chromatographed over flash silica with hexane:EtOAc (4:1) to give the title compound as a clear glass. CI$^+$ MS: m/z (rel intensity) 517, 519 (M$^+$+NH$_3$, 92), 500, 502 (M$^+$+H, 48) 439 (30), 422 (20), 141 (50), 128 (100).

b. (1N)-2-Methyl-4-bromophenylsulfonyl-(2R)-N-hydroxycarboxamido-(4S)-(3-methoxymercaptophenyl)-pyrrolidine: The methylester 37a (101 mg, 0.202 mmole) is taken in 2 mL of methanol:THF (1:1), treated with NH$_2$OK (2.0 mL, 1.25 M in methanol, solution prepared as described in Fieser and Fieser, Vol 1, p 478) and stirred overnight. The following morning, dry silica (1.5 mL) is added to the mixture and the solvent removed under vacuum. The dry silica is poured on the top of a flash silica gel column which is subsequently eluted with EtOAc and then with EtOAc:MeOH (4:1) to give 79 mg (79%) of a clear glassy solid. ESI MS: m/z (rel intensity) 501, 503 (M$^+$+H, 65), 518, 520 (M$^+$+NH$_3$, 100), 523, 525 (M$^+$+Na, 35).

Example 38 a. (1N)-$^n$Butoxyphenylsulfonyl-(2R)-N-hydroxycarboxamido-(4S)-(2-mercaptobenzothiazolyl)-pyrrolidine: The alcohol 29a (200 mg, 0.56 mmole) is dissolved in 2.5 mL of methylene chloride. 2-Mercaptobenzothiazole (113 mg, 0.672 mmole) and triphenyl-phosphine (220 mg, 0.84 mmole) are then added, followed by diethyl azodicarboxylate (106 mL, 0.672 mmole). After 3 hrs, the reaction mixture is filtered and silica gel is added to the filtrate to adsorb the solutes and the mixture is concentrated to dryness. The resulting solid mixture is poured onto the top of a flash silica column which is eluted with hex:EtOAc (2:1 to 1:1) to give the desired product. MS CI$^+$: m/z (rel intensity) 507.0 (M+H$^+$, 30), 359.1 (42), 342.0 (39), 167.9 (100), 135.9 (90).

b. (1N)-4-$^n$Butoxyphenylsulfonyl-(2R)-N-hydroxycarboxamido-(4S)-(2-mercapto-benzothiazolyl)-pyrrolidine: The methylester 38a (214 mg, 0.422 mmole) is taken in 1.5 mL of methanol, treated with NH$_2$OK (0.73 mL, 0.86 M in methanol, solution prepared as described in Fieser and Fieser, Vol 1, p 478) and stirred overnight. The following morning, dry silica (2 mL) is added to the mixture and the solvent removed under vacuum. The dry silica is poured on the top of a flash silica gel column which is subsequently eluted with hexane:EtOAc (1:1 to 0:1) and finally with EtOAc:MeOH:NH$_4$OH (4:1:0.1) to give a white powder. ESI MS: m/z (rel intensity) 508 (M$^+$+H, 100), 532 (M$^+$+Na, 32).

Example 39 a. (1N)-2-Nitro-4-methoxyphenylsulfonyl-(2R)-N-carbomethoxy-(4S)-(2-mercapto-benzothiazolyl)-pyrrolidine: The alcohol 28a (200 mg, 0.55 mmole) is dissolved in 1.5 mL of methylene chloride. 2-Mercaptobenzothiazole (112 mg, 0.66 mmole) and triphenyl phosphine (219 mg, 0.833 mmole) are then added, followed by diethyl azodicarboxylate (105 mL, 0.666 mmole). After 3 hrs, the reaction mixture is filtered and silica gel is added to the filtrate to adsorb the solutes and the mixture is concentrated to dryness. The resulting solid mixture is poured onto the top of a flash silica column which is eluted with hex:EtOAc (4:1 to 1:1) to give the desired product as a white solid. CI$^+$ MS: m/z (rel intensity) 509.9 (M$^+$+H, 30), 315.0 (18), 294.9 (18), 167.9 (100), 135.9 (95).

b. (1N)-2-Nitro-4-methoxyphenylsulfonyl-(2R)-N-hydroxycarboxamido-(4S)-(2-mercapto-benzothiazolyl)-pyrrolidine: The methylester 39a (277 mg, 0.544 mmole) is taken in 1 mL of methanol, treated with NH$_2$OK (1.0 mL, 0.86 M in methanol, solution prepared as described in Fieser and Fieser, Vol 1, p 478) and stirred overnight. The following morning, dry silica (2 mL) is added to the mixture and the solvent removed under vacuum. The dry silica is poured on the top of a flash silica gel column which is subsequently eluted with hexane:EtOAc (1:1 to 0:1) followed by EtOAc:MeOH:NH$_4$OH (9:1:0.1) to give the white solid. ESI MS: m/z (rel intensity) 511.1 (M$^+$+H, 100), 533.0 (M$^+$+Na, 30).

Example 40 a. (1N)-(4-$^n$butoxyphenylsulfonyl)-(2R)-carbomethoxy-(4S)-(4-methoxy-mercaptophenyl)-pyrrolidine: The alcohol 29a (178 mg, 0.499 mmole) is taken in 2 mL of CH$_2$Cl$_2$ and to this mixture is added triphenylphosphene (157 mg, 0.599 mmole), 4-methoxythiophenol (67 mL, 0.548 mmole), and diethyl-diazadicarboxylate (95 mM, 0.0.548 mmole) and the mixture is stirred for 3 hr. at which time 3 mL of silica gel is added to the mixture which is then concentrated to dryness. The dry residue is poured onto the top of a flash silica column and eluted with hexane:EtOAc (4:1 to 1:4) to give a clear oil. CI$^+$ MS: m/z (rel intensity) 468 (M$^+$+H, 48), 301 (43), 272 (46), 187 (65), 109 (100).

b. (1N)-(4-Methoxyphenylsulfonyl)-(2R)-N-hydroxycarboxamido-(4S)-(4-methoxyphenyl-thioloxy)-pyrrolidine: The methylester 40a (125 g, 0.268 mmole) is taken in 1 mL of methanol, treated with NH$_2$OK (0.465 mL, 0.86 M in methanol, solution prepared as described in Fieser and Fieser, Vol 1, p 478) and stirred overnight. The following morning, dry silica (2 mL) is added to the mixture and the solvent removed under vacuum. The dry silica is poured on the top of a flash silica gel column which is subsequently eluted with hexane:EtOAc (2:1 to 0:1) to give a white solid. ESI MS: m/z (rel intensity) 481 (M$^+$+H, 10), 498.1 (M+NH$_4^+$, 100), 503.1 (M$^+$+Na, 20).

Example 41 a. (1N)-4-$^n$Butoxyphenylsulfonyl-(2R)-carbomethoxy-(4S)-(3-pyridyloxy)-pyrrolidine: The title compound is prepared as described for 13a. CI$^+$ MS: m/z (rel intensity) 468 (M$^+$+H, 8), 301 (43), 272 (46), 187 (65), 109 (100).

b. (1N)-4-$^n$Butoxyphenylsulfonyl-(2R)-N-hydroxycarboxamido-(4S)-(3-pyridyloxy)-pyrrolidine: The title compound is prepared as described for 13b. ESI MS: m/z (rel intensity) 436.1 (M$^+$+H, 100), 458.1 (M+NH$_4^+$, 60), 517.8 (M$^+$+Na, 15).

Examples 42–61

In the following examples W and Z are hydrogen, and Y is OH, n is 1, Ar is substituted or unsubstituted phenyl, and X and Q refer to substituents on the phenyl ring:

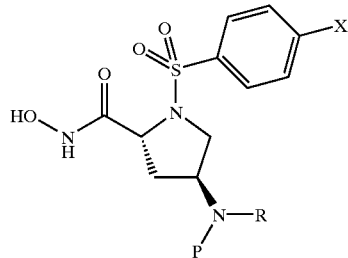

| Example | X | P | R |
|---|---|---|---|
| 42 | OMe | H | H |
| 43 | OnBu | H | H |
| 44 | OMe | H | n-Pr |
| 45 | OMe | H | n-Hex |
| 46 | OMe | H | $CH_2CH_2Ph$ |
| 47 | OMe | n-Bu | n-Hex |
| 48 | OMe | H | $SO_2Me$ |
| 49 | On-Bu | H | $SO_2Me$ |
| 50 | On-Bu | H | SO23-(N-methylimidazole) |
| 51 | OMe | $CH_2$(3-pyridyl) | $SO_2Me$ |
| 52 | OMe | $SO_2Me$ | $SO_2Me$ |
| 53 | OMe | n-Pr | $SO_2Me$ |
| 54 | OMe | H | $SO_2pC_6H_4OMe$ |
| 55 | OMe | H | COn-Pent |
| 56 | OMe | H | COp-Ph-Ph |
| 57 | OMe | H | CONHMe |
| 58 | OMe | H | $COCH(R-OBn)CH_3$ |
| 59 | OMe | H | $COCH(R-OBn)CH_2Ph$ |
| 60 | OMe | i-Pr | $COCH(R-OH)CH_3$ |
| 61 | OMe | i-Pr | $COCH(R-OH)CH_2Ph$ |

Example 42 a. (1N)-4-Methoxyphenylsulfonyl-(2R)-carbomethoxy-(4S)-azidopyrrolidine: The starting mesylate 15a (4.2g, 10.7 mmole) is taken in 15 mL of dry DMF in the presence of $NaN_3$ (695 mg, 10.7 mmole). The resulting mixture is heated to 55° C. for 26 hrs and then partitioned between water and EtOAc. The organic layer is then washed with brine, dried over $MgSO_4$, filtered and evaporated. The resulting crude oil is chromatographed over flash silica with hexane:EtOAc (5:1 to 3:1) to provide pale yellow oil which solidifies upon standing. $CI^+$ MS: m/z (rel intensity) 358 ($M+NH_4^+$, 50), 341 (M++H, 67), 315 (95), 145 (100).

b. (1N)-4-Methoxyphenylsulfonyl-(2R)-carbomethoxy-(4S)-aminopyrrolidine: The starting azide 42a (1.18 g, 3.48 mmole), is taken in 100 mL of $EtOH:THF:HCO_2H$ (5:1:0.1), and hydrogenated at rt. under 54 psi of hydrogen in the presence of 100 mg of 10% Pd—C for 16 hrs. The mixture is then filtered through a pad of celite, concentrated to an oil and recrystallized from hexane:EtOAc to give the desired product as the formate salt. $CI^+$ MS: m/z (rel intensity) 315 ($M^+$+H, 12), 177 (13), 143 (42), 123 (60), 109 (100).

c. (1N)-4-Methoxyphenylsulfonyl-(2R)-N-hydroxycarboxamido-(4S)-aminopyrrolidine: The starting ester 42b (500 mg, 1.59 mmole), is taken in 5 mL of MeOH, treated with $NH_2OK$ (1.92 mL, 0.86 M in methanol, solution prepared as described in Fieser and Fieser, Vol. 1, p 478) and stirred overnight. The following morning, dry silica (1.5 mL) is added to the mixture and the solvent removed under vacuum. The dry silica is poured on the top of a flash silica gel column which is subsequently eluted with EtOAc:MeOH (4:1 to 3:2) to give white solid. ESI MS: m/z (rel intensity) 316.3 ($M^+$+H, 100), 333.3 ($M^+$+$NH_4$, 15).

Example 43 a. (1N)-4-"Butoxyphenylsulfonyl-(2R)-carbomethoxy-(4R)-methylsulfonoxy-pyrrolidine: The starting alcohol 1a (6.78 g, 19.0 mmole) is converted to the title mesylate as described for compound 15a. CI MS: m/z (rel intensity) 453 ($M+NH_4^+$, 38), 336 ($M^+$+H, 27), 224 (100), 128 (67).

b. (1N)-4-"Butoxyphenylsulfonyl-(2R)-carbomethoxy-(4S)-azidopyrrolidine: The starting mesylate 43a (5.85 g, 13.5 mmole) is converted to the title azide as described for compound 41a. ESI MS: m/z (rel intensity) 383.1 ($M^+$+H, 50), 400.1 ($M^+$+$NH_3$, 100)

c. (1N)-4-"Butoxyphenylsulfonyl-(2R)-carbomethoxy-(4S)-aminopyrrolidine: The starting azide 43b (4.65 g, 12.2 mmole), is taken in 200 mL of MeOH with 20 mL of HOAc and hydrogenated at rt. under 54 psi of hydrogen in the presence of 200 mg of 10% Pd—C for 16 hrs. The mixture is then filtered through a pad of celite, concentrated to an oil, taken in MeOH and stirred with ~50 g of Amberlite IRA-68 basic resin (preconditioned with 0.1 N NaOH, water and MeOH), filtered through a glass frit and adsorbed onto a plug of silica. This is then eluted over a column of flash silica with EtOAc:MeOH (1:0 to 3:1) to give pale yellow oil which solidifies upon standing. CI MS: m/z (rel intensity) 357 ($M^+$+H, 65), 145 (100).

d. (1N)-4-Methoxyphenylsulfonyl-(2R)-hydroxycarboxamido-(4S)-amino-pyrrolidine: The starting ester 43c (234 mg, 356 mmole), is converted to the title compound as described for compound 42c and then purified further by recrystallizing from water to give white crystals. ESI MS: m/z (rel intensity) 358 ($M^+$+H).

Example 44 a. (1N)-4-Methoxyphenylsulfonyl-(2R)-carbomethoxy-(4S)-propylamino-pyrrolidine: The starting amine 42b (810 mg, 2.6 mmole) is dissolved in 8 mL of methanol and stirred for 48 hrs in the presence of propianaldehyde (206 mL, 2.86 mmole), sodium cyanoborohydride (180 mg, 2.86 mmole), sodium acetate (810, 9.9 mmole) and 25 drops of acetic acid. The mixture is evaporated to dryness and then partitioned between dil. $NaHCO_3$ and EtOAc and the organic layer is washed 2 times with $NaHCO_3$, 1 time with brine, dried over $MgSO_4$, filtered and evaporated to give a gummy oil which was sufficiently clean to carry forward without further purification. ESI MS: m/z (rel intensity) 357.3 ($M^+$+H, 100).

b. (1N)-4-Methoxyphenylsulfonyl-(2R)-N-hydroxycarboxamido-(4S)-propylamino-pyrrolidine: The starting methylester 44a (11.3, g, 31.7 mmole) is taken in 30 mL of methanol, treated with $NH_2OK$ (38 mL, 1.25 M in methanol, solution prepared as described in Fieser and Fieser, Vol 1, p 478) and stirred for 16 hrs. The following morning, dry silica (30 mL) is added to the mixture and the solvent removed under vacuum. The dry silica is poured on the top of a flash silica gel column which is subsequently eluted with chloroform:methanol (8:2) to give a pale yellow solid which was taken in methanol and stirred for 1 hr in the presence of activated charcoal and then filtered through celite and evaporated to give a white solid. ESI MS: m/z (rel intensity) 358.2 ($M^+$+H, 100), 380.1 ($M^+$+Na, 5).

Example 45 a. (1N)-4-Methoxyphenylsulfonyl-(2R)-carbomethoxy-(4S)-"hexylamino-pyrrolidine: The starting alcohol 1a (300 mg, 0.951 mmole) is dissolved in 2 mL of $CH_2Cl_2$ under argon and cooled to 0° C. 2,6-Lutidine (135 µL, 1.14 mmole) is added via syringe followed by like addition of trifluoro-methanesulfonyl anhydride (179 mL, 1.05 µmole). The mixture is stirred for 1 hr., followed by syringe addition of dry hexylamine (500 µL, 3.80 mmol) and then the mixture is allowed to come to room temperature, stir for 14 hrs., and heat to reflux for 4 hrs. Silica gel (3 mL) is added and the mixture evaporated to dryness. The dry powder is poured on the top of a column of flash silica gel which is then eluted with hexane:EtOAc (2:1Ø1:1) to give a colorless, glassy solid. $CI^+$ MS: m/z (rel intensity) 399 ($M^++H$, 38), 229 (100), 227 (62).

b. (1N)-4-Methoxyphenylsulfonyl-(2R)-N-hydroxycarboxamido-(4S)-("hexylamino)-pyrrolidine: The starting methylester 45a (88 mg, 0.221 mmole) is taken in 1 mL of methanol, treated with $NH_2OK$ (0.381 mL, 0.86 M in methanol, solution prepared as described in Fieser and Fieser, Vol 1, p 478) and stirred overnight. The following morning, dry silica (1.5 mL) is added to the mixture and the solvent removed under vacuum. The dry silica is poured on the top of a flash silica gel column which is subsequently eluted with hexane:EtOAc (1:1Ø0:1) to give a white foamy solid. ESI MS: m/z (rel intensity) 400.3 ($M^++H$, 100), 422.2 ($M^++Na$, 12).

Example 46 a. (1N)-4-Methoxyphenylsulfonyl-(2R)-carbomethoxy-(4S)-2-phenylethyl-amino-pyrrolidine: The primary amine 42b (300 mg, 1 mmole) is N-alkylated with phenylacetaldehyde (0.13 mL, 1.1 mmole) as described for compound 44a to give the desired amine as a clear gum which was carried forward without further purification. $CI^+$ MS: m/z (rel intensity) 419 ($M^++H$, 38), 249 (20), 249 (19).

b. (1N)-4-Methoxyphenylsulfonyl-(2R)-N-hydroxycarboxamido-(4S)-2-phenylethyl-aminopyrrolidine: The starting ester 46a (490 mg, 1 mmole) is converted to the title compound as described for compound 45b and purified over flash silica with EtOAc:MeOH (4:1) to give a white solid. ESI MS: m/z (rel intensity) 420.4 ($M^++H$, 100).

Example 47 a. (1N)-4-Methoxyphenylsulfonyl-(2R)-carbomethoxy-(4S)-N,N-"butyl,"hexylamino-pyrrolidine: The starting amine 45a (100 mg, 0.251 mmole) was converted to 93 mg (82%) of the title compound as described for compound 44a. $CI^+$ MS: m/z (rel intensity) 470 ($M^++H$, 10), 299 (20), 242 (100).

b. (1N)-4-Methoxyphenylsulfonyl-(2R)-N-hydroxycarboxamido-(4S)-N,N-"butyl,"hexyl-amino-pyrrolidine: The starting ester 47a (80.5 mg, 0.172 mmole) was converted to 56 mg (69%) of the title compound as described for compound 44b. $CI^+$ MS: m/z (rel intensity) 469 ($M^++H$, 42), 299 (100), 242 (28), 172 (46).

Example 48 a. (1N)-4-Methoxyphenylsulfonyl-(2R)-carbomethoxy-(4S)-methanesulfonyl-amino-pyrrolidine: The primary amine 42b (502 mg, 1.60 mmole) is taken in 5 mL of methylene chloride and 0.5 mL of triethyl amine and treated with methanesulfonyl chloride (200 µL, 2.58 mmole) via syringe. The mixture is stirred for 2 hr and then partitioned between 1N HCl and EtOAc. The organic layer was washed with brine, dried over $MgSO_4$, filtered and evaporated to give 684 mg of crude material which was chromatographed over flash silica with hexane EtOAc (2:1 to 1:1) to give disulfonylated material 51a and monosulfonylated material 47a. $CI^+$MS: m/z (rel intensity) 410 ($M^++NH_4$, 15), 393 ($M^++H$, 10), 203 (100).

b. (1N)-4-Methoxyphenylsulfonyl-(2R)-hydroxycarboxamido-(4S)-methane-sulfonylaminopyrrolidine: The starting ester 48a (354 mg, 0.903 mmole) is converted to the title compound and chromatographed as described for compound 45b. It is then recrystallized from acetonitrile/water to give pale yellow crystals. ESI MS: m/z (rel intensity) 394 ($M^++H$, 60), 411 ($M^++NH_4$, 100).

Example 49 a. (1N)-4-"Butoxyphenylsulfonyl-(2R)-carbomethoxy-(4S)-methanesulfonyl-aminopyrrolidine: The primary amine 43c (21.3 g, 60 mmole) is taken in 120 mL of methylene chloride and 36 mL of triethyl amine and treated dropwise with methanesulfonyl chloride (5.1 mL, 66 mmole) at 0° C. The mixture is allowed to come to room temperature for 1 hr and then adsorbed onto silica, evaporated to dryness, and eluted through a column of flash silica with hexane:EtOAc (4:1 to 1:1) to give the title compound. ESI MS: m/z (rel intensity) 452 ($M^++NH_3$, 12), 435 ($M^++H$, 9), 223 (100).

b. (1N)-4-"Butoxyphenylsulfonyl-(2R)-N-hydroxycarboxamido-(4S)-methane-sulfonyl-aminopyrrolidine: The starting ester 49a (21.4 g, 49.2 mmole) is taken in 60 mL of methanol:THF (1:1), treated with $NH_2OK$ (59 mL, 1.25 M in methanol, solution prepared as described in Fieser and Fieser, Vol 1, p 478) and stirred overnight. The following morning, dry silica (45 mL) is added to the mixture and the solvent removed under vacuum. The dry silica is poured on the top of a flash silica gel column which is subsequently eluted with hexane:EtOAc (1:1Ø0:1), then EtOAc:methanol (9:1) to give a white foamy solid. This material was heated to 60° C. for 48 hrs and a white, solid impurity sublimed off leaving behind light yellow powder. ESI MS: m/z (rel intensity) 453.08 ($M^++NH_3$, 50), 436.05 ($M^++H$, 100).

Example 50 a. (1N)-4-n-Butoxyphenylsulfonyl-(2R)-carbomethoxy-(4S)-[(1N)-methyl-3-imidazolyl]-sulfonylaminopyrrolidine: The primary amine 43c (232 mg, 0.906 mmole) is taken in 3 mL of methylene chloride and 0.5 mL of triethyl amine and treated with 1N-methyl-3-imidazoyl-sulfonyl chloride (280 mg, 1.55 mmole) at rt. The mixture is allowed to stir for 16 hr and then adsorbed onto silica, evaporated to dryness, and eluted through a column of flash silica with hexane:EtOAc (1:1 to 0:1) to give the title compound as a clear oil which contained ~20 mole percent of the starting sulfonyl chloride. This material was carried forward without further purification. ESI MS: m/z (rel intensity) 501 ($M^++H$, 70), 357 (45), 289 (82), 162 (100).

b. (1N)-4-n-Butoxyphenylsulfonyl-(2R)-N-hydroxycarboxamido-(4S)-[(1N)-methyl-3-imidazolyl]-sulfonylaminopyrrolidine: The starting ester 50a (236 mg, 0.471 mmole) is converted to the title compound and chromatographed as described for compound 45b to give 262 mg of yellow oil which was further purified by reverse phase prep. HPLC to give pure solid. ESI MS: m/z (rel intensity) 502.2 ($M^++H$).

Example 51 a. (1N)-4-Methoxyphenylsulfonyl-(2R)-carbomethoxy-(4S)-N-(3-pyridyl)-methyl-aminopyrrolidine: The primary amine 42b (810 mg, 2.6 mmole) is N-alkylated with 3-pyridine-carboxaldehyde (270 µL, 2.86 mmole) as described for compound 44a to give the desired amine as a clear gum which is purified over flash silica gel with EtOAc:MeOH (1:0 to 9:1) to give white solid. CI MS: m/z (rel intensity) 406 ($M^+$+H, 100), 236 (45), 234 (48).

b. (1N)-4-Methoxyphenylsulfonyl-(2R)-carbomethoxy-(4S)-N,N-(3-pyridylmethyl)-(methanesulfonyl)-aminopyrrolidine: The secondary amine 51a (7.80 mg, 19.3 mmole) is taken in 85 mL of methylene chloride and 11 mL of triethyl amine with a catalytic amount of 2,5-dimethylamino-pyridine and treated with methane-sulfonyl chloride (4.5 mL, 57.8 mmole) at rt. The mixture is allowed to stir for 16 hr and then adsorbed onto silica, evaporated to dryness, and eluted through a column of flash silica with EtOAc:MeOH (0:1 to 9:1) to give the title compound as a yellow foamy solid. CI MS: m/z (rel intensity) 484 ($M^+$+H, 30), 406 (10), 314 (40), 234 (90), 187 (42), 102 (100).

c. (1N)-4-Methoxyphenylsulfonyl-(2R)-N-hydroxycarbo-xamido-(4S)-N,N-(3)-pyridylmethyl)-(methanesulfonyl)-aminopyrrolidine: The starting ester 51b (6.33 g, 13.1 mmole) is converted to the relative hydroxamic acid as described for compound 45b and eluted through flash silica with EtOAc:MeOH (1:0 to 4:1) to give the title compound as a white powder. ESI MS: m/z (rel intensity) 484.9 ($M^+$+H, 100), 506.9 ($M^+$+$NH_3$, 10).

Example 52 a. (1N)-4-Methoxyphenylsulfonyl-(2R)-carbomethoxy-(4S)-bis-(N-methanesulfonyl)-amino-pyrrolidine: The title compound is isolated from the crude mixture in 48a. ESI MS: m/z (rel intensity) 488.3 ($M^+$+$NH_4^+$, 15), 471.3 ($M^+$+H, 10).

b. (1N)-4-Methoxyphenylsulfonyl-(2R)-N-hydroxycarbo-xamido-(4S)-bis-(N-methanesulfonyl)-amino-pyrrolidine: The starting ester 52a (94 mg, 0.20 mmole) is converted to the relative hydroxamic acid as described for compound 48b and eluted through flash silica with EtOAc:MeOH (1:0 to 5:1) to give the title compound as a white solid. ESI MS: m/z (rel intensity) 489.3 ($M^+$+$NH_4^+$, 55), 472.3 ($M^+$+H, 100).

Example 53 a. (1N)-4-Methoxyphenylsulfonyl-(2R)-carbomethoxy-(4S)-N-(methane-sulfonyl)-propyl-aminopyrrolidine The starting amine 44a (783 mg, 2.20 mmole) was converted to the title compound as described for 48a. ESI MS: m/z (rel intensity) 452 (M+$NH_4^+$), 435 ($M^+$+H, 75), 265 (100), 155 (75), 126 (40).

b. (1N)-4-Methoxyphenylsulfonyl-(2R)-N-hydroxycarbo-xamido-(4S)-N-(methanesulfonyl)-propyl-aminopyrrolidine The starting ester 53a (614 mg, 1.41 mmole) was converted to the title compound as described for 48b. ESI MS: m/z (rel intensity) 452.9 (M+$NH_4^+$, 100), 435.8 ($M^+$+H, 55).

Example 54 a. (1N)-4-Methoxyphenylsulfonyl-(2R)-carbomethoxy-(4S)-4-methoxyphenyl-sulfonylamino-pyrrolidine: The primary amine 42b (400 mg, 1.27 mmole) is converted to the title compound with p-methoxybenzenesulfonyl chloride (316 mg, 1.53 mmole) as described for compound 48a. $CI^+$ MS: m/z (rel intensity) 502 ($M^+$+$NH_4^+$, 12), 485 ($M^+$+H, 10), 315 (100).

b. (1N)-4-Methoxyphenylsulfonyl-(2R)-N-hydroxycarbo-xamido-(4S)-4-methoxyphenyl-sulfonylamino-pyrrolidine: The starting ester 54a (480 mg, 0.99 mmole) is converted to the relative hydroxamic acid as described for compound 48b and eluted through flash silica with EtOAc:MeOH:$HCO_2$H (1:0:0 to 4:1:0.1) to give the title compound as a white solid which was recrystallized from acetonitrile:water to give white crystals. ESI MS: m/z (rel intensity) 486 ($M^+$+H, 100), 503 ($M^+$+$NH_4$, 30).

Example 55 a. (1N)-4-Methoxyphenylsulfonyl-(2R)-carbomethoxy-(4S)-(-1-oxyhexyl)-aminopyrrolidine: The primary amine 42b (500 mg, 1.59 mmole) is converted to the title compound with hexanoyl chloride (268 µL, 1.91 mmole) as described for compound 48a. ESI MS: m/z (rel intensity) 413.2 ($M^+$+H, 70), 430.2 ($M^+$+$NH_4$, 100).

b. (1N)-4-Methoxyphenylsulfonyl-(2R)-N-hydroxycarbo-xamido-(4S)-(-1-oxyhexyl)-aminopyrrolidine: The starting ester 55a (560 mg, 1.35 mmole) is converted to the relative hydroxamic acid as described for compound 48b and eluted through flash silica with EtOAc:MeOH:$HCO_2$H (1:0:0 to 4:1:0.1) to give the title compound as a pale orange, viscous sap which would not solidify. ESI MS: m/z (rel intensity) 431.4 ($M^+$+$NH_4^+$, 25), 414.4 ($M^+$+H, 35), 102 (100).

Example 56 a. (1N)-4-Methoxyphenylsulfonyl-(2R)-carbomethoxy-(4S)-p-biphenylyl-aminopyrrolidine: The primary amine 42b (1.00 g, 3.19 mmole) is converted to the title compound with 4-biphenyl chloride (761 mg, 3.51 mmole) as described for compound 48a. $CI^+$ MS: m/z (rel intensity) 4.95 $M^+$+H, 30), 325 (100), 198 (55), 155 (27).

b. (1N)-4-Methoxyphenylsulfonyl-(2R)-hydroxycarbo-xamido-(4S)-p-biphenylylaminopyrrolidine: The starting ester 56a (200 mg, 0.404 mmole) is converted to the relative hydroxamic acid as described for compound 48b and eluted through flash silica with EtOAc:MeOH(1:0:0 to 9:1) to give 129 mg (65%) of the title compound. ESI MS: m/z (rel intensity) 496.0 ($M^+$+H, 100), 513.0 (M+$NH_4^+$, 60), 517.8 ($M^+$+Na, 15).

Example 57 a. (1N)-4-Methoxyphenylsulfonyl-(2R)-carbomethoxy-(4S)-methylcarboxamyl-aminopyrrolidine: The primary amine 42b (470 mg, 1.49 mmole) is taken in 4 mL of dioxane with 1 mL of triethyl amine and a catalytic amount of DMAP and then treated with methyl isocyanate (106 µL, 1.80 mmole) and stirred for 16 hrs at rt. The mixture is then partitioned between EtOAc and 1N HCl and the organic layer is washed with brine, dried over $MgSO_4$, filtered and evaporated. The residue is then chromatographed over flash silica with hexane:EtOAc (1:2 to 0:1) to give white solid. $CI^+$ MS: m/z (rel intensity) 389 ($M^+$+$NH_4^+$, 5), 372 ($M^+$+H, 25), 202 (100).

b. (1N)-4-Methoxyphenylsulfonyl-(2R)-hydroxycarbo-xamido-(4S)-methyl-carboxamyl-aminopyrrolidine: The starting ester 57a (351 mg, 0.95 mmole) is converted to the relative hydroxamic acid as described for compound 48b and eluted through flash silica with EtOAc:MeOH (8:1) to give the title compound as a white solid which was recrystallized from acetonitrile:water to give white crystals. ESI MS: m/z (rel intensity) 411.0 ($M^+$+K, 30), 373.1 ($M^+$+H, 100), 316 (32).

Example 58 a. (1N)-4-Methoxyphenylsulfonyl-(2R)-carbomethoxy-(4S)-N-(.-oxo-2R-benzyloxy-propyl)-aminopyrrolidine: The starting amine 42b (465 mg, 1.48 mmole), and the starting L-o-benzyllactic acid (319 mg, 1.78 mmole) is taken in 4 mL of DMF in the presence of 1.5 mL of N-methylmorpholine, EDAC (568 mg, 2.96 mmole) and HOBT (599 mg, 4.44 mmole). The resulting mixture is stirred at rt for 16 hr and then partitioned between 1N HCl and EtOAc. The organic layer is then washed 1× with dil NaHCO$_3$, 1× with brine, dried over MgSO$_4$, filtered and evaporated. The crude residue is then chromatographed with hexane:EtOAc (2:1 to 1:3) to give the title compound. ESI MS: m/z (rel intensity) 477.2 (M$^+$+H, 100), 494.2 (M$^+$+NH$_3$, 10).

b. (1N)-4-Methoxyphenylsulfonyl-(2R)-N-hydroxycarboxamido-(4S)-N-(1-oxo-2R-benzyloxypropyl)-aminopyrrolidine: The starting methylester 58b (480 mg, 1.01 mmole) is taken in 2 mL of methanol, treated with NH$_2$OK (2.5 mL, 1.25 M in methanol, solution prepared as described in Fieser and Fieser, Vol 1, p 478) and stirred overnight. The following morning, dry silica (3 mL) is added to the mixture and the solvent removed under vacuum. The dry silica is poured on the top of a flash silica gel column which is subsequently eluted with EtOAc:MeOH (1:0Ø4:1) to give 338 mg (70%) of a white foamy solid. ESI MS: m/z (rel intensity) 478.3 (M$^+$+H, 100), 500.2 (M$^+$+Na, 12).

Example 59 a. 2R-benzyloxy-3-phenylproionic acid: Sodium hydride (2.9 g, 120 mmole), is washed 2 times with hexane and covered with 50 mL of DMF. The starting L-3-phenyllactic acid (5 g, 30.1 mmole) is then added in portions and, after fizzing ceased, the mixture is heated to 55° C. for 1 hr. The mixture is then cooled to 0° C. and benzyl bromide (4.3 mL, 36.1 mmole) is added dropwise. The mixture is heated to 60° C. for 3 hr and then partitioned between hexane:EtOAc (1:1) and 1N HCl. The organic layer is washed with brine, dried over MgSO4, filtered and evaporated. The residue is chromatographed over flash silica with hexane:EtOAc (9:1 to 0:1) to give a colorless oil. ESI MS: m/z (rel intensity) 274.3 (M$^+$+NH$_3$, 100).

b. (1N)-4-Methoxyphenylsulfonyl-(2R)-carbomethoxy-(4S)-N-(1-oxo-2R-benzyloxy-3-phenylpropyl)-aminopyrrolidine: The starting amine 44a (800 mg, 2.55 mmole), and the starting benzyl lactic acid 59a (784 mg, 3.06 mmole) is taken in 5 mL of DMF in the presence of 1 mL of N-methylmorpholine, EDAC (979 mg, 5.10 mmole) and HOBT (1.03 mg, 7.65 mmole). The resulting mixture is stirred at rt for 16 hr and then partitioned between 1N HCl and EtOAc. The organic layer is then washed 1× with dil NaHCO$_3$, 1× with brine, dried over MgSO$_4$, filtered and evaporated. The crude residue is then chromatographed with hexane:EtOAc (8:1 to 1:1) to give the title compound.

ESI MS: m/z (rel intensity) 553.2 (M$^+$+H, 100), 570.3 (M$^+$+NH$_3$, 18).

c. (1N)-4-Methoxyphenylsulfonyl-(2R)-N-hydroxycarboxamido-(4S)-N-(1-oxo-2R-benzyloxy-3-phenylpropyl)-aminopyrrolidine: The starting methylester 59b (700 mg, 1.27 mmole) is taken in 2 mL of methanol, treated with NH$_2$OK (2.5 mL, 1.25 M in methanol, solution prepared as described in Fieser and Fieser, Vol 1, p 478) and stirred overnight. The following morning, dry silica (3 mL) is added to the mixture and the solvent removed under vacuum. The dry silica is poured on the top of a flash silica gel column which is subsequently eluted with hexane:EtOAc (1:1Ø0:1) to give a white foamy solid. ESI MS: m/z (rel intensity) 553.3 (M$^+$+H, 100), 576.3 (M$^+$+Na, 23).

Example 60 a. (1N)-4-Methoxyphenylsulfonyl-(2R)-carbomethoxy-(4S)-N-(1-oxo-2R-benzyloxy-propyl)-propyl-aminopyrrolidine: The starting amine 44a (636 mg, 1.79 mmole), and the starting L-o-benzyllactic acid (390 mg, 2.15 mmole) is taken in 5 mL of DMF in the presence of 1 mL of N-methylmorpholine, EDAC (687 mg, 3.58 mmole) and HOBT (762 mg, 5.37 mmole). The resulting mixture is stirred at rt for 16 hr and then partitioned between 1N HCl and EtOAc. The organic layer is then washed 1× with dil NaHCO$_3$, 1× with brine, dried over MgSO$_4$, filtered and evaporated. The crude residue is then chromatographed with hexane:EtOAc (8:1 to 1:1) to give the title compound. ESI MS: m/z (rel intensity) 595.2 (M$^+$+H, 100).

b. (1N)-4-Methoxyphenylsulfonyl-(2R)-carbomethoxy-(4S)-N-(1-oxo-2R-hydroxy-propyl)-propyl-aminopyrrolidine: The starting ether 60a (700 mg, 1.35 mmole) is taken in 25 mL of methanol with catalytic 10% Pd—C and H2SO4 and hydrogenated for 3 hrs at 54 psi in a Parr apparatus. The material is then filtered through a pad of celite, evaporated to dryness and chromatographed over flash silica to give a clear gum. ESI MS: m/z (rel intensity) 429.3 (M$^+$+H, 100), 446.3 (M$^+$+NH$_3$, 12).

c. (1N)-4-Methoxyphenylsulfonyl-(2R)-carbomethoxy-(4S)-N-(1-oxo-2R-hydroxypropyl)-propyl-aminopyrrolidine: The starting methylester 60b (331 mg, 0.771 mmole) is taken in 1 mL of methanol, treated with NH$_2$OK (1.23 mL, 1.25 M in methanol, solution prepared as described in Fieser and Fieser, Vol 1, p 478) and stirred overnight. The following morning, dry silica (3 mL) is added to the mixture and the solvent removed under vacuum. The dry silica is poured on the top of a flash silica gel column which is subsequently eluted with hexane:EtOAc (1:1Ø0:1) to give a white foamy solid. ESI MS: m/z (rel intensity) 519.3 (M$^+$+H, 100), 536.3 (M$^+$+NH$_3$, 60).

Example 61 a. (1N)-4-Methoxyphenylsulfonyl-(2R)-carbomethoxy-(4S)-N,N-(1-oxo-2R-benzyloxy-3-phenylpropyl)-propyl-aminopyrrolidine: The acid 59a (530 mg, 1.68 mmole) was taken in 15 mL of CH$_2$Cl$_2$ and treated with oxalyl chloride (293 µL, 3.37 mmole). A catalytic drop of DMF was added and the mixture was stirred for a total of 3.5 hrs and then evaporated to dryness. The residue was taken in 15 mL of CH$_2$Cl$_2$ and added to a solution of the starting amine 44a (449 mL, 1.26 mmole) in 10 mL of CH$_2$Cl$_2$ and 2 mL of triethyl amine. The resulting solution was stirred for 16 hrs. and then partitioned between EtOAc and 1N HCl. The organic layer was washed 1 time with 1 N HCl, 2 times with NaHCO$_3$, 1 time with brine, dried over MgSO$_4$, filtered and evaporated to give 740 mg of crude gum. This is then chromatographed over flash silica with hexane:EtOAc (4:1 to 1:2) to give a pale yellow gum. ESI MS: m/z (rel intensity) 595.2 (M$^+$+H, 100)

b. (1N)-4-Methoxyphenylsulfonyl-(2R)-carbomethoxy-(4S)-N-(1-oxo-2R-hydroxy-3-phenylpropyl)-propyl-aminopyrrolidine: The starting ether 61a (480 mg, 0.807 mmole) is taken in 20 mL of methanol with catalytic 10% Pd—C and H$_2$SO$_4$ and hydrogenated for 16 hrs at 50 psi in a Parr apparatus. The material is then filtered through a pad of celite, evaporated to dryness and chromatographed over flash silica with EtOAc to give a clear gum. ESI MS: m/z (rel intensity) 505.3 (M⁺+H, 100), 522.3 (M⁺+NH₃, 15).

c. (1N)-4-Methoxyphenylsulfonyl-(2R)-N-hydroxycarboxamido-(4S)-N-(1-oxo-2R-hydroxy-3-phenylpropyl)-propyl-aminopyrrolidine: The starting methylester 61b (307 mg, 0.608 mmole) is taken in 1 mL of methanol, treated with NH₂OK (1.23 mL, 1.25 M in methanol, solution prepared as described in Fieser and Fieser, Vol 1, p 478) and stirred overnight. The following morning, dry silica (3 mL) is added to the mixture and the solvent removed under vacuum. The dry silica is poured on the top of a flash silica gel column which is subsequently eluted with hexane:EtOAc (1:1Ø0:1) to give a white foamy solid. ESI MS: m/z (rel intensity) 506.3 (M⁺+H, 100), 526.3 (M⁺+Na, 12).

Examples 62–63

In the following examples W and Z are hydrogen, and Y is OH, n is 1, Ar is substituted or unsubstituted phenyl, and X and Q refer to substituents on the phenyl ring:

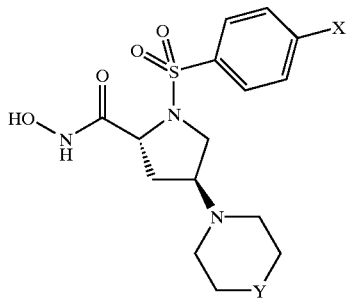

| Example | X | Y |
|---------|------|-----|
| 62 | OMe | CH₂ |
| 63 | OnBu | CH₂ |
| 64 | OMe | O |
| 65 | OnBu | O |
| 66 | OMe | SO₂ |
| 67 | OnBu | SO₂ |

Example 62 a. (1N)-4-Methoxyphenylsulfonyl-(2R)-carbomethoxy-(4S)-1-piperidyl-pyrrolidine: The starting amine 42b (1.00 g, 3.19 mmole) is dissolved in 10 mL of methanol and stirred for 16 hrs in the presence of glutonic dialdehyde (961 mg, 50 wt % in water, 4.8 mmole), sodium cyanoborohydride (503 mg, 8 mmole), sodium acetate (1 g) and 1 mL of acetic acid. The mixture is evaporated to dryness and then partitioned between dil. NaHCO₃ and EtOAc and the organic layer is washed 2 times with NaHCO₃, 1 time with brine, dried over MgSO₄, filtered and evaporated to give a clear colorless glass which is chromatographed over flash silica with hexane:EtOAc (4:1 to 1:1) to give the desired product as a glear glass. ESI MS: m/z (rel intensity) 383 (M⁺+H, 100), 211 (38).

b. (1N)-4-Methoxyphenylsulfonyl-(2R)-N-hydroxycarboxamido-(4S)-1-piperidyl-pyrrolidine: The starting methylester 62a (1.00 g, 2.62 mmole) is taken in 3 mL of methanol, treated with NH₂OK (4 mL, 1.25 M in methanol, solution prepared as described in Fieser and Fieser, Vol 1, p 478) and stirred overnight. The following morning, dry silica (4 mL) is added to the mixture and the solvent removed under vacuum. The dry silica is poured on the top of a flash silica gel column which is subsequently eluted with EtOAc:MeOH (1:0Ø4:1) to give a pale orange solid. ESI MS: m/z (rel intensity) 384 (M⁺+H, 100), 406 (M⁺+Na, 82), 422 (M⁺+K, 65).

Example 63 a. (1N)-4-n-Butoxyphenylsulfonyl-(2R)-carbomethoxy-(4S)-1-piperidyl-pyrrolidine: The starting amine 43c (1.06 g, 1.88 mmole) is taken in 10 mL of DMF and 1.5 mL of NEt₃ and treated with 2 mL of 2-bromoethyl ether. The resulting mixture is then heated to 60° C. for 16 hr and partitioned between dil Na₂CO₃ and EtOAc. The organic layer is then dried over MgSO₄, filtered and evaporated. The crude residue was chromatographed over flash silica with Hexane:EtOAc (1:1 to 0:1) to give the title compound as a clear oil. ESI MS: m/z (rel intensity) 425 (M⁺+H).

b. (1N)-4-n-Butoxyphenylsulfonyl-(2R)-N-hydroxycarboxamido-(4S)-1-piperidyl-pyrrolidine: The starting methylester 63a (851 mg, 2.01 mmole) is taken in 1 mL of methanol, treated with NH₂OK (0.381 mL, 0.86 M in methanol, solution prepared as described in Fieser and Fieser, Vol 1, p 478) and stirred overnight. The following morning, dry silica (2 mL) is added to the mixture and the solvent removed under vacuum. The dry silica is poured on the top of a flash silica gel column which is subsequently eluted with EtOAc:MeOH (1:0Ø9:1) to give 543 mg (64%) of a pale orange solid. This was recrystallized from hexane:EtOAc to give pale orange solid. ESI MS: m/z (rel intensity) 426.1 (M⁺+H).

Example 64 a. (1N)-4-Methoxyphenylsulfonyl-(2R)-carbomethoxy-(4S)-morpholinopyrrolidine: The starting amine 42b (590 mg, 1.88 mmole) is taken in 4 mL of DMF and 1 mL of NEt₃ and treated with 1 mL Of 2-bromoethyl ether. The resulting mixture is then heated to 60° C. for 3 hr and partitioned between dil NaCO₃ and EtOAc. The organic layer is then dried over MgSO₄, filtered and evaporated. The crude residue was chromatographed over flash silica with EtOAc:MeOH (9:1) to give the title compound as a white solid. ESI MS: m/z (rel intensity) 385.1 (M⁺+H).

b. (1N)-4-Methoxyphenylsulfonyl-(2R)-N-hydroxycarboxamido-(4S)-morpholino-pyrrolidine: The starting methylester 64a (310 mg, 0.86 mmole) is treated with NH₂OK (2 mL, 1.25 M in methalol) in 4 mL mL of methanol as described for 63b to give material which is puffed to a white solid under vacuum and not recrystallized. ESI MS: m/z (rel intensity) 386.1 (M⁺+H, 100), 565.1 (12), 424.0 (15), 408.1 (M+NH₄⁺, 7), 218.1 (20), 202.1 (13).

Example 65 a. (1N)-4-n-Butoxyphenylsulfonyl-(2R)-carbomethoxy-(4S)-morpholinopyrrolidine: The starting amine 43c (7.2 g, 20.2 mmole), was taken in 50 mL of DMF and 15 mL of Et₃N with 2-bromoethyl ether and converted to the title compound as described for compound 63a. ESI MS: m/z (rel intensity) 427.18 (M⁺+H).

b. (1N)-4-n-Butoxyphenylsulfonyl-(2R)-N-hydroxycarboxamido-(4S)-morpholino-pyrrolidine: The starting methylester 65a (6.5 g, 15.2 mmole) is treated with NH₂OK (24 mL, 1.25 M in methalol) in 20 mL mL of methanol as described for 63b to give material which is puffed to a white solid under vacuum and not recrystallized. ESI MS: m/z (rel intensity) 428.08 (M⁺+H, 100), 450.07 (M⁺+Na, 8), 465.99 (M⁺+K, 15).

Example 66 a. (1N)-4-Methoxyphenylsulfonyl-(2R)-carbomethoxy-(4S)-(4,4-dioxythio-morpholino)-pyrrolidine: The starting amine 42b (560 mg, 1.79 mmole), was taken in 10 mL of DMF and 1 mL of N-methylmorpholine with di-2-bromoethylsulfone (500 mg, 1.79 mmole) and converted to the title compound as described for compound 63a. ESI MS: m/z (rel intensity) 433.1 (M⁺+H).

b. (1N)-4-Methoxyphenylsulfonyl-(2R)-N-hydroxycarboxamido-(4S)-(4,4-dioxy-thiomorpholino)-pyrrolidine: The starting methyl ester 66a (420 mg, 976 mmole) was converted to the title compound as described for compound 63b. This material was then recrystallized from EtOAc:methanol to give first crop crystals and second crop crystals. ESI MS: m/z (rel intensity) 434.0 (M⁺+H, 100), 456.0 (M⁺+Na, 32).

Example 67 a. (1N)-4-n-Butoxyphenylsulfonyl-(2R)-carbomethoxy-(4S)-(4,4-dioxythio-morpholino)-pyrrolidine: The starting amine 43c (1.00 g, 2.81 mmole), was taken in 5 mL of DMF and 2 mL of N-methylmorpholine with di-2-bromoethylsulfone (750 mg, 2.68 mmole) and converted to the title compound as described for compound 63a. ESI MS: m/z (rel intensity) 475.0 (M⁺+H)

b. (1N)-4-n-Butoxyphenylsulfonyl-(2R)-N-hydroxycarboxamido-(4S)-(4,4-dioxythiomorpholino)-pyrrolidine: The starting methylester 67a (1.01 g, 2.83 mmole) is treated with NH₂OK (4 mL, 1.25 M in methalol) in 4 mL of methanol as described for 63b to give material which is puffed to a white solid under vacuum and not recrystallized. ESI MS: m/z (rel intensity) 476.1 (M⁺+H, 100), 498.1 (M⁺+Na, 22).

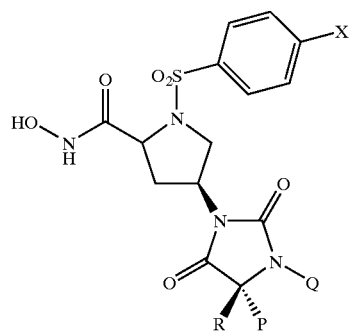

| Example | X | Q | R | P |
|---|---|---|---|---|
| 68 | OMe | Me | H | H |
| 69 | OnBu | Me | H | H |
| 70 | OMe | CH₂CH=CH₂ | H | H |
| 71 | OnBu | H | CH₃ | CH₃ |
| 72 | OnBu | H | H | CH₃ |
| 73 | O(CH₂)₂OMe | CH₃ | H | H |
| 74 | OPh | CH₃ | H | H |
| 75 | OCH(CH₃)₂ | CH₃ | H | H |

Example 68 a. (1N)-4-Methoxyphenylsulfonyl-(2R)-carbomethoxy-(4S)-1N-(3N-methylhydantoyl)-pyrrolidine: Diethylazodicarboxylate (1.8 mL, 11.42 mmole) is added to a stirred solution of the starting alcohol 1a (3.0 g, 9.51 mmole), triphenylphosphene (3.74 g, 9.51 mmole), and 1-methylhydantoin (1.3 g, 11.42 mmole) in 30 mL of CH₂Cl₂ and stirred for 16 hrs at rt. The mixture is then chromatographed over flash silica with hexane and then hexane:EtOAc (1:1) to give colorless glass which is recrystallized from methanol to give a white powder. ESI MS: m/z (rel intensity) 412.1 (M⁺+H, 100), 429.1 (M⁺+NH₃, 45).

b. (1N)-4-Methoxyphenylsulfonyl-(2R)-N-hydroxycarboxamido-(4S)-1N-(3N-methylhydantoyl)-pyrrolidine: The starting methyl ester 68a (500 mg, 1.22 mmole) is taken in 7 mL of methanol/tetrahydrofuran (1:1), and treated with NH₂OK (2.5 mL, 1.25M in methanol) and stirred overnight. The following morning, dry silica (1.5 mL) is added to the mixture and the solvent removed under vacuum. The dry silica is poured on top of a flash silica column which is subsequently eluted with ethyl acetate followed with ethyl acetate (9:1) to give a clear glass which is puffed to a foamy solid by slight heating under vacuum. The product is recrystallized from cold methanol to give a white powder. ESI MS: m/z (rel intensity) 413.0 (M⁺+H, 100), 430.0(M⁺+NH₃, 55).

Example 69 a. (1N)-4-n-Butoxyphenylsulfonyl-(2R)-carbomethoxy-(4S)-1-(3N-methyl-hydantoyl)-pyrrolidine: Diethylazodicarboxylate (1.6 mL, 10.24 mmole) is added to a stirred solution of the starting alcohol 29a (3.05 g, 8.53 mmole), triphenylphosphine (3.36 g, 12.80 mmole), and 1-methylhydantoin (1.17 mg, 10.24 mmole) in 60 mL of CH₂Cl₂ and stirred for 16 hrs at rt. The mixture is then chromatographed over silica with hexane followed by hexane:EtOAc (1:1) and finally with EtOAc to give a colorless gum. The product was recrystallized from EtOAc-hexane to give a white powder. ESI MS: m/z (rel intensity) 454.05 (M⁺+H, 100), 471.05 (M⁺+NH₃, 30).

b. (1N)-4-n-butoxyphenylsulfonyl-(2R)-N-hydroxycarboxamido-(4S)-1N-(3N-methylhydantoyl)-pyrrolidine: The starting methyl ester 69a (500 mg, 1.22 mmole) is taken in 7 mL of methanol/tetrahydrofuran (1:1), and treated with NH₂OK (2.5 ml, 1.25 M in methanol) and stirred overnight. The following morning, dry silica (1.5 ml) is added to the mixture and the solvent removed under vacuum. The dry silica is poured on top of a flash silica column which is subsequently eluted with ethyl acetate followed with ethyl acetate:methanol (9:1) to give a clear glass which is puffed to a foamy solid by slight heating under vacuum. The product is recrystallized from cold methanol to give a white powder. ESI MS: m/z (rel intensity) 455.0 (M⁺+H, 100), 472.0 (M⁺+NH₃, 50).

Example 70 a. (1N)-4-n-butoxyphenylsulfonyl-(2R)-carbomethoxy-(4S)-1N-(3N-allylhydantoyl)-pyrrolidine: Diethylazodicarboxylate (1.1 mL, 6.98 mmole) is added to a stirred solution of the starting alcohol 1a (2.08 g, 5.82 mmole), triphenylphosphine (2.29 g, 8.73 mmole), and 1-allylhydantoin (979 mg, 6.98 mmole) in 40 mL of CH₂Cl₂ and stirred for 16 hrs at rt. The mixture is then chromatographed over silica with hexane:EtOAc (8:2) followed by hexane:EtOAc (1:1) to give a colorless gum. ESI MS: m/z (rel intensity) 480.0 (M⁺+H, 100), 497.0 (M⁺+NH₃, 20).

b. (1N)-4-n-butoxyphenylsulfonyl-(2R)-N-hydroxycarboxamido-(4S)-1N-(3N-allyl-hydantoyl)-pyrrolidine: The starting methyl ester 70a (549 mg, 1.15 mmole) is taken in 2 mL of methanol/tetrahydrofuran (1:1), and treated with NH$_2$OK (1.5 mL, 1.25 M in methanol) and stirred overnight. The following morning, dry silica (1.5 mL) is added to the mixture and the solvent removed under vacuum. The dry silica is poured on top of a flash silica column which is subsequently eluted with ethyl acetate followed with ethyl acetate:methanol (8:2) to give a clear glass which is purified to a foamy solid by slight heating under vacuum. The product was recrystallized from cold methanol to give a of white powder. ESI MS: m/z (rel intensity) 481.2 (M$^+$+H, 100), 498.2(M$^+$+NH$_3$, 60).

Example 71 a. (1N)-4-n-butoxyphenylsulfonyl-(2R)-carbomethoxy-(4S)-1N-(4-dimethylhydantoyl)-pyrrolidine: Diethylazodicarboxylate (0.530 mL, 3.36 mmole) is added to a stirred solution of the starting alcohol 29a (1.00 g, 2.80 mmole), triphenylphosphine (1.10 g, 4.20 mmole), and 5,5-dimethylhydantoin (430 mg, 3.36 mmole) in 20 mL of CH$_2$Cl$_2$ and stirred for 16 hrs at rt. The mixture is then chromatographed over silica with hexane:EtOAc (8:2) followed by hexane:EtOAc (1:1) to give a colorless gum. ESI MS: m/z (rel intensity) 468.1 (M$^+$+H, 100), 485.1 (M$^+$+NH$_3$, 30).

b. (1N)-4-n-butoxyphenylsulfonyl-(2R)-N-hydroxycarboxamido-(4S)-1N-(4-dimethylhydantoyl)-pyrrolidine: The starting methyl ester 71a (754 mg, 1.61 mmole) is taken in 2 mL of methanol/tetrahydrofuran (1:1), and treated with NH$_2$OK (2.0 mL, 1.25M in methanol) and stirred overnight. The following morning, dry silica (1.5 mL) is added to the mixture and the solvent removed under vacuum. The dry silica is poured on top of a flash silica column which is subsequently eluted with hexane:ethyl acetate (1:1) followed with hexane:ethyl acetate (2:8) and finally with ethyl acetate:methanol (8:2) to give a clear glass which is puffed to a foamy solid by slight heating under vacuum. The product is recrystallized from cold methanol to give the title compound as a white powder. ESI MS: m/z (rel intensity) 469.0 (M$^+$+H, 100), 486.0 (M$^+$+NH$_3$, 10).

Example 72 a. (1N)-4-n-butoxyphenylsulfonyl-(2R)-carbomethoxy-(4S)-1N-(4S-methyl-hydantoyl)-pyrrolidine: Diethylazodicarboxylate (0.530 mL, 3.36 mmole) is added to a stirred solution of the starting alcohol 29a (1.00 g, 2.80 mmole), triphenylphosphine (1.10 g, 4.20 mmole), and (L)-5-methylhydantoin (383 mg, 3.36 mmole) in 20 mL of CH$_2$Cl$_2$ and stirred for 16 hrs at rt. The mixture is then chromatographed over silica with hexane:EtOAc (8:2) followed by hexane:EtOAc (1:1) to give a colorless gum. This is then repurified over a second column eluting first with hexane:EtAcO (1:1) followed by EtOAc:hexane (8:2). 1H NMR showes a mitsunobu impurity (20%) remaining after two column purifications and the material is carried forward to the next step without further purification. ESI MS: m/z (rel intensity) 454.0 (M$^+$+H, 100), 471.0 (M$^+$+NH$_3$, 20).

b. (1N)-4-n-butoxyphenylsulfonyl-(2R)-N-hydroxycarboxamido-(4S)-1N-(4S-methyl-hydantoyl)-pyrrolidine: The starting methyl ester 72a (497 mg, 1.10 mmole) is taken in 2 mL of methanol/tetrahydrofuran (1:1), and treated with NH$_2$OK (1.5 mL, 1.25M in methanol) and stirred overnight. The following morning, dry silica (1.5 mL) is added to the mixture and the solvent removed under vacuum. The dry silica is poured on top of a flash silica column which is subsequently eluted with ethyl acetate followed with ethyl acetate:methanol (9:1) to give a clear glass which is puffed to a foamy solid by slight heating under vacuum. The product is recrystallized from cold methanol to give the title compound as a of white powder. ESI MS: m/z (rel intensity) 455.0 (M$^+$+H, 100), 472.0 (M$^+$+NH$_3$, 30).

Example 73 a. (1N)-4-(2-methoxyethoxy)phenylsulfonyl-(2R)-carbomethoxy-(4S)-1N-(3N-methylhydantoyl)-pyrrolidine: Diethylazodicarboxylate (0.546 mL, 3.47 mmole) is added to a stirred solution of the starting alcohol 34b (1.04 g, 2.89 mmole), triphenylphosphine (1.14 g, 4.34 mmole), and 1-methylhydantoin (396 mg, 3.47 mmole) in 20 mL of CH$_2$Cl$_2$ and stirred for 16 hrs at rt. The mixture is then chromatographed over silica with hexane:EtOAc (1:1) followed by hexane:EtOAc (2:8) to give a colorless gum. ESI MS: m/z (rel intensity) 456.14 (M$^+$+H, 100), 473.15 (M$^+$+NH$_3$, 10).

b. (1N)-4-(2-methoxyethoxy)-phenylsulfonyl-(2R)-N-hydroxycarboxanido-(4S)-1N-(3N-methylhydantoyl)-pyrrolidine: The starting methyl ester 73a (725 mg, 1.59 mmole) is taken in 2 mL of methanol/tetrahydrofuran (1:1), and treated with NH$_2$OK (2 mL, 1.25 M in methanol) and stirred overnight. The following morning, dry silica (1.5 mL) is added to the mixture and the solvent removed under vacuum. The dry silica is poured on top of a flash silica column which is subsequently eluted with ethyl acetate followed with ethyl acetate:methanol (8:2) to give a clear glass which is purified to a foamy solid by slight heating under vacuum. The product was recrystallized from cold methanol to give the title compound as a white powder. ESI MS: m/z (rel intensity) 457.08 (M$^+$+H, 100), 474.09 (M$^+$+NH$_3$, 60).

Example 74 a. (1N)-4-phenoxyphenylsulfonyl-(2R)-carbomethoxy-(4S)-1N-(3N-methylhydantoyl)-pyrrolidine: Diethylazodicarboxylate (0.570 mL, 3.62 mmole) is added to a stirred solution of the starting alcohol 35b (1.14 g, 3.02 mmole), triphenylphosphine (1.19 g, 4.53 mmole), and 1-methylhydantoin (413 mg, 3.62 mmole) in 20 mL of CH$_2$Cl$_2$ and stirred for 16 hrs at rt. The mixture is then chromatographed over silica with hexane:EtOAc (8:2) followed by hexane:EtOAc (1:1) with product eluting with Hexane:EtOAc (2:8) to give a colorless gum. ESI MS: m/z (rel intensity) 474.03 (M$^+$+H, 100), 491.03 (M$^+$+NH$_3$, 20).

b. (1N)-4-phenoxyphenylsulfonyl-(2R)-N-hydroxycarboxamido-(4S)-1N-(3N-methylhydantoyl)-pyrrolidine: The starting methyl ester (1.50 g, 1.59 mmole) is taken in 10 mL of methanol/tetrahydrofuran (1:1), and treated with NH$_2$OK (5 mL, 1.25M in methanol) and stirred overnight. The following morning, dry silica (5 mL) is added to the mixture and the solvent removed under vacuum. The dry silica is poured on top of a flash silica column which is subsequently eluted with ethyl acetate hexane (1:1), then ethyl acetate followed with ethyl acetate:methanol (8:2) to give a clear glass which is puffed to a foamy solid by slight heating under vacuum. The product is recrystallized from cold methanol to give the title compound as a white powder. ESI MS: m/z (rel intensity) 475.09 (M$^+$+H, 100), 497.07 (M$^+$+NH$_3$, 60).

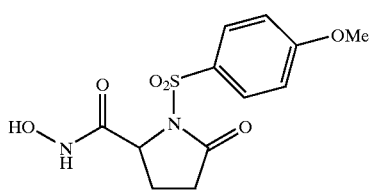

Example 75 a. (±)-(1N)-4-Methoxyphenylsulfonyl-(2R)-carbomethoxy-5-pyrrolidinone: The 2-carboxy-β-lactam starting material (10 g, 77.5 mmoles) is dissolved in 200 mL of methanol at 0° C. followed by the addition of 0.76M diazomethane until the color of the reaction miture remained yellow. The reaction is then stirred for an additional 30 minutes. This is evaporated down to get rid of excess methanol and diazomethane. The yield is quantitative and the product is carried forward without further purification.

The methyl ester produced above (11.08 g, 77.5 mmoles) is dissolved in 500 mL of dry THF at 0° C. followed by the one portion addition of t-butoxide (9.15 g, 77.5 mmoles) and stirred for 1 hour. Next, 4-methoxybenzene sulfonyl chloride (19.2 g, 93.0 mmoles) is added and this stirred over night. The reaction is quenched with saturated sodium bicarbonate until basic and extracted with ether 3 times. The ether layer is washed with 1N HCl, sodium bicarbonate, and ammonium chloride, dried over magnesium sulfate and evaporated done. Chromotography is performed on silica gel using a solvent system of ethyl acetate:hexane (1:1) to give the title compound. CI$^+$ MS: m/z (rel intensity) 314.0 (M$^+$+H, 100).

b. (±)-(1N)-4-Methoxyphenylsulfonyl-(2R)-carboxyl-5-pyrrolidinone: The sulfonated methyl ester 75a (8.5 g, 27.12 mmoles) is dissolved in 60 mL of a THF and methanol (3:1). Lithium hydroxide (2.27 g, 94.9 mmoles) is then added in THF and methanol (3:1). An additional 10 ml of methanol is added to the reaction mixture to improve solubility. The reaction stirred for 3 hours. The reaction is quenched with water and then evaporated down to get rid of the organic solvents. The water layer is extracted one time with ether. Then the water layer is acidified to pH=2 and this is extracted with ethyl acetate 3 times and washed with sodium chloride and dried over magnesium sulfate. This is evaporated down to give give the title compound. CI$^+$ MS: m/z (rel intensity) 300.0 (M$^+$+H, 100).

c. (±)-(1N)-4-Methoxyphenylsulfonyl-(2R)-O-benzyl-N-hydroxycarboxanido-5-pyrrolidinone: The carboxylic acid 75b (1.0 g, 3.3 mmoles) is dissolved in 15 mL of DMF at 0 C. followed by the addition of triethyl amine (1.37 mL, 9.9 mmoles), 4-methylmorpholine N-oxide (1.08 g, 9.9 mmoles), 1-hydroxy-benzotriazole (1.33 g, 9.9 mmoles), and 1-ethyl-3(3-dimethyl-aminopropyl) carbodiimide (0.76 g, 4.01 mmoles). This stirred for 30 minutes followed by the addition of the benzylamine (0.64 g, 4.01 mmoles). The reaction stirred overnight. The reaction is quenched with saturated sodium bicarbonate and then extracted with ethyl acetate 3 times, washed with 1NHCl and sodium chloride, dried over magnesium sulfate and evaporated down. Chromotography is run on silica gel using ethyl acetate and methylene chloride (5:1) to give give the title compound. CI$^+$ MS: m/z (rel intensity) 404.0 (M$^+$+H, 100).

d. (±)-(1N)-4-Methoxyphenylsulfonyl-(2R)-N-hydroxycarboxamido-5-pyrrolidinone: The benzyl protected lactam 75c (0.42 g, 1.04 mmoles) is dissolved in 20 mL of ethyl acetate followed by the addition of palladium on activated carbon (wet) (0.042 g, [10% of weight]). The reaction flask is degassed of all oxygen and then put under hydogen balloon pressure for overnight. After the flask is degassed of hydrogen, the palladium is filtered off through cellite and the ethyl acetate is rotovapped off. The compound is recrystallized with ethyl acetate and hexane to give the title compound. ESI MS: m/z (rel intensity) 314.0 (M$^+$+H, 100).

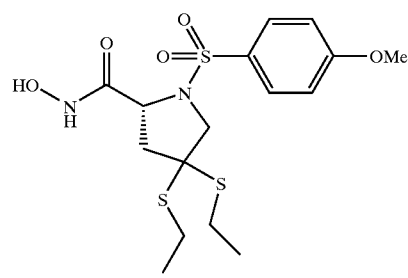

Example 76 a. (1N)-4-Methoxyphenylsulfonyl-(2R)-carbomethoxy-4,4-dithiolethyl-pyrrolidine: The ketone 25a (1.5 g, 4.79 mmol) is dissolved in 30 mL of anhydrous dichloromethane and then ethanethiol (0.53 mL, 7.18 mmol) and borane trifluoride etherate (0.24 mL, 1.91 mmol) is added. The resulting mixture is stirred at room temperature for 14 h. The reaction mixture is quenched by the the addition of 1N sodium hydroxide and then extracted 3 times with ethyl acetate. The organic layers are washed with water and saturated ammonium chloride solution, dried (MgSO$_4$), filtered and concentrated under reduced pressure to give the title compound. CI$^+$ MS: m/z 420 (M$^+$+H)).

b. (1N)-4-Methoxyphenylsulfonyl-(2R)-N-hydroxycarboxamido-4,4-dithiolethylpyrrolidine: The thioketal 76a (0.32 g, 0.89 mmol) is added to a 1.5 M solution of potassium hydroxylamine solution (4.0 mL, prepared as described in Fieser and Fieser, Vol. 1, p. 478.). The reaction mixture is stirred overnight and then acidified with 1N HCl. The resulting mixture is then extracted 3 times with ethyl acetate, dried (MgSO$_4$), filtered and concentrated under reduced pressure. Chromotography was performed on silica gel using EtOAc:hexane:formic acid (1:1:0.1) as the eluent to give the title compound. ESI MS: m/z 421 (M$^+$+H), 443 (M$^+$+Na).

Examples 77–180

The following compounds are made using the methods described and exemplified above. In these Examples R$_1$ is HONH, Z and W are hydrogen, and Y and Ar substitution, as well as ring size are described in the chart below. Hence, a simplified diagram of the molecule exemplified is:

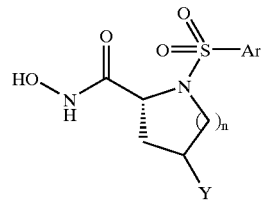

| | Y | Ar | n |
|---|---|---|---|
| Example 78 | —OH | 4-NO$_2$—C$_6$H$_4$— | 1 |
| Example 79 | —OH | 4-i-BuO—C$_6$H$_4$— | 1 |
| Example 80 | —OH | 4-(C$_6$H$_5$)O—C$_6$H$_4$— | 1 |
| Example 81 | —OH | 4-(4-F—C$_6$H$_4$)O—C$_6$H$_4$— | 1 |
| Example 82 | —OH | 4-(4-Cl—C$_6$H$_4$)O—C$_6$H$_4$— | 1 |
| Example 83 | —OH | 4-(4-Br—C$_6$H$_4$)O—C$_6$H$_4$— | 1 |
| Example 84 | —OH | 4-(4-Me-C$_6$H$_4$)O—C$_6$H$_4$— | 1 |
| Example 85 | —OH | 4-(4-MeO—C$_6$H$_4$)O—C$_6$H$_4$— | 1 |
| Example 86 | —OH | 4-(4-CN—C$_6$H$_4$)O—C$_6$H$_4$— | 1 |
| Example 87 | —OH | 4-(4-Me$_2$N—C$_6$H$_4$)O—C$_6$H$_4$— | 1 |
| Example 88 | —OH | 4-EtO—C$_6$H$_4$— | 1 |
| Example 89 | —OH | 4-i-PrO—C$_6$H$_4$— | 1 |
| Example 90 | —OH | 4-n-PrO—C$_6$H$_4$— | 1 |
| Example 91 | —OH | 4-Br—C$_6$H$_4$— | 1 |
| Example 92 | —OH | 4-C$_6$H$_5$—C$_6$H$_4$— | 1 |
| Example 93 | —OH | 4-(4-F—C$_6$H$_5$)—C$_6$H$_4$— | 1 |
| Example 94 | —OH | 4-(4-Cl—C$_6$H$_5$)C$_6$H$_4$— | 1 |
| Example 95 | —OH | 4-(4-Br—C$_6$H$_5$)—C$_6$H$_4$— | 1 |
| Example 96 | —OH | 4-(4-Me$_2$N-C$_6$H$_4$)—C$_6$H$_4$— | 1 |
| Example 97 | —OH | 4-(4-CN—C$_6$H$_4$)—C$_6$H$_4$— | 1 |
| Example 98 | —OH | 4-4-MeO—C$_6$H$_4$)—C$_6$H$_4$ | 1 |
| Example 99 | —OH | 4-(4-C$_5$H$_4$N)O—C$_6$H$_4$— | 1 |
| Example 100 | —OH | 4-(3-C$_5$H$_4$N)O—C$_6$H$_4$— | 1 |
| Example 101 | —OH | 4-(2-C$_5$H$_4$N)O—C$_6$H$_4$— | 1 |
| Example 102 | —OH | C$_6$H$_5$CH$_2$CH$_2$— | 1 |
| Example 103 | —OH | C$_6$H$_5$CH$_2$— | 1 |
| Example 104 | —OH | (4-C$_5$H$_4$N)CH$_2$CH$_2$— | 1 |
| Example 105 | —OH | (2-C$_5$H$_4$N)CH$_2$CH$_2$— | 1 |
| Example 106 | —OH | 4-(C$_6$H$_{11}$)O—C$_6$H$_4$— | 1 |
| Example 107 | —OH | 4-(C$_5$H$_{11}$)O—C$_6$H$_4$— | 1 |
| Example 108 | —OH | 4-(C$_6$H$_{13}$)O—C$_6$H$_4$— | 1 |
| Example 109 | —OH | 4-(CH$_3$OCH$_2$CH$_2$)O—C$_6$H$_4$— | 1 |
| Example 110 | —OH | 5-(2-pyridinyl)-2-thienyl- | 1 |
| Example 111 | —OH | 5-(3-isoxazolyl)-2-thienyl- | 1 |
| Example 112 | —OH | 5-(2-(methylthio)pyrimidin-4-yl)-2-thienyl- | 1 |
| Example 113 | —OH | 5-(3-(1-methyl-5-(trifluoromethyl)pyrazolyl)-2-thienyl- | 1 |
| Example 114 | —NHP(O)(CH$_3$)C$_6$H$_5$ | CH$_3$CH$_2$CH$_2$OC$_6$H$_4$— | 1 |
| Example 115 | —NHCOCH$_2$C$_6$H$_5$ | CH$_3$CH$_2$CH$_2$OC$_6$H$_4$— | 1 |
| Example 116 | —NHCO(2-pyridyl) | CH$_3$CH$_2$CH$_2$OC$_6$H$_4$— | 1 |
| Example 117 | —NHCOCH$_2$NMe$_2$ | CH$_3$CH$_2$CH$_2$OC$_6$H$_4$— | 1 |
| Example 118 | —NHCO-2-(1-methyl)-imidazyl | CH$_3$CH$_2$CH$_2$OC$_6$H$_4$- | 1 |
| Example 119 | —NHSO$_2$CH$_3$ | 4-(4-C$_5$H$_4$N)O—C$_6$H$_4$— | 1 |
| Example 120 | —NHCOC$_6$H$_5$ | CH$_3$CH$_2$CH$_2$OC$_6$H$_4$— | 1 |
| Example 121 | —NMe$_2$ | CH$_3$CH$_2$CH$_2$OC$_6$H$_4$— | 1 |
| Example 122 | —N(CH$_2$CH$_3$)$_2$ | CH$_3$CH$_2$CH$_2$OC$_6$H$_4$— | 1 |
| Example 123 | —NMe$_2$ | 4-(4-C$_5$H$_4$N)O—C$_6$H$_4$— | 1 |
| Example 124 | —N(CH$_2$CH$_3$)$_2$ | 4-(4-C$_5$H$_4$N)O—C$_6$H$_4$— | 1 |
| Example 125 | —N(CH$_2$CH$_3$)SO$_2$CH$_3$ | CH$_3$CH$_2$CH$_2$OC$_6$H$_4$— | 1 |
| Example 126 | —N(CH$_2$CH$_3$)COCH$_3$ | CH$_3$CH$_2$CH$_2$OC$_6$H$_4$— | 1 |
| Example 127 | —N(CH$_2$CH$_3$)SO$_2$CH$_3$ | 4-(4-C$_5$H$_4$N)O—C$_6$H$_4$— | 1 |
| Example 128 | —N(CH$_2$CH$_3$)COCH$_3$ | 4-(4-C$_5$H$_4$N)O—C$_6$H$_4$— | 1 |
| Example 129 | —N(CH$_3$)CO(2-pyridyl) | CH$_3$CH$_2$CH$_2$OC$_6$H$_4$— | 1 |
| Example 130 | —N(CH$_3$)CO(4-pyridyl) | CH$_3$CH$_2$CH$_2$OC$_6$H$_4$— | 1 |
| Example 131 | —N(CH$_3$)COC$_6$H$_5$ | CH$_3$CH$_2$CH$_2$OC$_6$H$_4$— | 1 |
| Example 132 | —N(CH$_3$)CO-1N-methylpiperazine | CH$_3$CH$_2$CH$_2$OC$_6$H$_4$— | 1 |
| Example 133 | —N(CH$_3$)COH | CH$_3$CH$_2$CH$_2$OC$_6$H$_4$— | 1 |
| Example 134 | —N(CH$_3$)COCH$_2$OCH$_3$ | CH$_3$CH$_2$CH$_2$OC$_6$H$_4$— | 1 |
| Example 135 | —N(CH$_3$)COCH(CH$_3$)$_2$ | CH$_3$CH$_2$CH$_2$OC$_6$H$_4$— | 1 |
| Example 136 | —N(CH$_3$)CO(furanyl) | CH$_3$CH$_2$CH$_2$OC$_6$H$_4$— | 1 |
| Example 137 | —N(CH$_3$)CO(oxazolinyl) | CH$_3$CH$_2$CH$_2$OC$_6$H$_4$— | 1 |
| Example 138 | —N(CH$_3$)COCH$_2$CN | CH$_3$CH$_2$CH$_2$OC$_6$H$_4$— | 1 |
| Example 139 | —N(CH$_3$)CO(CH$_2$)N(CH$_3$)$_2$ | CH$_3$CH$_2$CH$_2$OC$_6$H$_4$— | 1 |
| Example 140 | —N(CH$_3$)SO$_2$-3-(1N-methylimidazyl) | CH$_3$CH$_2$CH$_2$OC$_6$H$_4$— | 1 |

-continued

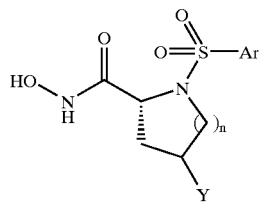

| | Y | Ar | n |
|---|---|---|---|
| Example 141 | —N(CH$_3$)SO$_2$CH(CH$_3$)$_2$ | CH$_3$CH$_2$CH$_2$OC$_6$H$_4$— | 1 |
| Example 142 | —CH$_2$NHSO$_2$CH$_3$ | CH$_3$OC$_6$H$_4$— | 1 |
| Example 143 | —CH$_2$NHSO$_2$C$_6$H$_5$ | CH$_3$OC$_6$H$_4$— | 1 |
| Example 144 | —CH$_2$NHCOC$_6$H$_5$ | CH$_3$OC$_6$H$_4$— | 1 |
| Example 145 | —CH$_2$NHCOCH$_2$CH$_2$CH$_3$ | CH$_3$OC$_6$H$_4$— | 1 |
| Example 146 | —CH$_2$N(CH$_3$)COCH$_3$ | CH$_3$OC$_6$H$_4$— | 1 |
| Example 147 | —CH$_2$N(CH$_3$)SO$_2$C$_6$H$_5$OMe | CH$_3$OC$_6$H$_4$— | 1 |
| Example 148 | —CH$_2$N(CH$_2$C$_6$H$_5$)SO$_2$CH$_3$ | CH$_3$OC$_6$H$_4$— | 1 |
| Example 149 | —OH | CH$_3$OC$_6$H$_4$— | |
| Example 150 | —S—C$_6$H$_5$ | CH$_3$OC$_6$H$_4$— | 2 |
| Example 151 | —(OMe)$_2$ | CH$_3$OC$_6$H$_4$— | 2 |
| Example 152 | —OH | BrC$_6$H$_4$— | 2 |
| Example 153 | -3-methyl-1-hydantoyl- | 4-EtO—C$_6$H$_4$— | 1 |
| Example 154 | -3-methyl-1-hydantoyl- | 4-i-PrO—C$_6$H$_4$— | 1 |
| Example 155 | -3-methyl-1-hydantoyl- | 5-(2-pyridinyl)-2-thienyl- | 1 |
| Example 156 | -3-methyl-1-hydantoyl- | 4-Br—C$_6$H$_4$— | 1 |
| Example 157 | -3-methyl-1-hydantoyl- | 2-Me-4-Br—C$_6$H$_4$— | 1 |
| Example 158 | -3-methyl-1-hydantoyl- | 4-(C$_6$H$_5$)O—C$_6$H$_4$— | 1 |
| Example 159 | -3-methyl-1-hydantoyl- | 4-(4-F—C$_6$H$_4$)O—C$_6$H$_4$— | 1 |
| Example 160 | -3-methyl-1-hydantoyl- | (4-C$_5$H$_4$N)CH$_2$CH$_2$— | 1 |
| Example 161 | -3-methyl-1-hydantoyl- | 4-(4-C$_5$H$_4$N)O—C$_6$H$_4$— | 1 |
| Example 162 | -1N-morpholino | 4-EtO—C$_6$H$_4$— | 1 |
| Example 163 | -1N-morpholino | 4-i-PrO—C$_6$H$_4$— | 1 |
| Example 164 | -1N-morpholino | 5-(2-pyridinyl)-2-thienyl- | 1 |
| Example 165 | -1N-morpholino | 4-Br—C$_6$H$_4$— | 1 |
| Example 166 | -1N-morpholino | 2-Me-4-Br—C$_6$H$_4$— | 1 |
| Example 167 | -1N-morpholino | 4-(C$_6$H$_5$)O—C$_6$H$_4$— | 1 |
| Example 168 | -1N-morpholino | 4-(4-F—C$_6$H$_4$)O—C$_6$H$_4$— | 1 |
| Example 169 | -1N-morpholino | (4-C$_5$H$_4$N)CH$_2$CH$_2$— | 1 |
| Example 170 | -1N-morpholino | 4-(4-C$_5$H$_4$N)O—C$_6$H$_4$— | 1 |
| Example 171 | -1N-valerolactamyl- | (4-C$_5$H$_4$N)OC$_6$H$_4$— | 1 |
| Example 172 | -1N-valerolactamyl- | 4-n-BuOC$_6$H$_4$— | 1 |
| Example 173 | —(OMe)$_2$ | CH$_3$CH$_2$OC$_6$H$_4$— | 1 |
| Example 174 | —(OMe)$_2$ | CH$_3$CN$_2$CH$_2$OC$_6$H$_4$— | 1 |
| Example 175 | —(OMe)$_2$ | 4-(4-C$_5$H$_4$N)O—C$_6$H$_4$— | 1 |
| Example 176 | —(OCH$_2$CH$_3$)$_2$ | CH$_3$CH$_2$OC$_6$H$_4$— | 1 |
| Example 177 | —(OCH$_2$CH$_3$)$_2$ | CH$_3$CN$_2$CH$_2$OC$_6$H$_4$— | 1 |
| Example 178 | —(OCH$_2$CH$_3$)$_2$ | 4-(4-C$_5$H$_4$N)O—C$_6$H$_4$— | 1 |
| Example 179 | —(OCH$_2$CH$_2$OCH$_3$) | CH$_3$CH$_2$OC$_6$H$_4$— | 1 |
| Example 180 | —(OCH$_2$CH$_2$OCH$_3$) | CH$_3$CN$_2$CH$_2$OC$_6$H$_4$— | 1 |
| Example 181 | —(OCH$_2$CH$_2$OCH$_3$) | 4-(4-C$_5$H$_4$N)O—C$_6$H$_4$— | 1 |

Examples 78–113 are prepared analogously to Example 1 using the appropriately functionalized sulfonyl chloride. The sulfonyl chlorides which are used to prepare the above examples are either purchased from commercial sources or prepared via known methods. For example, the 4-phenoxyphenylsulfonyl chloride used for the preparation of Example 17, was prepared as described by R. J. Cremlyn et al in *Aust. J. Chem.*, 1979, 32, 445.52.

Examples 114–120 are prepared using methods described in examples 42–61 using the appropriate alkyl, acyl, sulfonyl, phosphinyl or isocyanate derivative.

Examples 129–141 are prepared by first monomethylating the appropriate primary amine derivative as described by S. Krishnamurthy et al in *Tetrahedron Lett.* 1983, 23 (33), 3315, and then adding adding the appropriate alkyl, acyl, sulfonyl, phosphinyl or isocyanate derivative as described in examples 42–61.

Examples 142–148 are prepared from cyanide addition into mesylate 15a followed by reduction to the corresponding free amine and treatment with the appropriate alkyl, acyl, sulfonyl, or phosphinyl derivative.

Examples 149–152 are prepared by ketalization or reduction and/or nucleophillic substitution of the appropriately functionalized 4-ketopipecolic acid described by J.-P. Obrecht et al in *Organic Synthesis* 1992, 200.

Examples 153–161 are prepared as described for example 68.

Examples 162–170 are prepared as described for example 65.

Examples 171–172 are prepared by acylation of a primary amine of type 43c with 5-bromovaleryl chloride followed base promoted ring closure and hydroxamic acid formation.

Examples 173–181 are prepared by standard ketalization methods of ketones of type 25a.

These examples provide the skilled artisan with sufficient guidance as to making the present invention and do not limit it in any way.

Composition and Method of Use Examples

The compounds of the invention are useful to prepare compositions for the treatment of ailments and the like. The following composition and method examples do not limit the invention, but provide guidance to the skilled artisan to prepare and use the compounds, compositions and methods of the invention. In each case the compounds formula I may be substituted for the example compound shown below with similar results.

The methods of use exemplified do not limit the invention, but provide guidance to the skilled artisan to use the compounds, compositions and methods of the invention. The skilled practitioner will appreciate that the examples provide guidance and may be varied based on condition and the patient.

Example A

A tablet composition for oral administration, according to the present invention, is made comprising:

| Component | Amount |
|---|---|
| The compound of Example 9 | 15. mg |
| Lactose | 120. mg |
| Maize Starch | 70. mg |
| Talc | 4. mg |
| Magnesium Stearate | 1. mg |

(Other compounds having a structure according to Formula (I) are used with substantially similar results.)

A human female subject weighing 60 kg (132 lbs), suffering from rheumatoid arthritis, is treated by a method of this invention. Specifically, for 2 years, a regimen of three tablets per day is administered orally to said subject.

At the end of the treatment period, the patient is examined and is found to have reduced inflammation, and improved mobility without concomitant pain.

Example B

A capsule for oral administration, according to the present invention, is made comprising:

| Component | Amount (% w/w) |
|---|---|
| The compound of Example 3 | 15% |
| Polyethylene glycol | 85% |

(Other compounds having a structure according to Formula (I) are used with substantially similar results.)

A human male subject weighing 90 kg (198 lbs), suffering from osteoarthritis, is treated by a method of this invention. Specifically, for 5 years, a capsule containing 70 mg of the compound of Example 3 is administered daily to said subject.

At the end of the treatment period, the patient is examined via orthoscopy, and found to have no further advancement of erosion/fibrillation of the articular cartilage.

Example C

A saline-based composition for local administration, according to the present invention, is made comprising:

| Component | Amount (% w/w) |
|---|---|
| The compound of Example 13 | 5% |
| Polyvinyl alcohol | 15% |
| Saline | 80% |

(Other compounds having a structure according to Formula (I) are used with substantially similar results.)

A patient having deep corneal abrasion applies the drop to each eye twice a day. Healing is speeded, with no visual sequelae.

Example D

A topical composition for local administration, according to the present invention, is made comprising:

| Component | Composition (% w/v) |
|---|---|
| The compound of Example 3 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

(Other compounds having a structure according to Formula (I) are used with substantially similar results.)

A patient suffering from chemical burns applies the composition at each dressing change (b.i.d.). Scarring is substantially diminished.

Example E

A inhalation aerosol composition, according to the present invention, is made comprising:

| Component | Composition (% w/v) |
|---|---|
| Compound of Example 2 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

(Other compounds having a structure according to Formula (I) are used with substantially similar results.)

An asthma sufferer sprays 0.01 mL via a pump actuator into the mouth while inhaling. Asthma symptoms are diminished.

Example F

A topical opthalmic composition, according to the present invention, is made comprising:

| Component | Composition (% w/v) |
|---|---|
| Compound of Example 5 | 0.10 |
| Benzalkonium chloride | 0.01 |
| EDTA | 0.05 |
| Hydroxyethylcellulose (NATROSOL M) | 0.50 |
| Sodium metabisulfite | 0.10 |
| Sodium chloride (0.9%) | q.s. |
| Total = | 100.0 |

(Other compounds having a structure according to Formula (I) are used with substantially similar results.)

A human male subject weighing 90 kg (198 lbs), suffering from corneal ulcerations, is treated by a method of this invention. Specifically, for 2 months, a saline solution containing 10 mg of the compound of Example 5 is administered to said subject's affected eye twice-daily.

Example G

A composition for parenteral administration is made comprising:

| Component | Amount |
|---|---|
| The compound of Example 4 | 100 mg/ml carrier |
| Carrier: | |
| sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 ml of the suspension is administered, via injection, to a human subject with a premetastatic tumor. The injection site juxtaposes the tumor. This dosage is repeated twice daily, for approximately 30 days. After 30 days, symptoms of the disease subside, and dosage is gradually decreased to maintain the patient.

(Other compounds having a structure according to Formula I are used with substantially similar results.)

Example H

A mouthwash composition is prepared;

| Component | % w/v |
|---|---|
| The compound of Example 1 | 3.00 |
| SDA 40 Alcohol | 8.00 |
| Flavor | 0.08 |
| Emulsifier | 0.08 |
| Sodium Fluoride | 0.05 |
| Glycerin | 10.00 |
| Sweetener | 0.02 |
| Benzoic acid | 0.05 |
| Sodium hydroxide | 0.20 |
| Dye | 0.04 |
| Water | balance to 100% |

A patient with gum disease uses 1 ml of the mouthwash thrice daily to prevent further oral degeneration.

(Other compounds having a structure according to Formula I are used with substantially similar results.)

Example I

A lozenge composition is prepared;

| Component | % w/v |
|---|---|
| The compound of Example 3 | 0.01 |
| Sorbitol | 17.50 |
| Mannitol | 17.50 |
| Starch | 13.60 |
| Sweetener | 1.20 |
| Flavor | 11.70 |
| Color | 0.10 |
| Corn Syrup | balance to 100% |

A patient uses the losenge to prevent loosening of an implant in the maxilla. (Other compounds having a structure according to Formula I are used with substantially similar results.)

Example J

Chewing Gum Composition

| Component | w/v % |
|---|---|
| The compound of Example 1 | 0.03 |
| Sorbitol crystals | 38.44 |
| Paloja-T gum base* | 20.00 |
| Sorbitol (70% aqueous solution) | 22.00 |
| Mannitol | 10.00 |
| Glycerine | 7.56 |
| Flavor | 1.00 |

A patient chews the gum to prevent loosening of dentures.

(Other compounds having a structure according to Formula I are used with substantially similar results.)

Example K

| Components | w/v % |
|---|---|
| Compound of example 25 | 4.0 |
| USP Water | 50.656 |
| Methylparaben | 0.05 |
| Propylparaben | 0.01 |
| Xanthan Gum | 0.12 |
| Guar Gum | 0.09 |
| Calcium carbonate | 12.38 |
| Antifoam | 1.27 |
| Sucrose | 15.0 |
| Sorbitol | 11.0 |
| Glycerin | 5.0 |

-continued

| Components | w/v % |
|---|---|
| Benzyl Alcohol | 0.2 |
| Citric Acid | 0.15 |
| Coolant | 0.00888 |
| Flavor | 0.0645 |
| Colorant | 0.0014 |

The composition is prepared by first mixing 80 kg of gylcerin and all of the benzyl alcohol and heating to 65 C, then slowly adding and mixing together methylparaben, propylparaben, water, xanthan gum, and guar gum. Mix these ingredients for about 12 minutes with a Silverson in-line mixer. Then slowly add in the following ingredients in the following order: remaining glycerin, sorbitol, antifoam C, calcium carbonate, citric acid, and sucrose. Separately combine flavors and coolants and then slowly add to the other ingredients. Mix for about 40 minutes.

The patient takes the formulation to prevent flare up of colitis.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A method of preventing or treating a chronic heart failure comprising administering to a mammal in need of such treatment, a safe and effective amount of a compound of having a structure according to Formula (I):

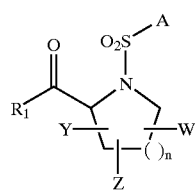

(I)

wherein
A is alkyl, heteroalkyl, aryl or heteroaryl, substituted or unsubstituted;
$R_1$ is $NHOR_2$, where $R_2$ is hydrogen or alkyl;
W is one or more of hydrogen, lower alkyl, or an alkylene bridge that forms a ring in addition to the ring depicted in Formula (I);
Y is independently one or more of hydroxy, $SR_3$, $SOR_4$, $SO_2R_8$, alkoxy, or amino, wherein the amino is of formula $NR_6R_7$, wherein $R_6$ and $R_7$ are independently chosen from hydrogen, alkyl, heteroalkyl, heteroaryl, aryl, $OR_3$, $SO_2R_8$, $COR_9$, $CSR_{10}$, and $PO(R_{11})_2$;
$R_3$ is hydrogen, alkyl, aryl, or heteroaryl;
$R_4$ is alkyl, aryl, or heteroaryl;
each $R_8$ is independently chosen from group consisting of alkyl, aryl, heteroaryl, heteroalkyl, amino, alkylamino, dialkylamino, arylamino, diarylamino and alkylarylamino;
$R_9$ is hydrogen, alkoxy, aryloxy, heteroaryloxy, alkyl, aryl, heteroaryl, heteroalkyl, amino, alkylamino, dialkylamino, arylamino or alkylarylamino;
$R_{10}$ is alkyl, aryl, heteroaryl, heteroalkyl, amino, alkylamino, dialkylamino, arylamino, diarylamino or alkylarylamino;
$R_{11}$ is alkyl, aryl, heteroaryl, or heteroalkyl;
Z is hydrogen, hydroxy, alkyl, or an alkylene or heteroalkylene bridge that forms a ring in addition to the ring depicted in Formula (I);
n is 1; and
provided that (i) when any one or more of $R_3$, $R_4$, $R_8$, $R_9$, $R_{10}$, $R_{11}$, W, Y or Z is itself, or together with another moiety forms, a heterocyclic moiety, that heterocyclic moiety is furan, and (ii) when W or Z is an alkylene or heteroalkylene bridge that forms a second ring fused to the ring depicted in Formula (I), that second ring does not include the ring carbon atom depicted in Formula (I) that is bonded to C(=O)—$R_1$; or
an optical isomer, diastereomer or enantiomer for Formula (I), or a pharmaceutically-acceptable salt, or biohydrolyzable amide, ester, or imide thereof.

2. The method of claim 1, wherein the compound is of structure:

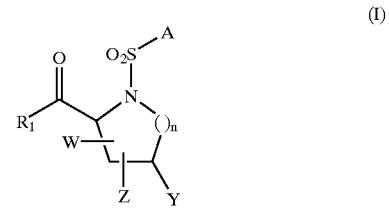

(I)

wherein
A is aryl or heteroaryl, substituted or unsubstituted;
$R_1$ is $NHOR_2$, where $R_2$ is hydrogen or alkyl;
W is one or more of hydrogen or lower alkyl;
Y is independently one or more of hydroxy, $SR_3$, $SOR_4$, $SO_2R_8$, alkoxy, or amino, wherein the amino is of formula $NR_6R_7$, wherein $R_6$ and $R_7$ are independently chosen from hydrogen, alkyl, heteroalkyl, heteroaryl, aryl, $OR_3$, $SO_2R_8$, $COR_9$, $CSR_{10}$ and $PO(R_{11})_2$;
$R_3$ is hydrogen, alkyl, aryl, or heteroaryl;
$R_4$ is alkyl, aryl, or heteroaryl;
each $R_8$ is independently chosen from the group consisting of alkyl, aryl, heteroaryl, heteroalkyl, amino, alkylamino, dialkylamino, arylamino, diarylamino and alkylarylamino;
$R_9$ is hydrogen, alkoxy, aryloxy, heteroaryloxy, alkyl, aryl, heteroaryl, heteroalkyl, amino, alkylamino, dialkylamino, arylamino or alkylarylamino;
$R_{10}$ is alkyl, aryl, heteroaryl, heteroalkyl, amino, alkylamino, dialkylamino, arylamino, diarylamino, or alkylarylamino;
$R_{11}$ is alkyl, aryl, heteroaryl, or heteroalkyl;
Z is hydrogen; and
n is 1; or
an optical isomer, diastereomer or enantiomer for Formula (I), or a pharmaceutically-acceptable salt, or biohydrolyzable amide, ester, or imide thereof.

3. The method of claim 2, wherein the compound is selected from the group consisting of:
(1N)-(4-Methoxyphenylsulfonyl)-(2R)-N-hydroxycarboxamido-(4S)-hydroxypyrrolidine;
((1N)-(4-Methoxyphenylsulfonyl)-(2R)-N-hydroxycarboxamido-(4S)-hydroxypyrrolidine;

(1N)-(4-Methoxyphenylsulfonyl)-(2S)-N-hydroxycarboxamido-(4R)-hydroxypyrrolidine;
(1N)-(4-Methoxyphenylsulfonyl)-(2S)-N-hydroxycarboxamido-(4S)-hydroxypyrrolidine;
(1N)-(4-Methoxyphenylsulfonyl)-(2R)-N-hydroxycarboxamido-(4S)-methoxypyrrolidine;
(1N)-(4-Methoxyphenylsulfonyl)-(2R)-N-hydroxycarboxamido-(4S)-(2-mercaptobenzothiazolyl)-pyrrolidine;
(1N)-(4-Methoxyphenylsulfonyl)-(2R)-N-hydroxycarboxamido-(4R)-(2-mercaptobenzothiazolyl)-pyrrolidine;
(1N)-(4-Methoxyphenylsulfonyl)-(2R)-N-hydroxycarboxamido-(4S)-[(1N)-methyl-2-mercaptoimidazyl]-pyrrolidine;
(1N)-(4-Methoxyphenylsulfonyl)-(2R)-N-hydroxycarboxamido-(4R)-[(1N)-methyl-2-mercaptoimidazyl]-pyrrolidine;
(1N)-(4-Methoxyphenylsulfonyl)-(2R)-N-hydroxycarboxamido-(4S)-phenoxypyrrolidine;
(1N)-(4-Methoxyphenylsulfonyl)-(2R)-N-hydroxycarboxamido-(4S)-(4-benzyloxy)-phenoxypyrrolidine;
(1N)-4-Methoxyphenylsulfonyl-(2R)-N-hydroxycarboxamido-(4S)-(3-N-phenylamino)-phenoxypyrrolidine;
(1N)-4-Methoxyphenylsulfonyl-(2R)-N-hydroxycarboxamido-(4S)-phenoxypyrrolidine;
(1N)-4-Methoxyphenylsulfonamido-(2R)-N-hydroxycarboxamido-(4S)-mercaptophenylpyrrolidine;
(1N)-(4-Methoxyphenylsulfonyl)-(2R)-N-hydroxycarboxamido-(4S)-(4-methoxyphenylthioloxy)-pyrrolidine;
(1N)-(4-Methoxyphenylsulfonyl)-(2R)-N-hydroxycarboxamido-(4S)-(3-methoxymercaptophenyl)-pyrrolidine;
(1N)-(4-Methoxyphenylsulfonyl)-(2R)-N-hydroxycarboxamido-(4S)-("hexylamino)-pyrrolidine;
(1N)-(4-Methoxyphenylsulfonyl)-(2R)-hydroxycarboxamido-(4S)-thiopyrrolidine;
(±)-(1N)-(4-Methoxyphenylsulfonyl)-(2R)-N-hydroxycarboxamido-(3S)-phenylpyrrolidine;
(1N)-(4-Methylphenylsulfonyl)-(2R)-N-hydroxycarboxamido-(4S)-hydroxypyrrolidine;
(1N)-(3,4-Dimethoxyphenylsulfonyl)-(2R)-N-hydroxycarboxamido-(4R)-hydroxypyrrolidine;
(1N)-(2-Nitro-4-methoxyphenylsulfonyl)-(2R)-N-hydroxycarboxamido-(4R)-hydroxypyrrolidine;
(1N)-4-"Butoxyphenylsulfonamido-(2R)-N-hydroxycarboxamido-(4R)-hydroxypyrrolidine;
(1N)-(4-"Butoxyphenylsulfonyl)-(2R)-N-hydroxycarboxamido-(4S)-hydroxypyrrolidine;
(1N)-(4-"Butoxyphenylsulfonyl)-(2R)-N-hydroxycarboxamido-(4S)-(2-mercaptobenzothiazolyl)-pyrrolidine;
(1N)-(2-Nitro-4-methoxyphenylsulfonyl)-(2R)-N-hydroxycarboxamido-(4S)-(2-mercaptobenzothiazolyl)-pyrrolidine;
(1N)-(4-Methoxyphenylsulfonyl)-(2R)-N-hydroxycarboxamido-(4S)-(4-methoxyphenylthioloxy)-pyrrolidine;
(±)-(1N)-4-Methoxyphenylsulfonyl-(2R)-N-hydroxycarboxamido-5-pyrrolidinone;
(1N)-4-Methoxyphenylsulfonyl-(2R)-hydroxycarboxamido-(4,4R)-hydroxyethylpyrrolidine; (1N)-4-Phenoxyphenylsulfonyl-(2)-N-hydroxycarboxamido-(4R)-hydroxypyrrolidine; and
(1N)-(4-"Butoxyphenylsulfonyl)-(2R)-N-hydroxycarboxamido-(4S)-morpholinopyrrolidine.

4. The method according to claim 3, wherein the compound is selected from the group consisting of:
(1N)-Phenoxyphenylsulfonyl)-(2R)-carbomethoxy-(4R)-hydroxypyrrolidine;
(1N)-4-"Butoxyphenylsulfonamido-(2R)-N-hydroxycarboxamido-(4R)-hydroxypyrrolidine;
(1N)-4-"Butoxyphenylsulfonyl)-2R)-N-hydroxycarboxamido-(4S)-hydroxypyrrolidine; and
(1N)-(4-"Butoxyphenylsulfonyl)-2R)-N-hydroxycarboxamido-(4S)-morpholinopyrrolidine.

5. A method of preventing or treating a myocardial infarction comprising administering to a mammal in need of such treatment, a safe and effective amount of a compound of having a structure according to Formula (I):

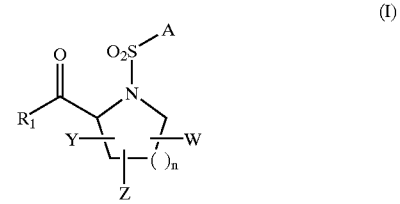

wherein
A is alkyl, heteroalkyl, aryl or heteroaryl, substituted or unsubstituted;
$R_1$ is $NHOR_2$, where $R_2$ is hydrogen or alkyl;
W is one or more of hydrogen, lower alkyl, or an alkylene bridge that forms a ring in addition to the ring depicted in Formula (I);
Y is independently one or more of hydroxy, $SR_3$, $SOR_4$, $SO_2R_8$, alkoxy, or amino, wherein the amino is of formula $NR_6,R_7$, wherein $R_6$ and $R_7$ are independently chosen from hydrogen, alkyl, heteroalkyl, heteroaryl, aryl, $OR_3$, $SO_2R_8$, $COR_9$, $CSR_{10}$, and $PO(R_{11})_2$;
$R_3$ is hydrogen, alkyl, aryl, or heteroaryl;
$R_4$ is alkyl, aryl, or heteroaryl;
each $R_8$ is independently chosen from group consisting of alkyl, aryl, heteroaryl, heteroalkyl, amino, alkylamino, dialkylamino, arylamino, diarylamino and alkylarylamino;
$R_9$ is hydrogen, alkoxy, aryloxy, heteroaryloxy, alkyl, aryl, heteroaryl, heteroalkyl, amino, alkylamino, dialkylamino, arylamino or alkylarylamino;
$R_{10}$ is alkyl, aryl, heteroaryl, heteroalkyl, amino, alkylamino, dialkylamino, arylamino, diarylamino or alkylarylamino;
$R_{11}$, is alkyl, aryl, heteroaryl, or heteroalkyl;
Z is hydrogen, hydroxy, alkyl, or an alkylene or heteroalkylene bridge that forms a ring in addition to the ring depicted in Formula (I);
n is 1; and
provided that (i) when any one or more of $R_3$, $R_4$, $R_8$, $R_9$, $R_{10}$, $R_{11}$, W, Y or Z is itself, or together with another moiety forms, a heterocyclic moiety, that heterocyclic moiety is furan, and (ii) when W or Z is an alkylene or heteroalkylene bridge that forms a second ring fused to the ring depicted in Formula (I), that second ring does not include the ring carbon atom depicted in Formula (I) that is bonded to C(=O)—R$_1$; or an optical isomer, diastereomer or enantiomer for Formula (I), or a pharmaceutically-acceptable salt, or biohydrolyzable amide, ester, or imide thereof.

6. The method of claim 5, wherein the compound is of structure:

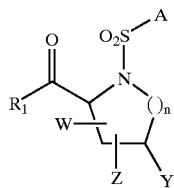
(I)

wherein

A is aryl or heteroaryl, substituted or unsubstituted;

R$_1$ is NHOR$_2$, where R$_2$ is hydrogen or alkyl;

W is one or more of hydrogen or lower alkyl;

Y is independently one or more of hydroxy, SR$_3$, SOR$_4$, SO$_2$R$_8$, alkoxy, or amino, wherein the amino is of formula NR$_6$,R$_7$, wherein R$_6$ and R$_7$ are independently chosen from hydrogen, alkyl, heteroalkyl, heteroaryl, aryl, OR$_3$, SO$_2$R$_8$, COR$_9$, CSR$_{10}$ and PO(R$_{11}$)$_2$;

R$_3$ is hydrogen, alkyl, aryl, or heteroaryl;

R$_4$ is alkyl, aryl, or heteroaryl;

each R$_8$ is independently chosen from the group consisting of alkyl, aryl, heteroaryl, heteroalkyl, amino, alkylamino, dialkylamino, arylamino, diarylamino and alkylarylamino;

R$_9$ is hydrogen, alkoxy, aryloxy, heteroaryloxy, alkyl, aryl, heteroaryl, heteroalkyl, amino, alkylamino, dialkylamino, arylamino or alkylarylamino;

R$_{10}$ is alkyl, aryl, heteroaryl, heteroalkyl, amino, alkylamino, dialkylamino, arylamino, diarylamino, or alkylarylamino;

R$_{11}$ is alkyl, aryl, heteroaryl, or heteroalkyl;

Z is hydrogen; and n is 1; or an optical isomer, diastereomer or enantiomer for Formula (I), or a pharmaceutically-acceptable salt, or biohydrolyzable amide, ester, or imide thereof.

7. The method of claim 6, wherein the compound is selected from the group consisting of:

(1N)-(4-Methoxyphenylsulfonyl)-(2R)-N-hydroxycarboxamido-(4S)-hydroxypyrrolidine;

((1N)-(4-Methoxyphenylsulfonyl)-(2R)-N-hydroxycarboxamido-(4S)-hydroxypyrrolidine;

(1N)-(4-Methoxyphenylsulfonyl)-(2S)-N-hydroxycarboxamido-(4R)-hydroxypyrrolidine;

(1N)-(4-Methoxyphenylsulfonyl)-(2S)-N-hydroxycarboxamido-(4S)-hydroxypyrrolidine;

(1N)-(4-Methoxyphenylsulfonyl)-(2R)-N-hydroxycarboxamido-(4S)-methoxypyrrolidine;

(1N)-(4-Methoxyphenylsulfonyl)-(2R)-N-hydroxycarboxamido-(4S)-(2-mercaptobenzothiazolyl)-pyrrolidine;

(1N)-(4-Methoxyphenylsulfonyl)-(2R)-N-hydroxycarboxamido-(4R)-(2-mercaptobenzothiazolyl)-pyrrolidine;

(1N)-(4-Methoxyphenylsulfonyl)-(2R)-N-hydroxycarboxamido-(4S)-[(1N)-methyl-2-mercaptoimidazyl]-pyrrolidine;

(1N)-(4-Methoxyphenylsulfonyl)-(2R)-N-hydroxycarboxamido-(4R)-[(1N)-methyl-2-mercaptoimidazyl]-pyrrolidine;

(1N)-(4-Methoxyphenylsulfonyl)-(2R)-N-hydroxycarboxamido-(4S)-phenoxypyrrolidine;

(1N)-(4-Methoxyphenylsulfonyl)-(2R)-N-hydroxycarboxamido-(4S)-(4-benzyloxy)-phenoxypyrrolidine;

(1N)-4-Methoxyphenylsulfonyl-(2R)-N-hydroxycarboxamido-(4S)-(3-N-phenylamino)-phenoxypyrrolidine;

(1N)-4-Methoxyphenylsulfonyl-(2R)-N-hydroxycarboxamido-(4S)-phenoxypyrrolidine;

(1N)-4-Methoxyphenylsulfonamido-(2R)-N-hydroxycarboxamido-(4S)-mercaptophenylpyrrolidine;

(1N)-(4-Methoxyphenylsulfonyl)-(2R)-N-hydroxycarboxamido-(4S)-(4-methoxyphenylthioloxy)-pyrrolidine;

(1N)-(4-Methoxyphenylsulfonyl)-(2R)-N-hydroxycarboxamido-(4S)-(3-methoxymercaptophenyl)-pyrrolidine;

(1N)-(4-Methoxyphenylsulfonyl)-(2R)-N-hydroxycarboxamido-(4S)-("hexylamino)-pyrrolidine;

(1N)-(4-Methoxyphenylsulfonyl)-(2R)-hydroxycarboxamido-(4S)-thiopyrrolidine;

(±)-(1N)-(4-Methoxyphenylsulfonyl)-(2R)-N-hydroxycarboxamido-(3S)-phenylpyrrolidine;

(1N)-(4-Methylphenylsulfonyl)-(2R)-N-hydroxycarboxamido-(4S)-hydroxypyrrolidine;

(1N)-(3,4-Dimethoxyphenylsulfonyl)-(2R)-N-hydroxycarboxamido-(4R)-hydroxypyrrolidine;

(1N)-(2-Nitro-4-methoxyphenylsulfonyl)-(2R)-N-hydroxycarboxamido-(4R)-hydroxypyrrolidine;

(1N)-4-"Butoxyphenylsulfonamido-(2R)-N-hydroxycarboxamido-(4R)-hydroxypyrrolidine;

(1N)-(4-"Butoxyphenylsulfonyl)-(2R)-N-hydroxycarboxamido-(4S)-hydroxypyrrolidine;

(1N)-(4-"Butoxyphenylsulfonyl)-(2R)-N-hydroxycarboxamido-(4S)-(2-mercaptobenzothiazolyl)-pyrrolidine;

(1N)-(2-Nitro-4-methoxyphenylsulfonyl)-(2R)-N-hydroxycarboxamido-(4S)-(2-mercaptobenzothiazolyl)-pyrrolidine;

(1N)-(4-Methoxyphenylsulfonyl)-(2R)-N-hydroxycarboxamido-(4S)-(4-methoxyphenylthioloxy)-pyrrolidine;

(±)-(1N)-4-Methoxyphenylsulfonyl-(2R)-N-hydroxycarboxamido-5-pyrrolidinone;

(1N)-4-Methoxyphenylsulfonyl-(2R)-hydroxycarboxamido-(4,4R)-hydroxyethylpyrrolidine; (1N)-4-Phenoxyphenylsulfonyl-(2R)-N-hydroxycarboxamido-(4R)-hydroxypyrrolidine; and (1N)-(4-"Butoxyphenylsulfonyl-(2R)-N-hydroxycarboxamido-(4S)-morpholinopyrrolidine.

8. The method of claim 7, wherein the compound is selected from the group consisting of:

(1N)-Phenoxyphenylsulfonyl)-(2R)-N-hydroxycarboxamido-(4R)-hydroxypyrrolidine;

(1N)-4-"Butoxyphenylsulfonamido-(2R)-N-hydroxycarboxamido-(4R)-hydroxypyrrolidine;

(1N)-4-"Butoxyphenylsulfonyl)-2R)-N-hydroxycarboxamido-(4S)-hydroxypyrrolidine; and (1N)-(4-"Butoxyphenylsulfonyl)-(2R)-N-hydroxycarboxamido-(4S)-morpholinopyrrolidine.

* * * * *